United States Patent
Caputi et al.

(10) Patent No.: US 12,042,568 B2
(45) Date of Patent: Jul. 23, 2024

(54) ADHESIVE FOR AN ABSORBENT ARTICLE

(71) Applicant: The Procter & Gamble Company, Cincinnati, OH (US)

(72) Inventors: Mariangela Caputi, Oescara (DE); Vito Carla, Fairfield, OH (US); Matthias Morand, Sulzbach am Taunus (DE); Andrea Pfarr Switzer, Maineville, OH (US); Tana Kirkbride, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 490 days.

(21) Appl. No.: 17/237,559

(22) Filed: Apr. 22, 2021

(65) Prior Publication Data

US 2021/0330520 A1    Oct. 28, 2021

Related U.S. Application Data

(60) Provisional application No. 63/013,573, filed on Apr. 22, 2020.

(51) Int. Cl.
*A61L 15/58* (2006.01)
*A61F 13/56* (2006.01)
(Continued)

(52) U.S. Cl.
CPC ......... *A61L 15/585* (2013.01); *A61F 13/5611* (2013.01); *C09J 7/387* (2018.01);
(Continued)

(58) Field of Classification Search
CPC .. A61L 15/585; A61F 13/5611; A61F 13/472; C09J 7/387; C09J 123/0853;
(Continued)

(56) References Cited

U.S. PATENT DOCUMENTS

| | | | |
|---|---|---|---|
| 4,460,364 | A | 7/1984 | Chen et al. |
| 4,554,304 | A | 11/1985 | Hansen et al. |

(Continued)

FOREIGN PATENT DOCUMENTS

| | | | |
|---|---|---|---|
| AU | 9398298 | A | 4/1999 |
| AU | 745377 | B2 | 3/2002 |

(Continued)

OTHER PUBLICATIONS

All Office Actions for U.S. Appl. No. 17/237,174, filed Apr. 22, 2021.

(Continued)

*Primary Examiner* — Susan S Su
*Assistant Examiner* — Eric Rassavong
(74) *Attorney, Agent, or Firm* — Angela K. Haughey; Amanda Herman Berghauer; George H. Leal

(57) ABSTRACT

An absorbent article is disclosed. The absorbent article has a longitudinal centerline, a transverse centerline generally perpendicular to the longitudinal centerline, a wearer-facing surface and an opposing garment-facing surface, a front end region, an opposing back end region, and a central region disposed between the front end region and the back end region. The absorbent article further includes a topsheet; a backsheet; an absorbent system disposed between the topsheet and the backsheet; and a plurality of pre-formed adhesive portions disposed on the garment-facing surface. The absorbent article exhibits a peel force of at least 1.0 N in accordance with the Peel Force test and leaves no residue in accordance with the Adhesive Residue test method.

20 Claims, 49 Drawing Sheets

(51) Int. Cl.
*C09J 7/38* (2018.01)
*C09J 7/40* (2018.01)
*C09J 123/08* (2006.01)
*C09J 131/04* (2006.01)
*C09J 153/02* (2006.01)

(52) U.S. Cl.
CPC ....... C09J 123/0853 (2013.01); C09J 131/04 (2013.01); C09J 153/02 (2013.01); *C09J 7/405* (2018.01); *C09J 2301/124* (2020.08)

(58) Field of Classification Search
CPC ........ C09J 131/04; C09J 153/02; C09J 7/405; C09J 2301/124; C09J 2203/358; C09J 2301/302; C09J 2301/312; C09J 2400/263; C09J 2453/00; C09J 7/29
See application file for complete search history.

(56) References Cited

U.S. PATENT DOCUMENTS

| | | | |
|---|---|---|---|
| 4,719,261 A | | 1/1988 | Bunnelle et al. |
| 4,810,523 A | | 3/1989 | Williams et al. |
| 5,100,963 A | | 3/1992 | Lin |
| 5,459,193 A | | 10/1995 | Anderson et al. |
| 5,559,165 A | | 9/1996 | Paul |
| 6,103,814 A | | 8/2000 | Vandrongelen et al. |
| 6,123,890 A | | 9/2000 | Mazurek et al. |
| 6,280,557 B1 | | 8/2001 | Peloquin |
| 6,465,557 B1 | | 10/2002 | De Keyzer |
| 6,497,949 B1 | | 12/2002 | Hyde et al. |
| 6,620,143 B1 | | 9/2003 | Zacharias et al. |
| 7,842,022 B2 | | 11/2010 | Veglio |
| 8,029,483 B2 | | 10/2011 | Bonelli |
| 2003/0168165 A1 | | 9/2003 | Hatfield |
| 2005/0203478 A1* | | 9/2005 | Veglio .................... A61L 15/42 604/387 |
| 2005/0256481 A1 | | 11/2005 | Rosati et al. |
| 2006/0229411 A1 | | 10/2006 | Hatfield et al. |
| 2008/0014387 A1* | | 1/2008 | Murphy .................... B32B 5/32 428/40.1 |
| 2009/0062761 A1* | | 3/2009 | Goerg-Wood ...... A61F 13/5611 604/385.01 |
| 2010/0158825 A1 | | 6/2010 | Maesen et al. |
| 2010/0330354 A1 | | 12/2010 | Tsukagoshi et al. |
| 2013/0158491 A1 | | 6/2013 | Caputi et al. |
| 2014/0186566 A1* | | 7/2014 | Wood ........................ C09J 7/22 428/114 |
| 2014/0293546 A1 | | 10/2014 | Wu |
| 2014/0371703 A1 | | 12/2014 | Davis et al. |
| 2015/0034244 A1 | | 2/2015 | Austin et al. |
| 2015/0038936 A1 | | 2/2015 | Austin |
| 2015/0038938 A1* | | 2/2015 | Austin ................ A61F 13/5616 604/387 |
| 2016/0143791 A1 | | 5/2016 | Wood et al. |
| 2016/0166447 A1 | | 6/2016 | Toro et al. |
| 2017/0049923 A1 | | 2/2017 | Olsen et al. |
| 2017/0348157 A1 | | 12/2017 | Patchett |
| 2018/0030321 A1* | | 2/2018 | Tunius .................... A61P 17/02 |
| 2018/0222171 A1 | | 8/2018 | Degroot et al. |
| 2019/0321241 A1 | | 10/2019 | Turner et al. |
| 2020/0030162 A1 | | 1/2020 | Lindner et al. |
| 2021/0330856 A1 | | 10/2021 | Caputi et al. |

FOREIGN PATENT DOCUMENTS

| | | | | |
|---|---|---|---|---|
| CN | 1079141 A | 12/1993 | | |
| CN | 1283981 A | 2/2001 | | |
| CN | 1929875 A | 3/2007 | | |
| CN | 1929876 A | 3/2007 | | |
| CN | 1956691 A | 5/2007 | | |
| CN | 104338170 A | 2/2015 | | |
| CN | 106999323 A | 8/2017 | | |
| EP | 0700276 B1 | 7/2002 | | |
| EP | 1262531 A1 | 12/2002 | | |
| EP | 1054932 B1 | 8/2005 | | |
| EP | 2821036 A1 | 1/2015 | | |
| EP | 2835137 A1 | 2/2015 | | |
| EP | 2901973 A1 | 8/2015 | | |
| WO | WO-9915123 A1 * | 4/1999 | .......... A61F 13/5611 |
| WO | 2015076189 A1 | 5/2015 | | |
| WO | 2016149375 A1 | 9/2016 | | |

OTHER PUBLICATIONS

PCT Search Report and Written Opinion for PCT/US2021/028625 dated Aug. 5, 2021, 13 pages.

* cited by examiner

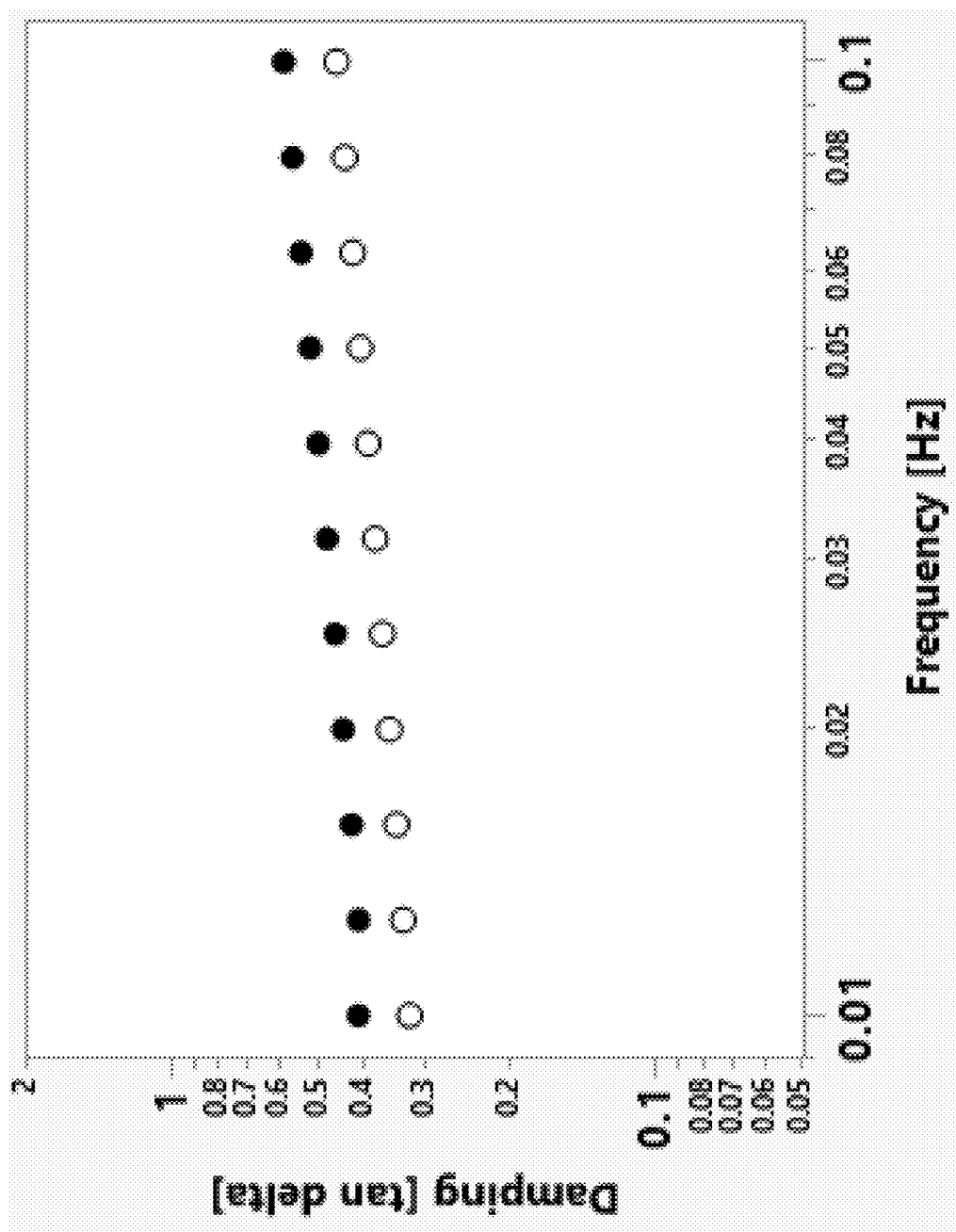
FIG. 5A Sample 1

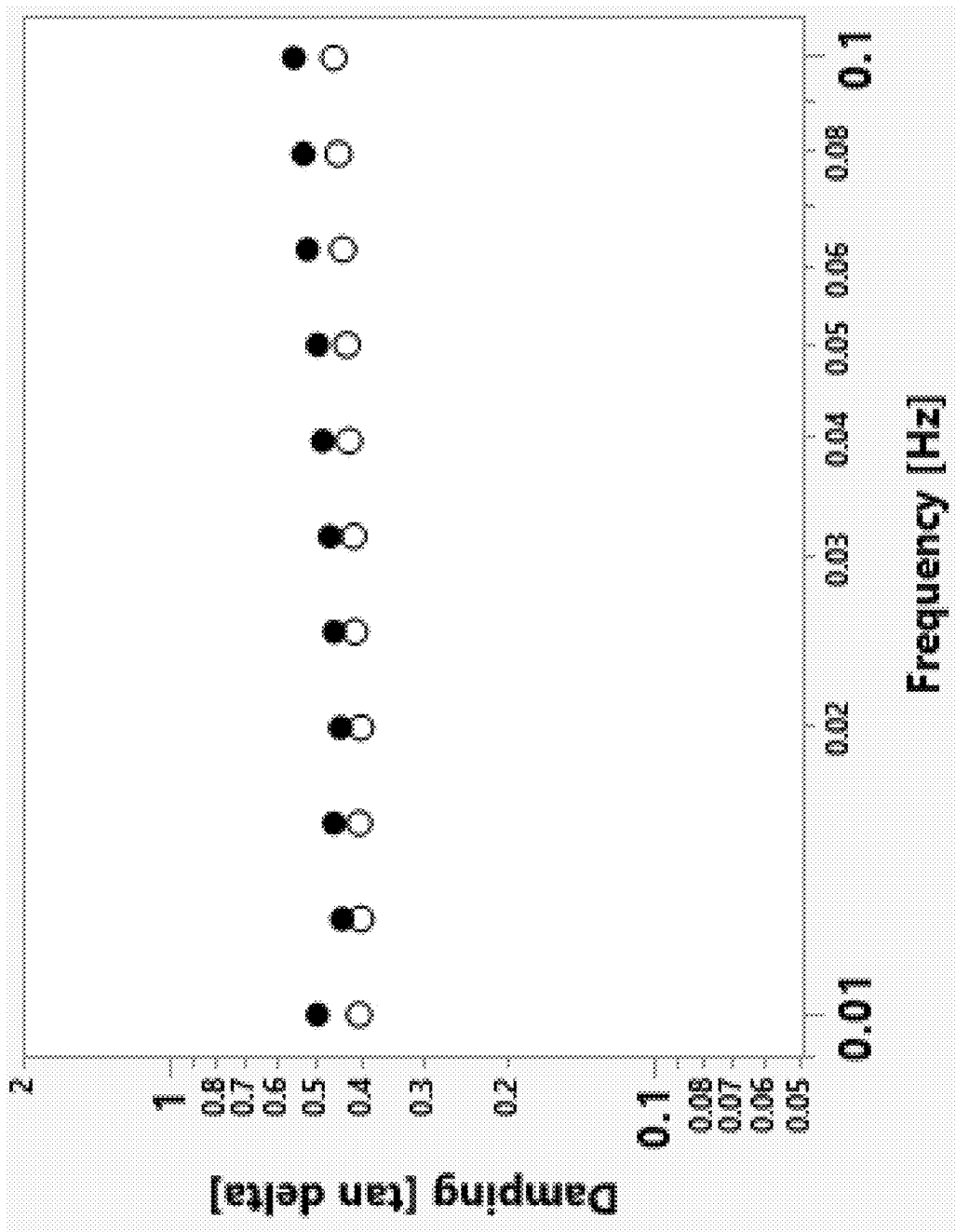
FIG. 5B Sample 2

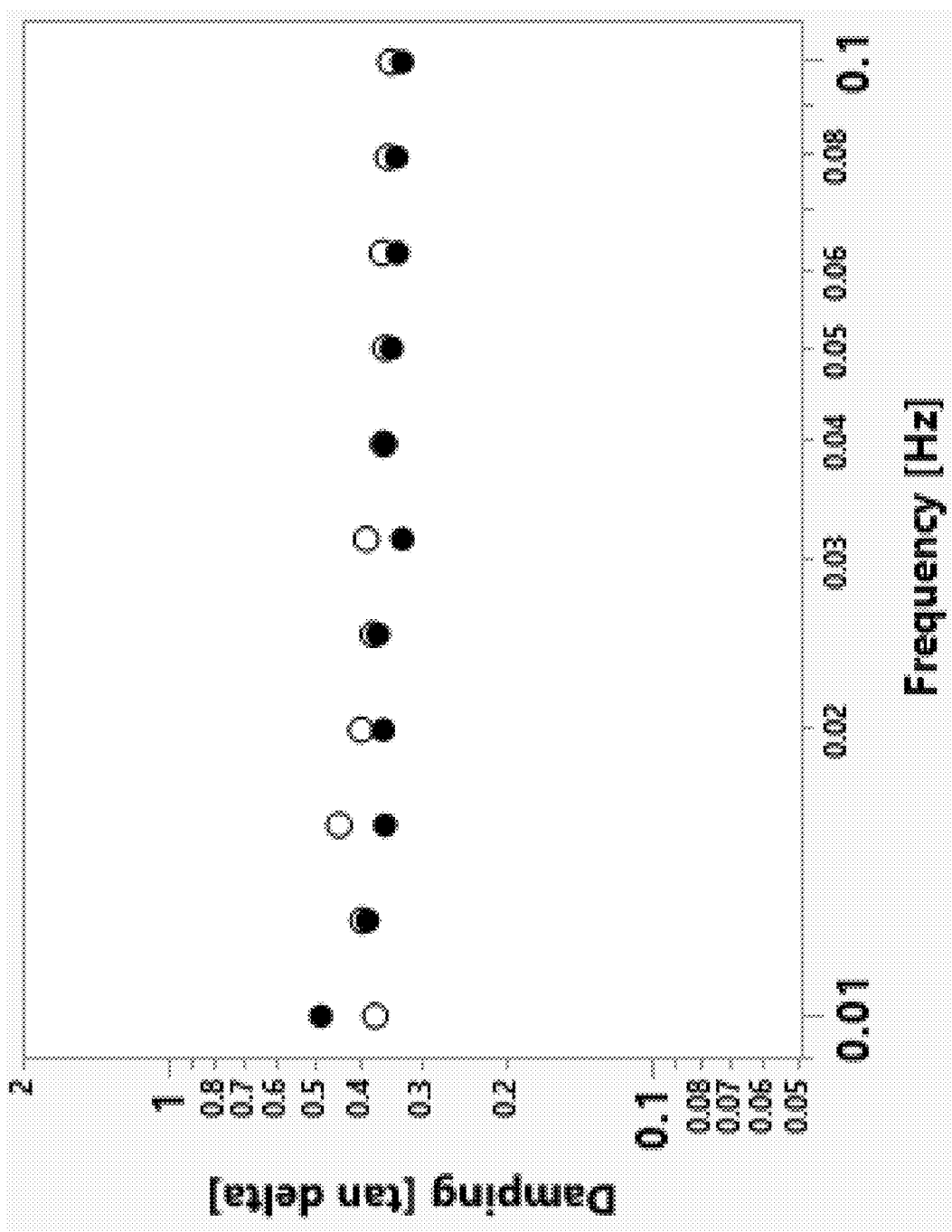

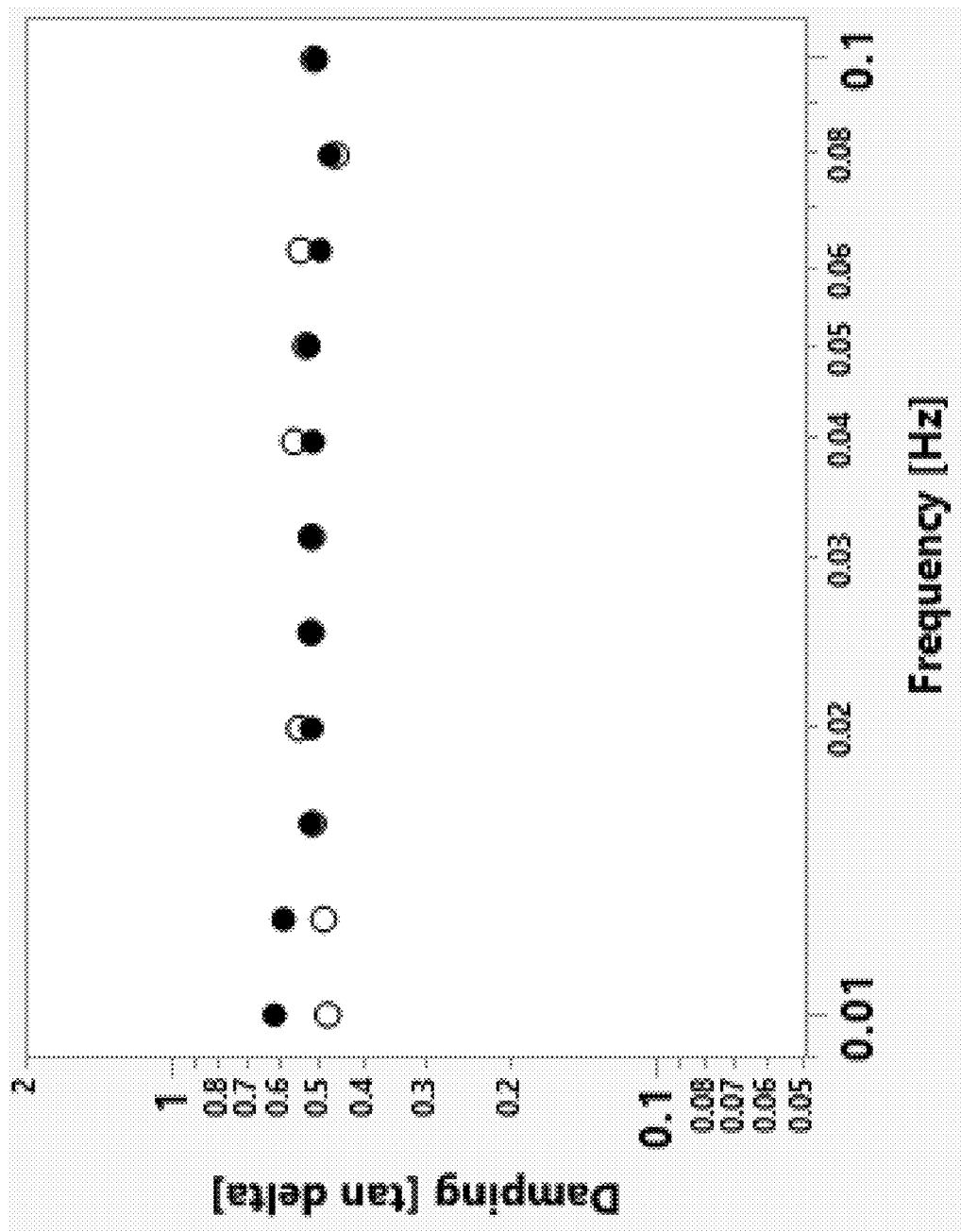
FIG. 5D Sample 4

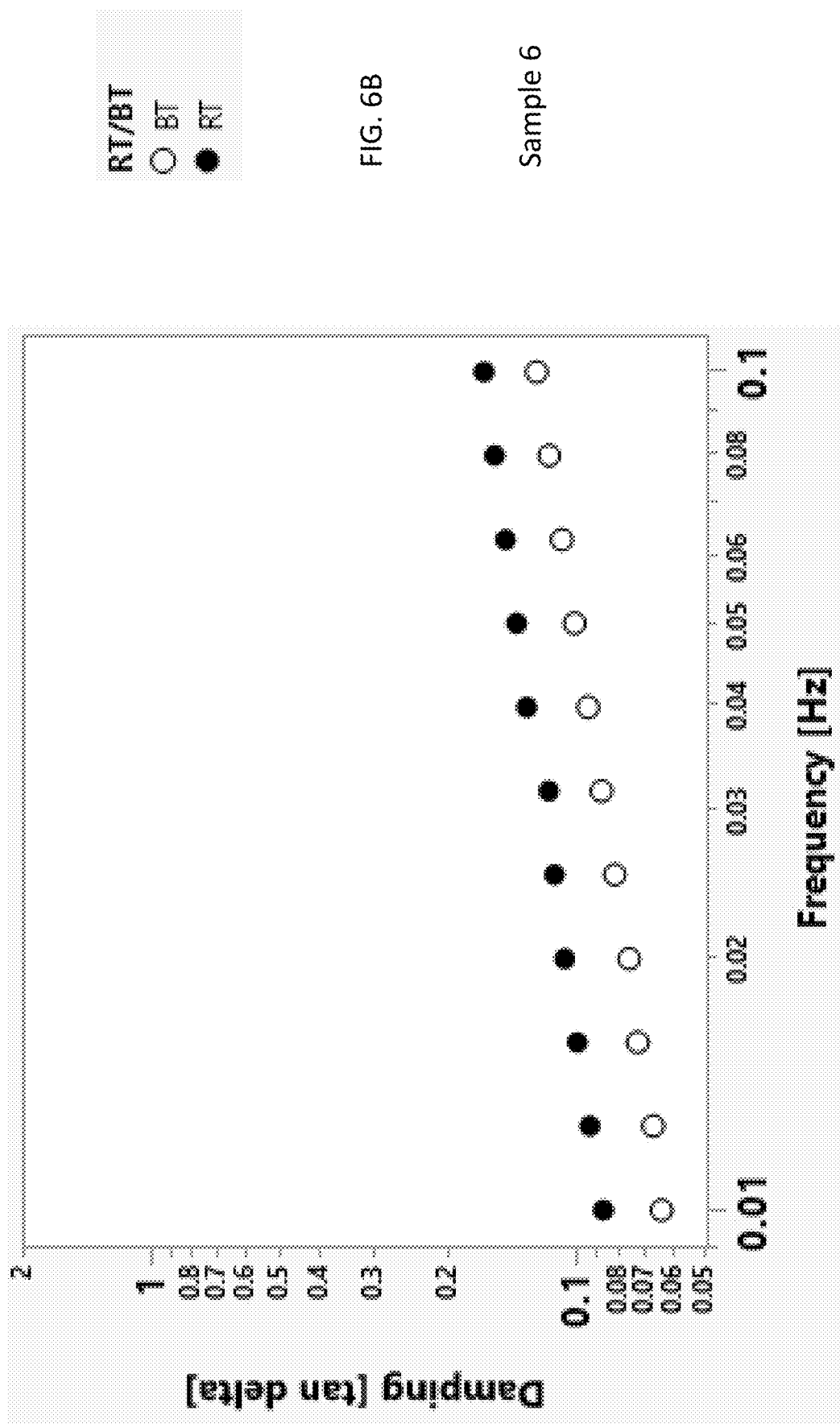
FIG. 6B Sample 6

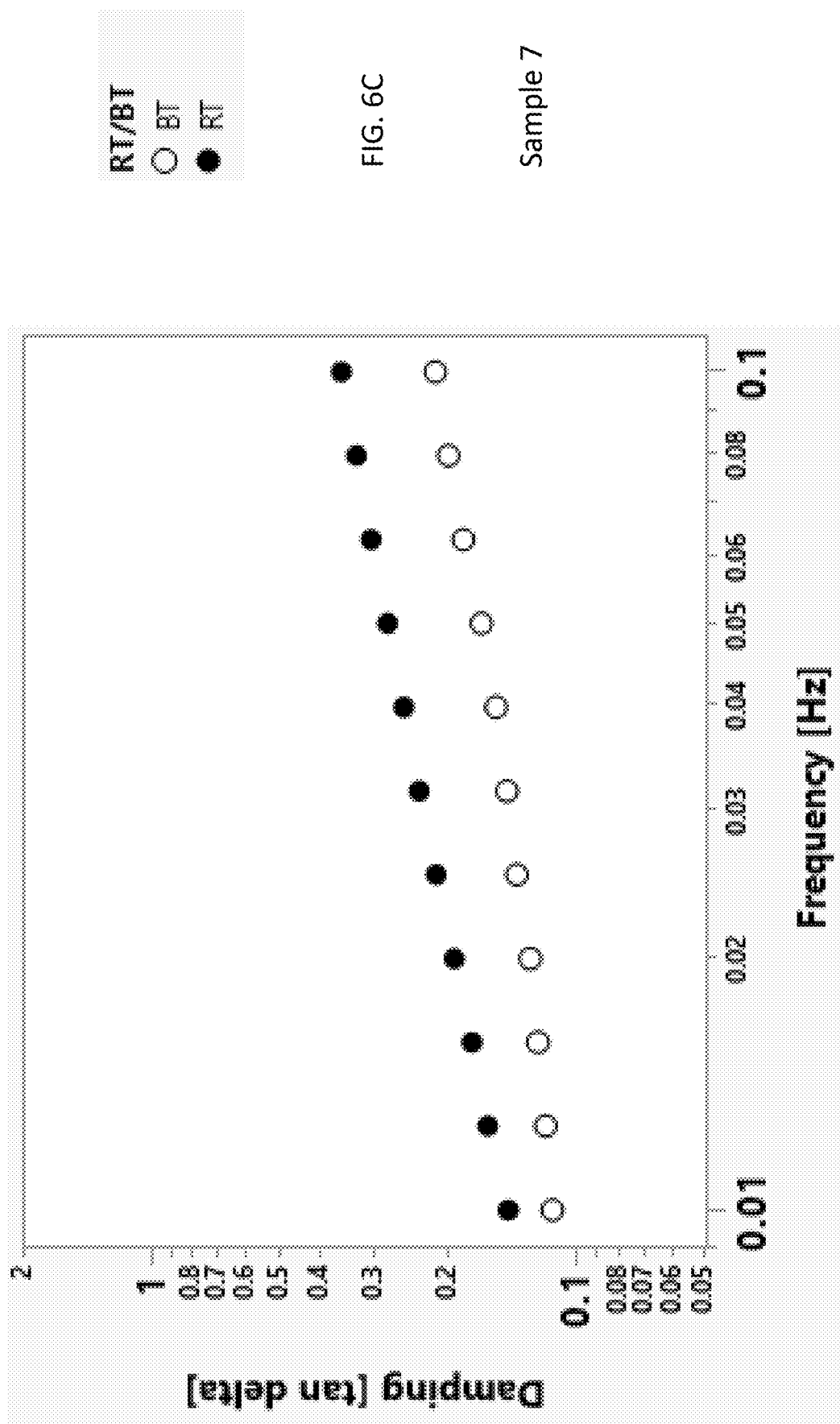

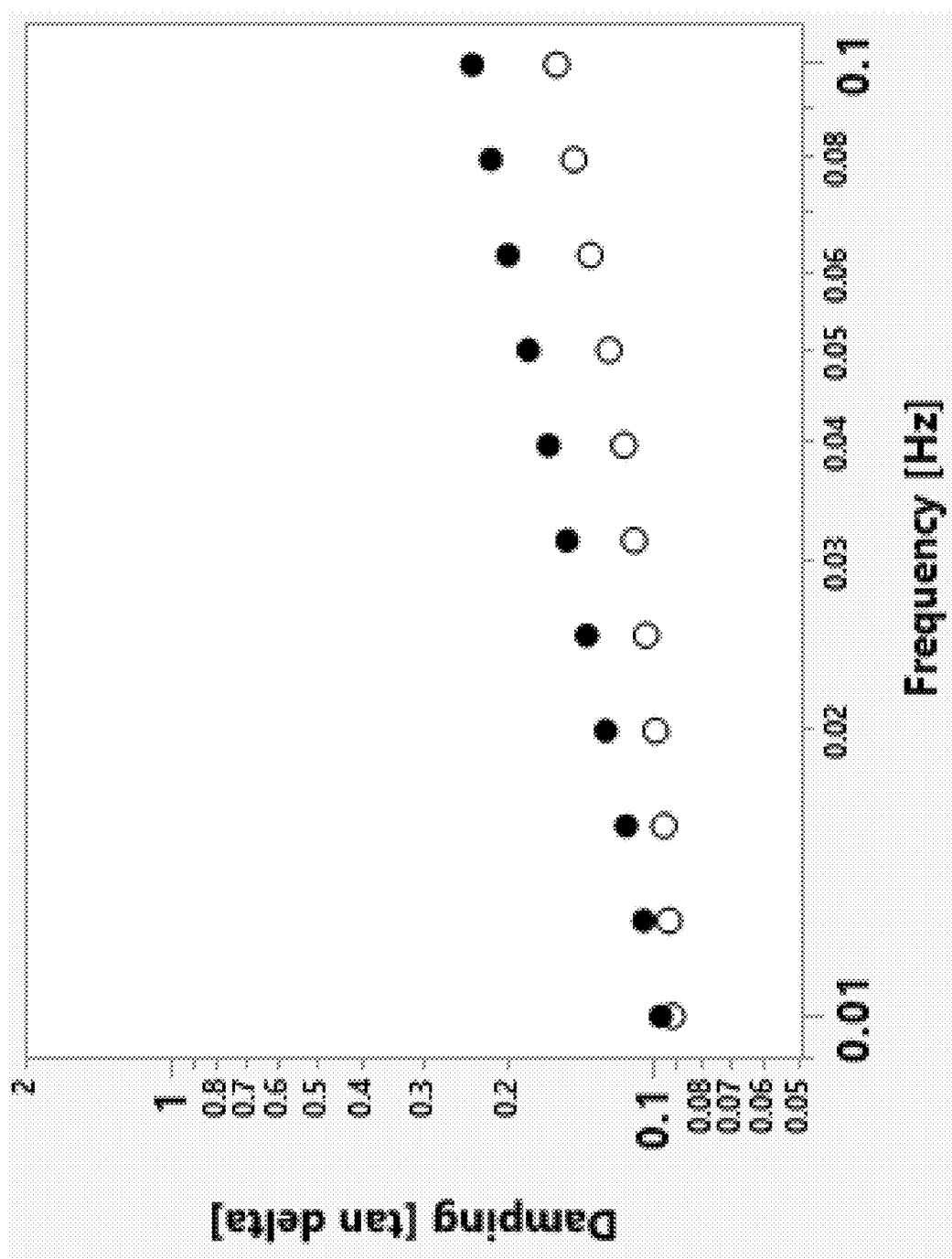
FIG. 6D Sample 8

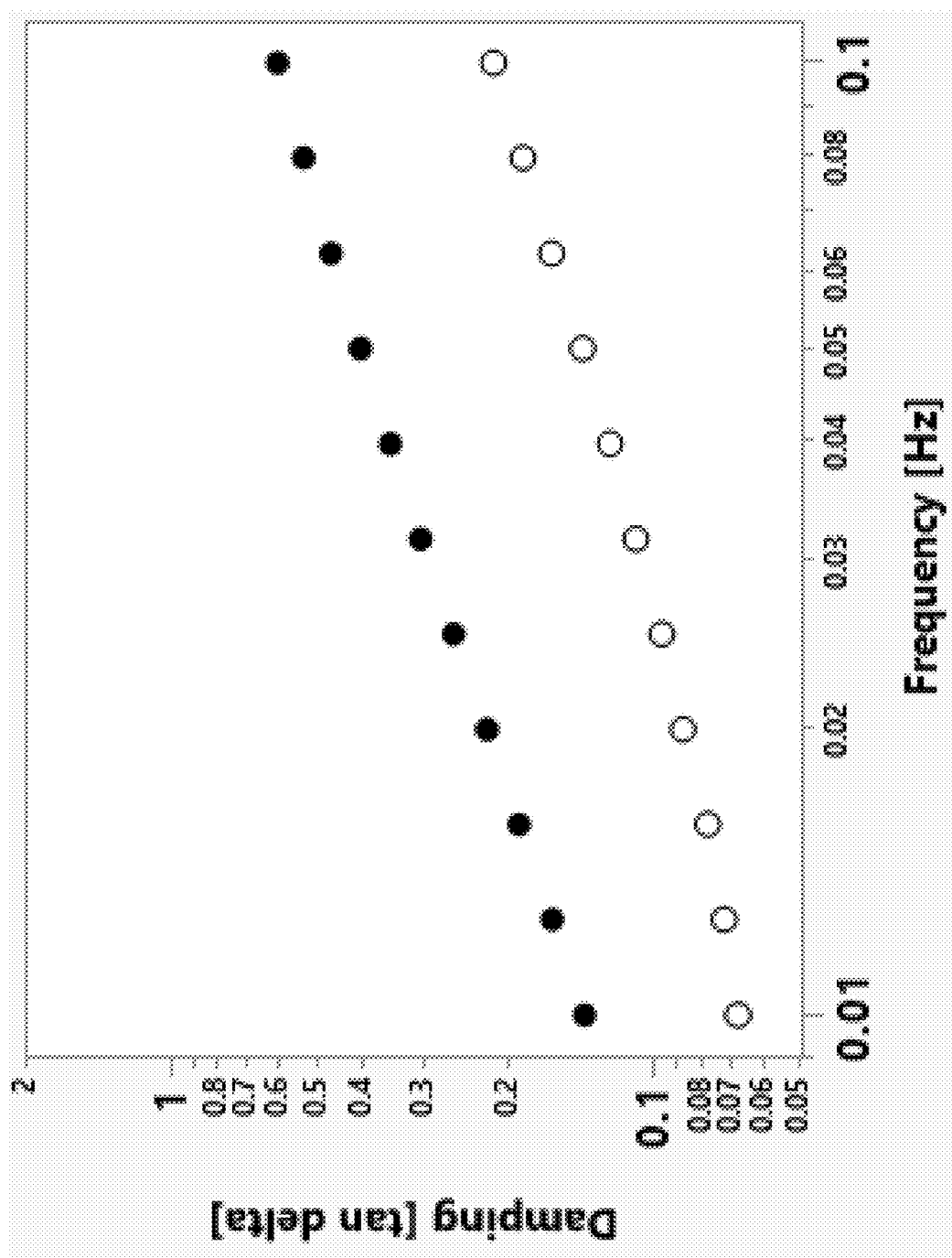
FIG. 6E Sample 9

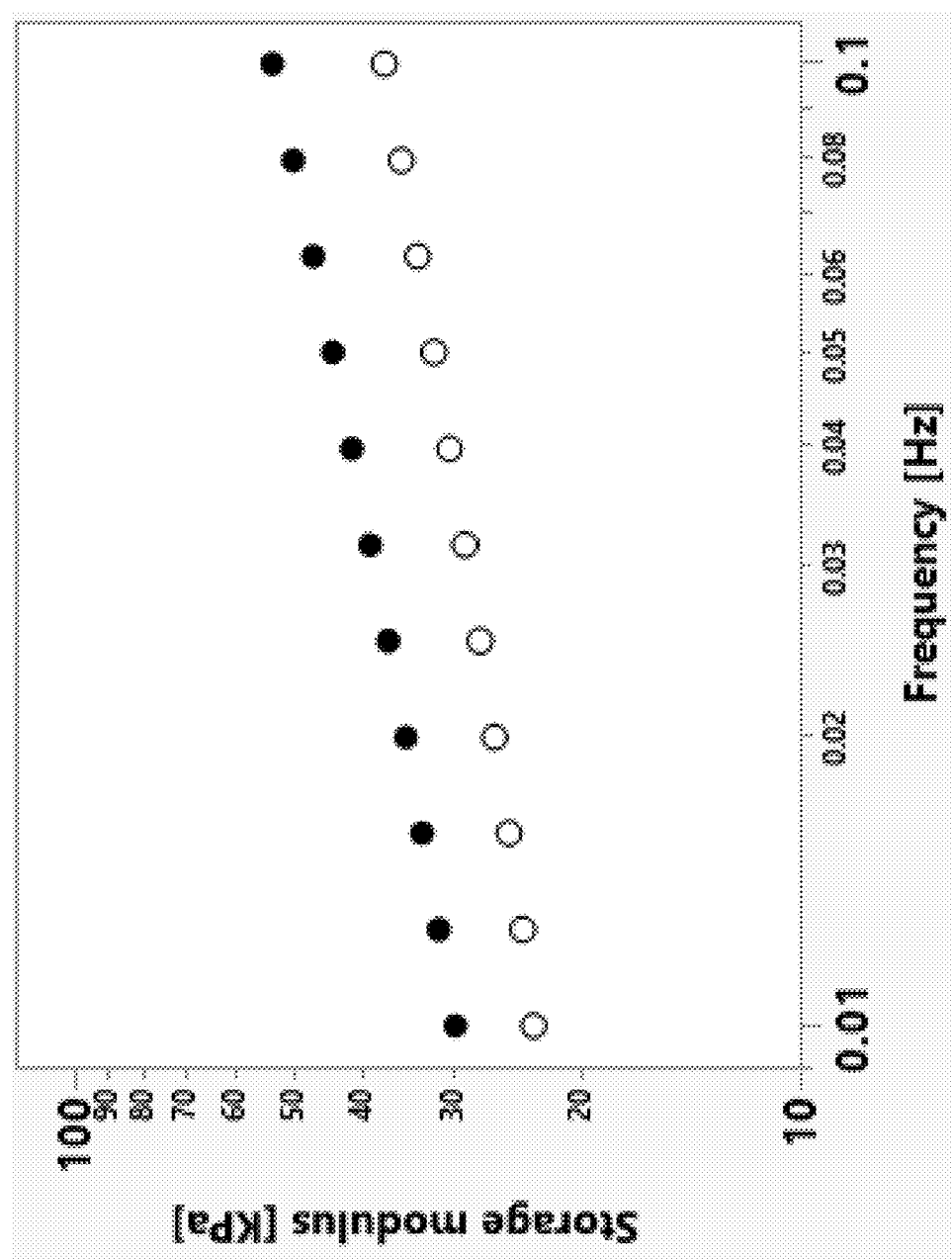
FIG. 7A Sample 1

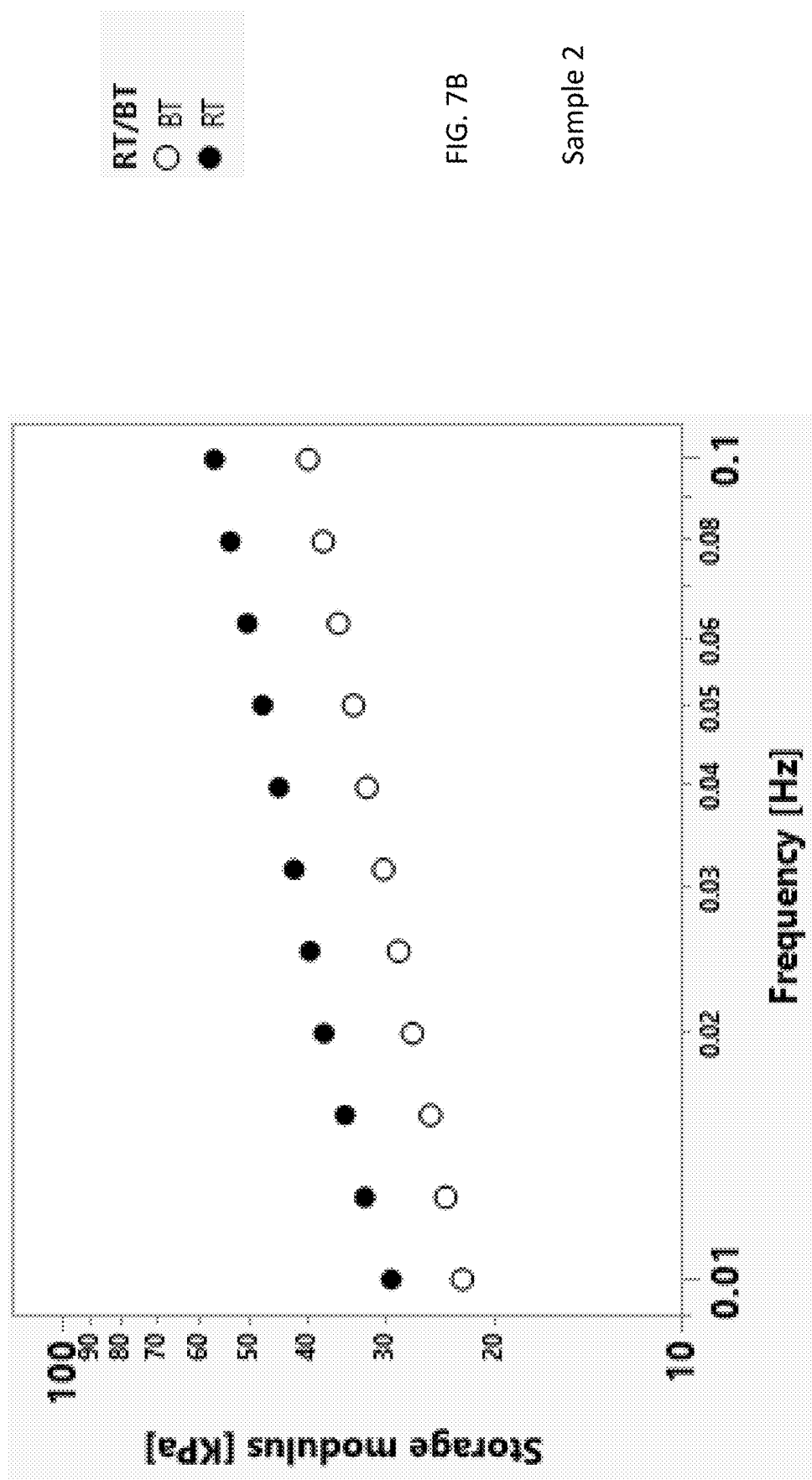

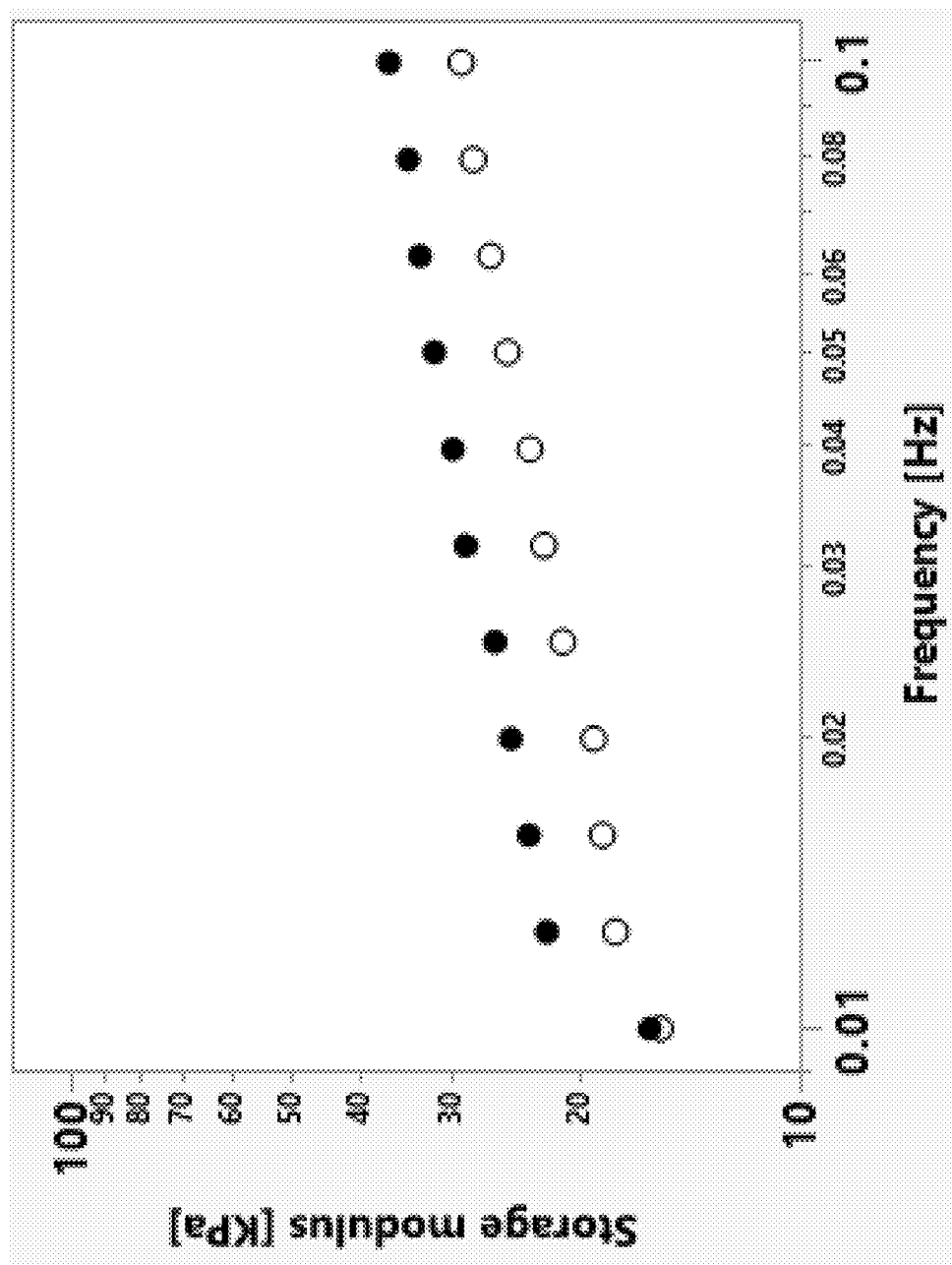
FIG. 7C Sample 3

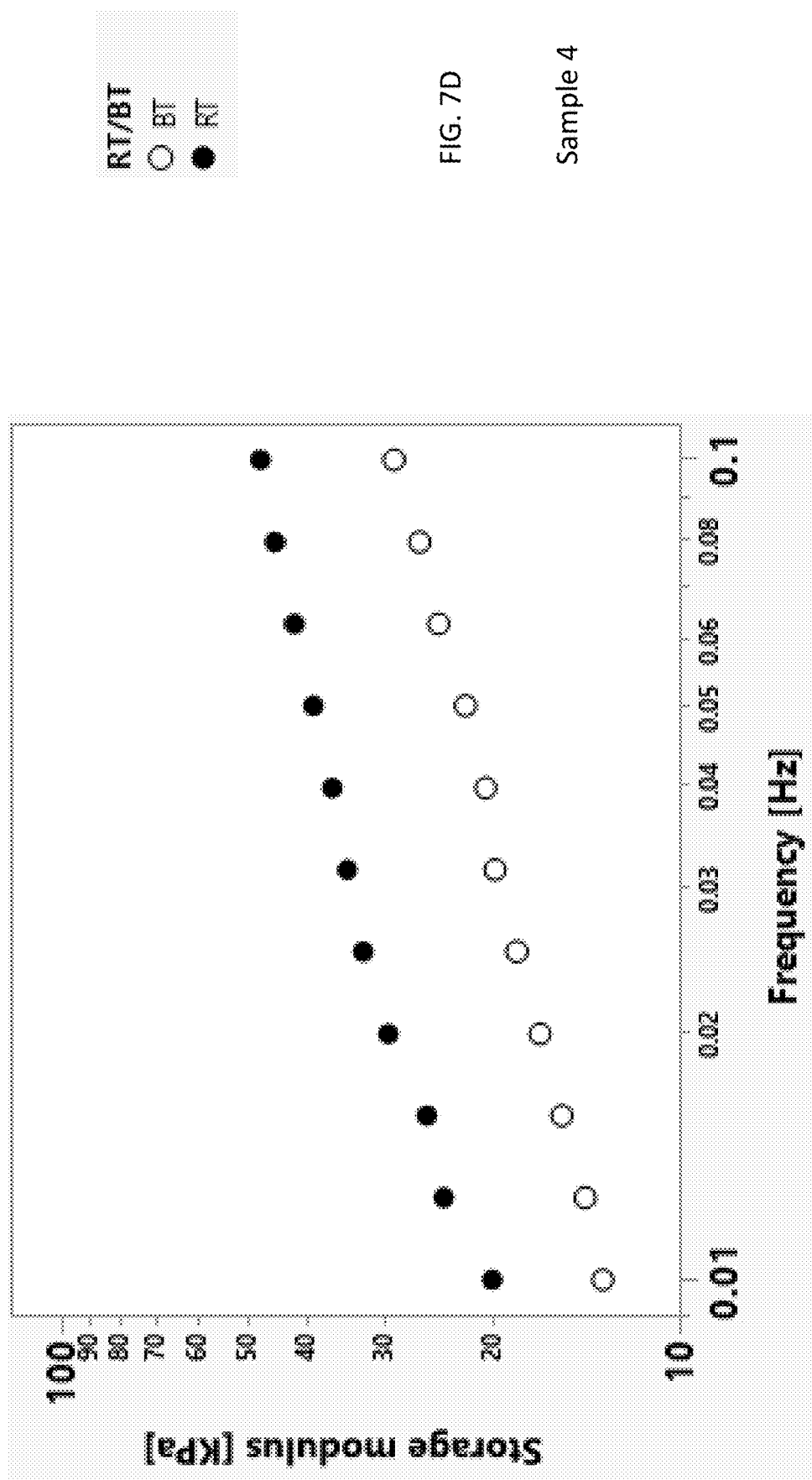
FIG. 7D Sample 4

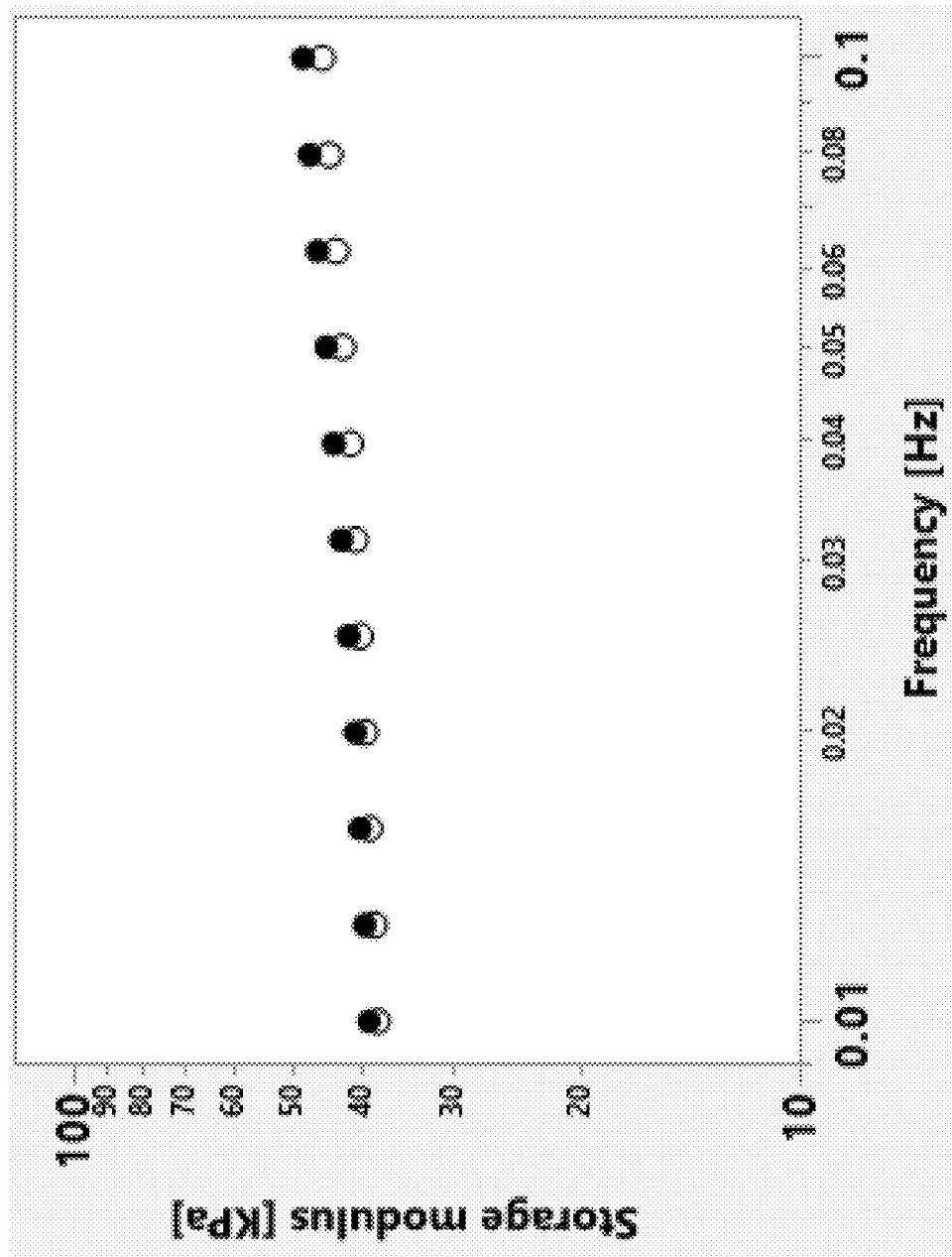
FIG. 8A Sample 5

Sample 6

Sample 7

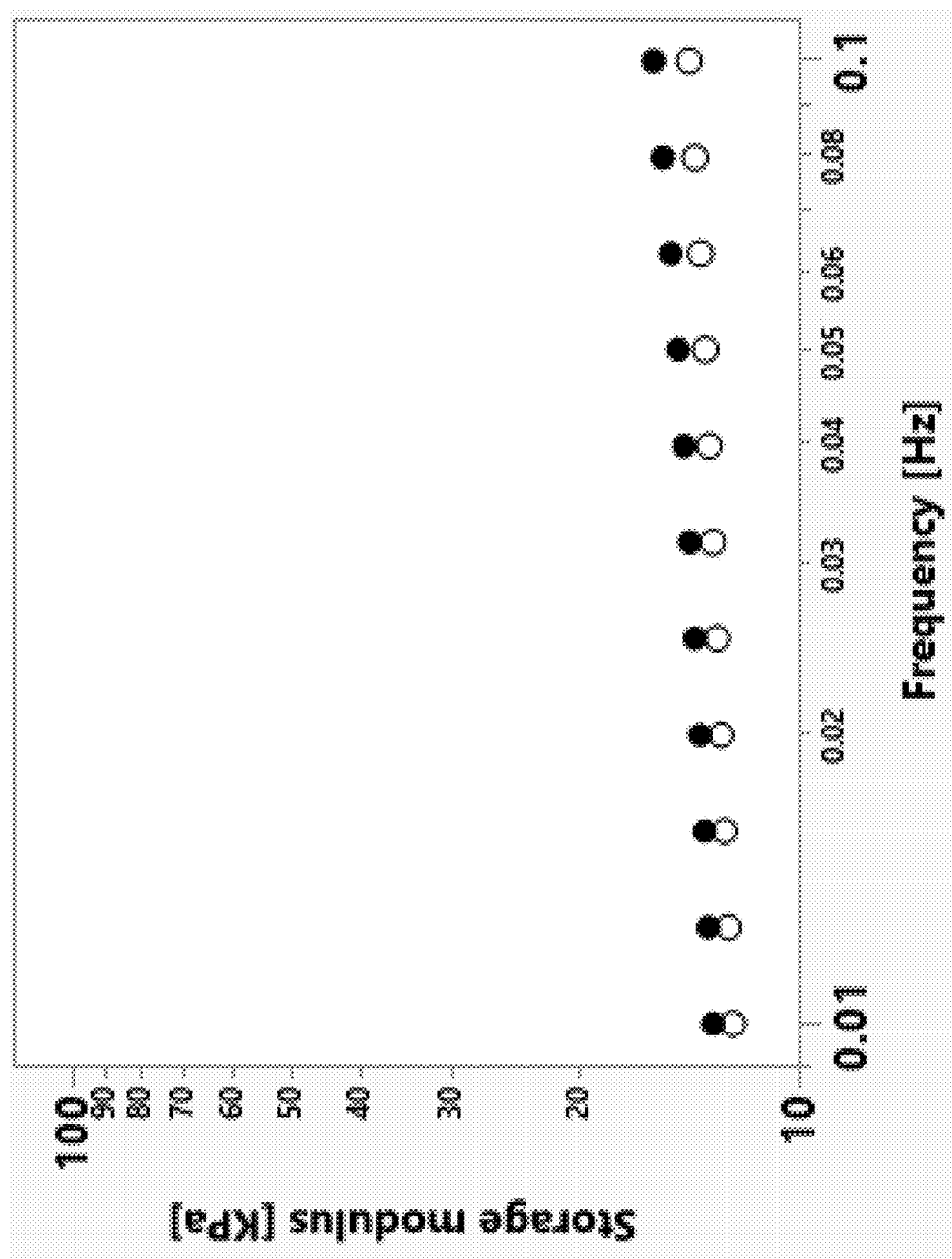
FIG. 8D Sample 8

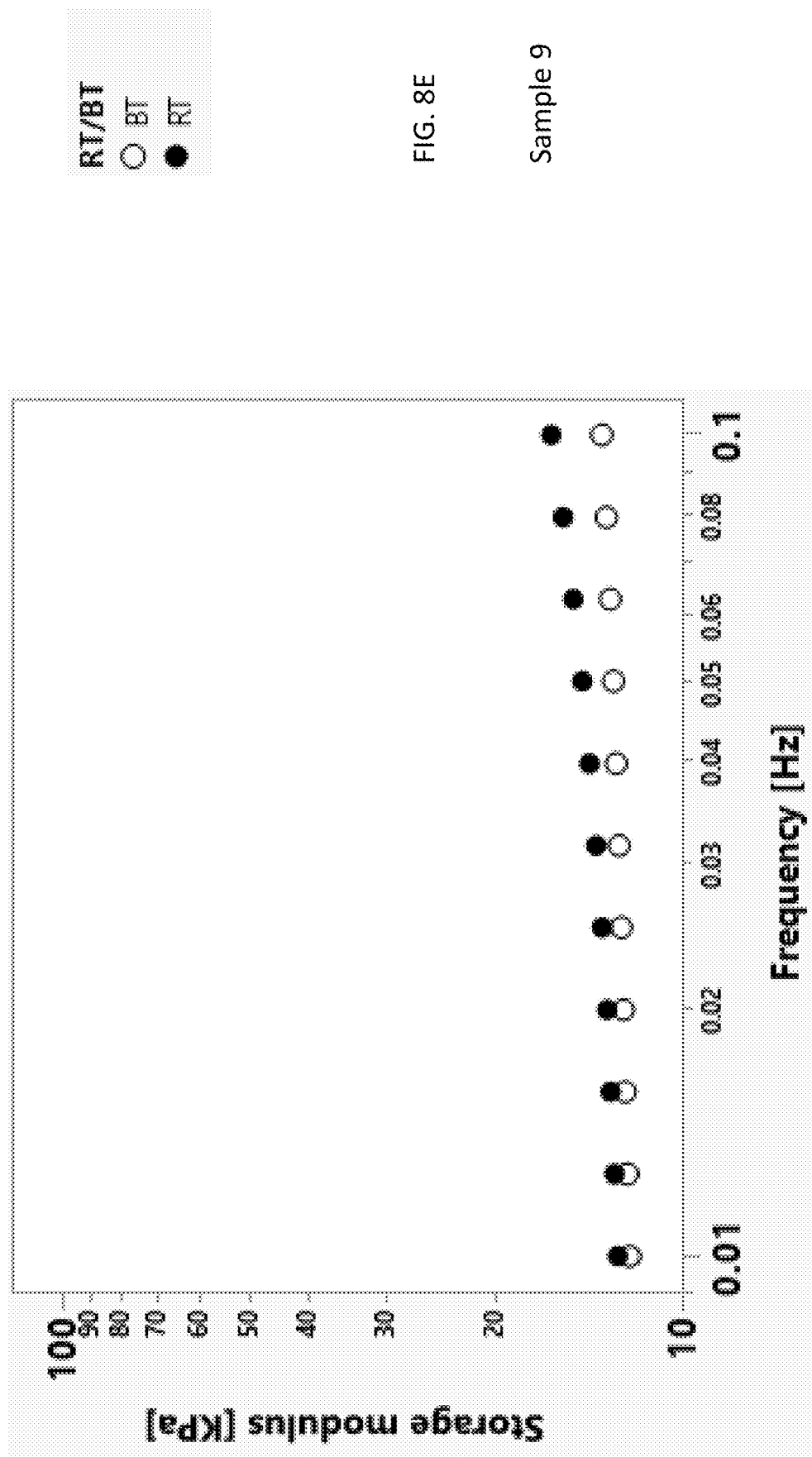
FIG. 8E Sample 9

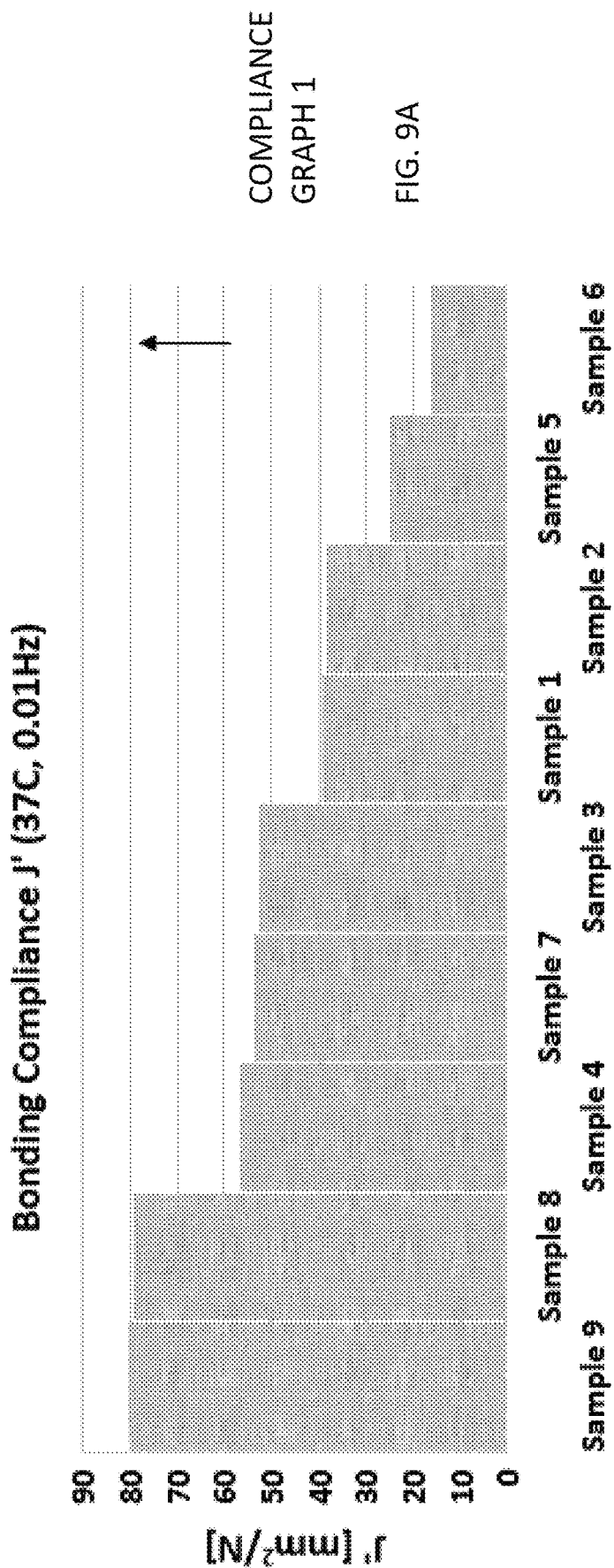
FIG. 9A COMPLIANCE GRAPH 1

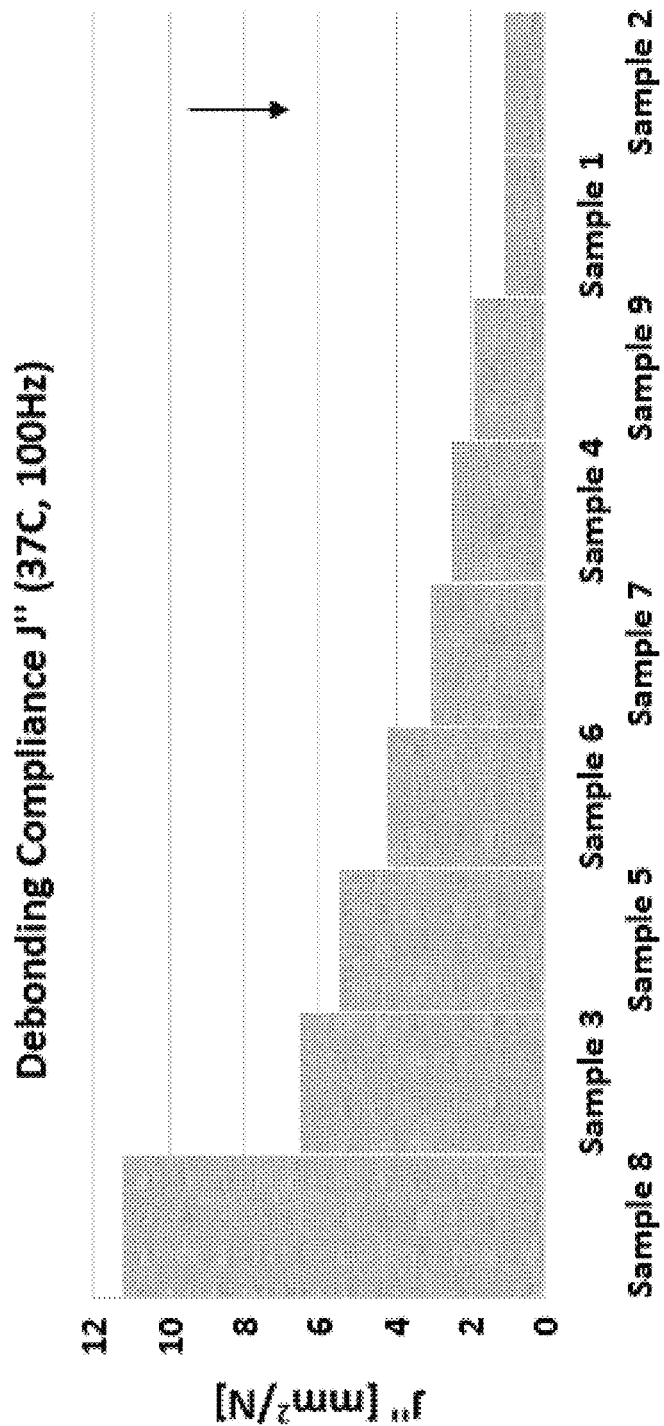
FIG. 9B COMPLIANCE GRAPH 2

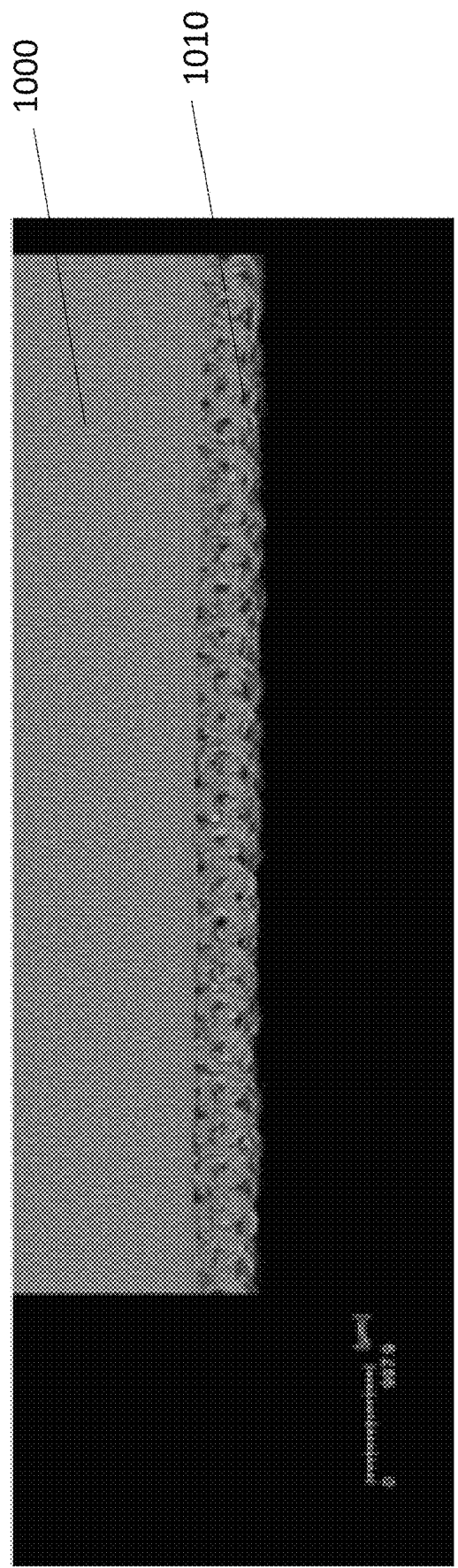
FIG. 10A Sample 1

Sample 7

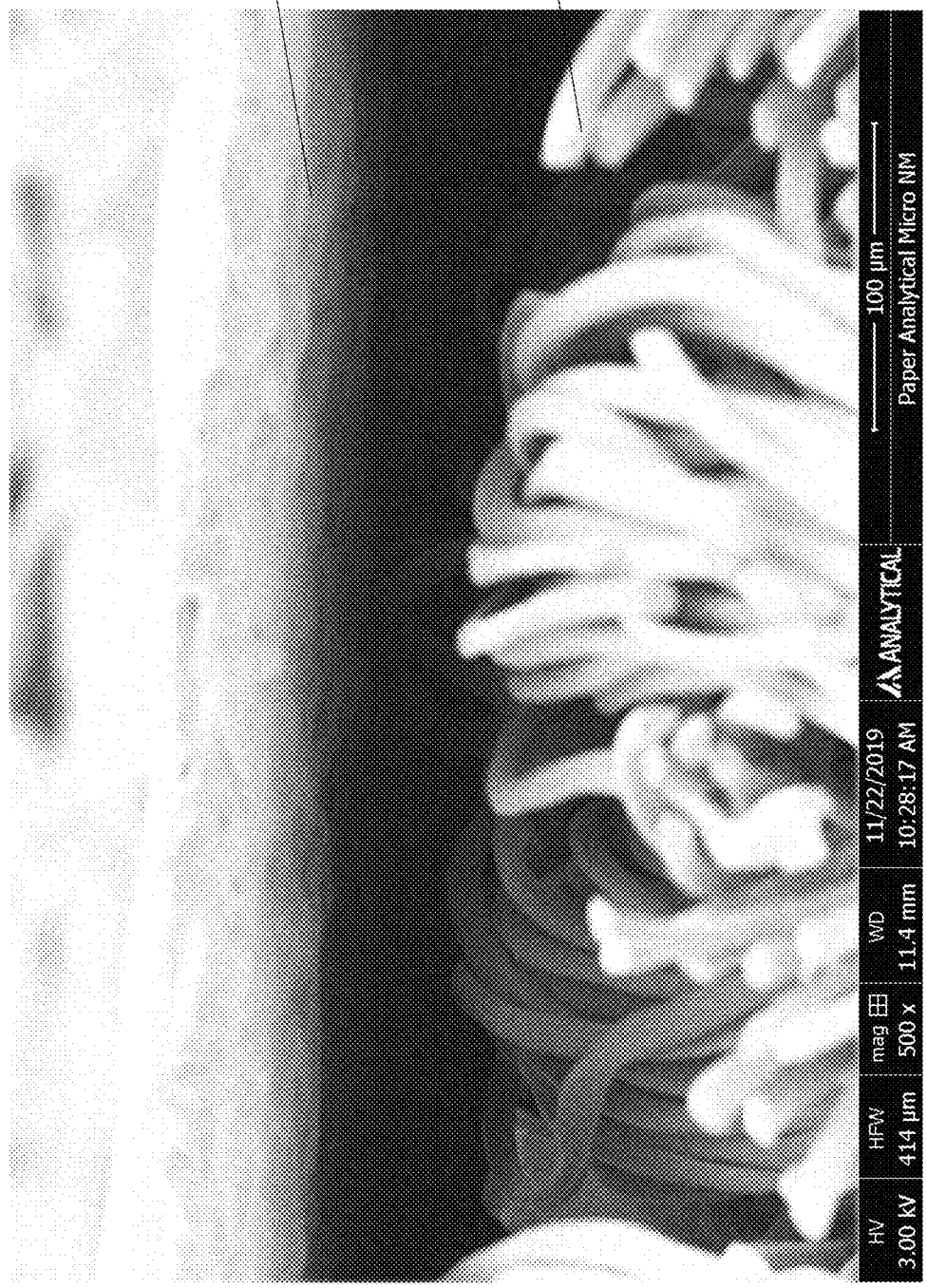
FIG. 11C Sample 7

Sample 7

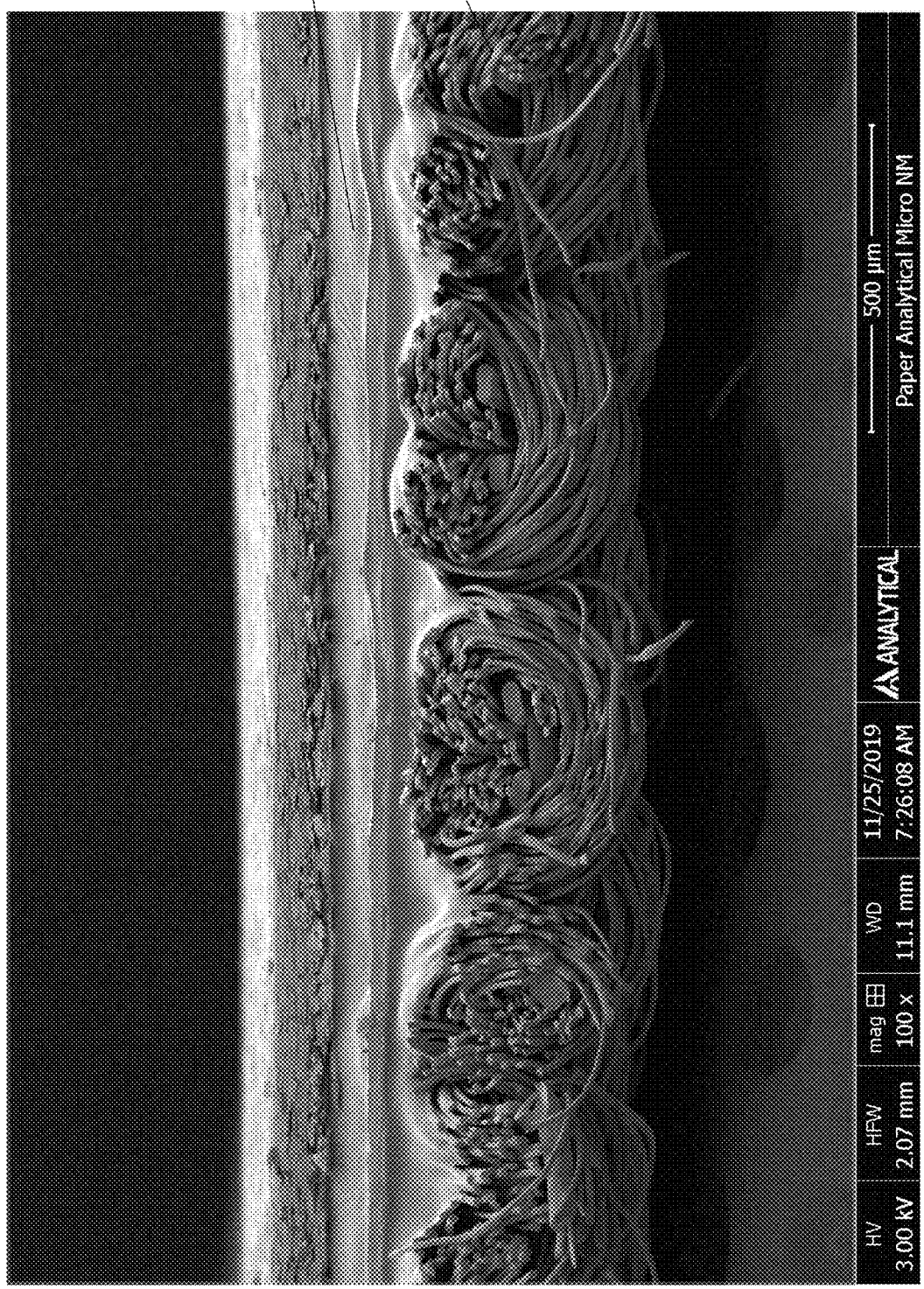
FIG. 12A — Sample 4

Sample 4

Sample 4

Sample 4

ADHESIVE FOR AN ABSORBENT ARTICLE

FIELD OF THE INVENTION

The present invention pertains to an improved adhesive for fastening a disposable absorbent article to an article of clothing, particularly underwear.

BACKGROUND OF THE INVENTION

Feminine hygiene articles are widely used to absorb menstrual fluid, urine, and other liquid insults. In many instances, feminine hygiene articles are donned by attaching the article to underwear of the user. The use of adhesives for securing feminine hygiene articles to undergarments for personal hygiene is well known in the art. In general, these adhesives are termed panty-fastening-adhesives, position fastening adhesives or positioning adhesives. For the sake of convenience, hereafter collectively termed "PFA."

PFA's play an important role in ensuring that the wearer is adequately protected and that the user has a good usage experience. There are essentially three main responsibilities for the PFA of the feminine hygiene article. First, the PFA should be strong enough to attach the feminine hygiene article to the undergarment at an initial attachment stage. However, this can prove to be more difficult than initially thought. Users of these articles tend to not apply very much pressure to the feminine hygiene article during initial application due to hygienic concerns, e.g. less product touches equals less contamination. The low amount of application pressure can cause the absorbent article to lack good attachment during the initial application. This problem can be exacerbated by the fact that some feminine hygiene articles, e.g. adult incontinence pads, comprise elastic barrier cuffs. The elastic forces in the cuffs can act to pull the feminine hygiene article away from the underwear of the user.

Another problem that plagues the initial application of the feminine hygiene article to the underwear is that users tend to stretch their undergarment prior to application to create a flatter surface for adhering the feminine hygiene article to. This stretching can cause an immediate shear on the adhesive. This shear stress on the adhesive can also negatively impact the initial adherence of the feminine hygiene article to the underwear.

Second, once applied to the undergarment, the PFA should keep the feminine hygiene article in place. The user of the feminine hygiene article will typically not be stationary for the entire time that they are wearing the feminine hygiene article. As such, the PFA should be strong enough to hold the feminine hygiene article in place regardless of the movement of the user and the user's undergarments. Failure to do so, could result in an increased bunching of the article which can lead to discomfort for the wearer along with an increased likelihood of leakage.

Third, the removal of the feminine hygiene article from the undergarment also plays an important role in how the feminine hygiene article will be perceived by the user. For example, in order to accommodate the first and second responsibilities above, a manufacturer may try to utilize higher amounts of PFA on the article; however, such applications may also result in consumer negatives. For example, higher amounts of PFA can lead to product tearing and adhesive residues left on the undergarment during removal. Adhesive residues left on the undergarment post removal of the article can create a negative image in the user's mind regarding the feminine hygiene article.

There are additional considerations to keep in mind when trying to pick the appropriate PFA to utilize on the feminine hygiene article. For example, the material of the undergarment can impact how a PFA reacts regarding the above three responsibilities. Two popular types of material utilized in undergarments include cotton (natural) and microfiber (synthetic). Some commercially available PFA's can perform the previously mentioned three functions rather well with cotton underwear, while they usually do not perform as well in the context of microfiber undergarments.

So, what is needed is an absorbent article having an improved PFA which can provide good initial attachment, stay in place protection, and good removal characteristics, for a variety of undergarment materials including cotton, microfiber, and the like. The absorbent articles of the present disclosure can alleviate one or more of the problems associated with commercially available absorbent articles.

SUMMARY OF THE INVENTION

Absorbent articles of the present disclosure can offer good attachment to an undergarment, sufficient adhesion during the complex movements of a wearer to provide good stay in place characteristics, and good removal characteristics over that of conventional absorbent articles.

In one example, the present disclosure pertains to a method of making a disposable absorbent article having a wearer-facing surface and a garment-facing surface, a front end region, a back end region, and a central region disposed between the front end region and the back end region. The method comprises the steps of: obtaining a topsheet; obtaining a backsheet; obtaining an absorbent system; combining the topsheet, backsheet, and absorbent system such that the absorbent system is disposed between the topsheet and the backsheet, and joining the topsheet and the backsheet together outboard of the absorbent system; obtaining pre-formed adhesive portions; and attaching one side of the pre-formed adhesive portions to the backsheet.

In another example, the present disclosure pertains to a disposable absorbent article comprising: a longitudinal centerline, a transverse centerline generally perpendicular to the longitudinal centerline, a wearer-facing surface and an opposing garment-facing surface, a front end region, an opposing back end region, and a central region disposed between the front end region and the back end region. The absorbent article further comprises: a topsheet; a backsheet; an absorbent system disposed between the topsheet and the backsheet; and a plurality of pre-formed adhesive portions disposed on the garment-facing surface, wherein the absorbent article exhibits a peel force of at least 1.0 N, about 1.1 N or about 1.2 N, in accordance with the Peel Force test, and leaves no residue in accordance with the Adhesive Residue test method.

BRIEF DESCRIPTION OF THE DRAWINGS

FIGS. 5A-5D are graphs showing the tan delta—1 values for adhesive Samples 1-4, respectively, at two different temperatures, i.e. 25 degrees C. and 37 degrees C.

FIGS. 6A-6E are graphs showing the tan delta—1 values for adhesive Samples 5-9, respectively, at two different temperatures, i.e. 25 degrees C. and 37 degrees C.

FIGS. 7A-7D are graphs showing the tan delta—1 values for adhesive Samples 1-4, respectively, at two different temperatures, i.e. 25 degrees C. and 37 degrees C.

FIGS. 8A-8E are graphs showing the tan delta—1 values for adhesive Samples 5-9, respectively, at two different temperatures, i.e. 25 degrees C. and 37 degrees C.

FIG. 9A is a graph showing the bonding compliance values of the adhesives of Samples 1-9.

FIG. 9B is a graph showing the debonding compliance values of the adhesives of Samples 1-9.

FIG. 10A is a microCT image showing the adhesive of Sample 1 bonded to a portion of a microfiber undergarment.

FIGS. 11A-11D are SEM images showing a cross section of the adhesive of Sample 7 bonded to a portion of a microfiber undergarment.

FIGS. 12A-12D are SEM images showing a cross section of the adhesive of Sample 4 bonded to a portion of a microfiber undergarment.

DETAILED DESCRIPTION OF THE INVENTION

Figure 1A:
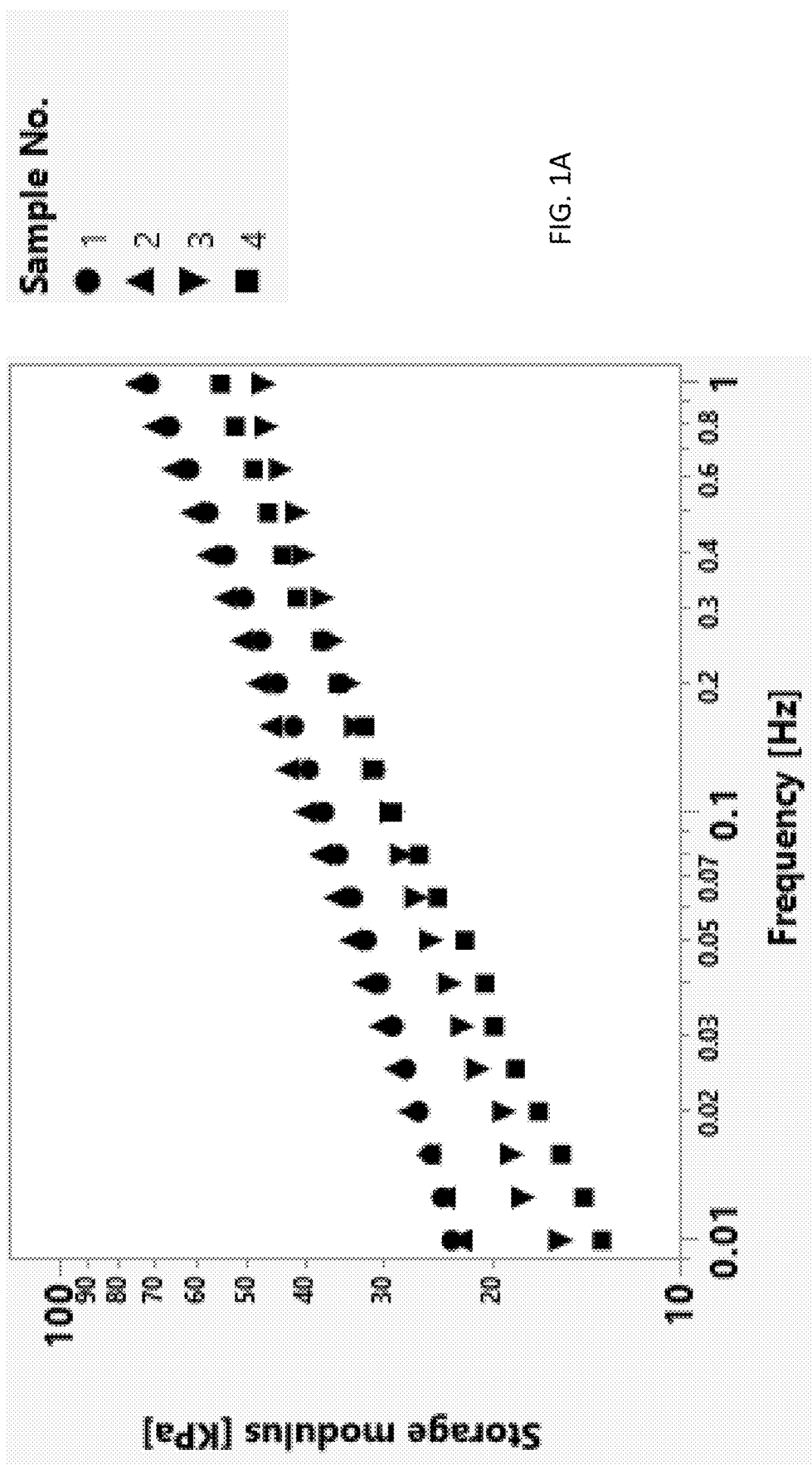
FIG. 1A is a graph showing the storage modulus—1 values for adhesive Samples 1-4 which are in accordance with the present disclosure.

As used herein, "absorbent article" refers to articles which absorb and contain body exudates or discharges such as body fluids, and is intended to include sanitary napkins, pantiliners, and incontinence pads (and other articles worn in the crotch region of a garment) as well as additional articles which are intended to be placed inside a user's undergarment and adhered thereto.

"Longitudinal," with respect to an absorbent article, refers to the direction from front-to-rear or from rear-to-front of the article from the wearer's perspective.

"Transverse," with respect to an absorbent article, refers to the direction perpendicular to the longitudinal direction, and from side-to-side of the article from the wearer's perspective.

With respect to a component of a wearable absorbent article constructed of a plurality of components, a "wearer-facing" component is the component disposed closest to the wearer's skin when the article is worn, and a "garment-facing" component is the component disposed furthest from the wearer's skin. With respect to two opposing major surfaces of a web, sheet or batt component of a wearable absorbent article, the "wearer-facing" surface is the surface facing the wearer's skin when the article is worn, and the opposing "outward-facing" surface is the surface facing away from the wearer's skin.

As noted previously, there are a myriad of considerations which are pertinent regarding the performance of PFA's. For example, as noted previously, the material of the underwear can greatly impact the performance of PFA. One of the materials that is widely used by consumers is underwear with microfiber material. Microfibers are one of the recent major developments in the fabric industry. These fibers conventionally have less than 1 denier. Microfibers have found use in especially the clothing industry, where they are used to form fabrics having unique physical and mechanical performance. Because microfibers are thinner than silk, have very good strength, uniformity and processing characteristics, they can provide a wearer with a luxurious look and feel.

Also, as noted previously, PFA's which work well with cotton undergarments, may not work so well with microfiber undergarments. This can be understood in terms of surface properties of the system composed by undergarment and adhesive and in terms of relative elasticity mismatch between underwear and pads.

This problem with absorbent article attachment to undergarments, particularly of microfiber material, is a widespread problem. Adhesive, specifically PFA failure, is one of the leading consumer complaints regarding their absorbent article use. And, as evidenced by the art, e.g. US20050256481 and US2015/0038936A1, the desire for an adhesive suitable for use with microfibers has existed for over a decade. However, to date, there is no commercially available PFA which can accommodate the three responsibilities stated previously, i.e. initial attachment, stay in place, and removal with no residue for the varied materials of underwear available to consumers.

To further complicate matters, in addition to the problems identified above, the inventors have further discovered that consumer application habits strongly impact the resulting attachment for PFA's. All PFA's require an initial pressure to flow and create a bond between the article and the undergarment. And, as noted previously, consumers tend to try to avoid touching the product during application due to hygienic concerns, thus applying very little pressure in very limited areas of the products (usually just front and wings). So, the consumer application habits tend to fall short in the creation of meaningful initial bonding with the undergarment.

Moreover, while not wishing to be bound by theory it is believed that washing habits may similarly impact the performance of PFA's. It is believed that since the introduction of washing and drying aids such as fabric softeners and dryer sheets, the performance of PFA's have been impacted. It is further believed that the decreased performance of PFA's may be negatively impacted by these washing and drying aids depositing hydrophobic active (e.g. Alky Ester Quat & Fatty Acid) in the fabric softener on the surface of the clothing.

It is further believed that the number and frequency of washes can have an impact on the ability of the PFA's to attach to the underwear, regardless of the underwear material. It is believed that this is due to the increased "fuzz" or loose fiber production by garments on their surface with increased washes. This increased "fuzz" can provide additional anchoring points for the adhesive and help create a stronger bond. However, the increased anchoring points can negatively impact the removal of the article (and its PFA) from the undergarment potentially leading to increased residual PFA left behind on the undergarment.

Despite the complexity of the problems needing to be solved, the inventors have surprisingly found several adhesives which can function as suitable PFA's and provide improvements over conventional absorbent articles.

The adhesives discovered by the inventors are not conventional in the sense that they are not used as PFA's. Instead, these adhesives have indicated uses which are vastly different than that of a PFA. These discovered adhesives may comprise pre-formed adhesive portions.

Pre-formed adhesive portions of the present disclosure differ from traditional PFA's in the sense that the pre-formed adhesive portions can be applied to a garment-facing surface of an absorbent article in solid form. Conventional PFA's are typically sprayed or coated onto the garment-facing surface. These application techniques are performed while the PFA is in a liquid or highly molten state.

These pre-formed adhesive portions may comprise double-sided tapes. Double-sided tapes may comprise a substrate, e.g. a film, a nonwoven, a woven, a foam, combinations thereof, comprising adhesive on either side of the substrate. Pre-formed adhesive may also be configured sans a substrate therein. In such constructions, the adhesive portions may simply be a solid block of adhesive. Pre-formed adhesives are discussed in additional detail regarding FIGS. 15A-15D.

These adhesives of the present disclosure can be applied to a garment-facing surface of the absorbent articles as part of an absorbent article manufacturing process, e.g. cut and place operation. Still in another example, the adhesive can be placed upon the garment-facing surface of the absorbent article by hand. Or, the adhesive may be placed upon the garment-facing surface via a blend of manufacturing process and by hand. Still in other processes, the absorbent article manufacturer may provide the garment-facing surface of the absorbent article to an adhesive supplier, and the adhesive supplier may place the double-sided tape on the garment-facing surface.

The adhesives of the present disclosure may be applied in a front end region and a back end region of the absorbent article. A central region, disposed between the front end region and the back end region, can also have the adhesive applied thereto; however, the inventors have found that placement of the adhesive in the central region is not necessarily required. For the sake of clarity, it is worth describing the boundaries of the end regions and central region. The front end region, back end region and central region may each comprise about one third of the overall length of the absorbent article in a completely flattened state.

As noted previously, the inventors have surprisingly found that the adhesives of the present disclosure, when placed in the end regions, with or without adhesive in the central regions, that these adhesives can provide improved initial attachment, improved stay in place and/or improved removal characteristics over conventional PFAs. Regarding the coverage of the adhesive in the end regions, the adhesive may have a length which is at least 15 percent of a length of the end regions, in at least about 30 percent, or in at least about 40 percent, specifically reciting all values within these ranges and any ranges created thereby. For example, the front end region may comprise a length generally parallel to a longitudinal centerline of the absorbent article.

The length of the front end region may range from about 30 mm to about 170 mm. The adhesive in the front end region can have a length, generally parallel to the longitudinal centerline of the absorbent article which is from about 15 percent of the length of the front end region to about 93 percent, specifically reciting all values within these ranges and any ranges created thereby. In some specific examples, the length of the adhesive in the front end region can be from about 25 mm to about 100 mm, from about 25 mm to about 90 mm or from about 25 mm to about 50 mm, specifically reciting all values within these ranges and any ranges created thereby. In one specific example, the adhesive in the front end region can have a length which is about 30 mm. The adhesive for the back end region can be configured similar to that of the front end region.

Additionally, the length of the adhesive in the front end region or the back end region can begin adjacent end edges of an absorbent core. Specifically, it is believed that the placement of the adhesives of the present disclosure in the front end region and back end region can impact how the adhesive performs in the context as a PFA. It is believed that the closer to the end edges of the absorbent core the adhesive is placed, the better performing the adhesive will be. For example, the adhesive in the front end region and back end region may comprise adhesive which is disposed 3 mm or less from an end edge of the absorbent core or 2 mm or less from an end edge of the absorbent core.

Similarly, it is believed that when the adhesive is disposed adjacent longitudinal sides of the absorbent core, the better the adhesive will perform in the context as a PFA. For example, the adhesives of the present disclosure may be disposed 3 mm or less from a longitudinal side edge of the absorbent core or 2 mm or less from the longitudinal side edge of the absorbent core.

It is worth noting that the adhesives of the present disclosure can have any suitable caliper. However, as the caliper increases, complexities in manufacturing may occur. Additionally, with an increase in caliper, the user may be able to feel variable pressure being applied to the skin and/or the variable pressure may be applied to the outer garment such that an imprint of the adhesive may be visible on the outer garments of the wearer. So, in some instances, the caliper of the adhesives of the present disclosure can have a thickness which is 1 mm or less, specifically reciting all values within this range and any range created thereby.

Where the adhesive has a caliper which is greater than 1 mm, the thickness of the adhesive may be reduced. For example, mechanical means such as skiving, cutting, slicing, the like, etc., may be utilized to reduce the caliper of the adhesive portions. Re-casting of the adhesive portions is also possible.

The inventors have also discovered that the rheological and mechanical behavior of these adhesives can play a role in its performance as a PFA. Adhesives applied to the garment-facing surface of the absorbent article can have the rheological and mechanical properties described herein. And, such adhesives can provide improved performance over that of conventional PFAs as described herein.

One criterion associated with the rheology of adhesives is the damping factor. In order to accommodate the initial application, stay in place, and removal requirements mentioned previously, the damping factor can be measured at least at two different frequency ranges. This has to do with the different time scales involved in the different phases of the adhesive's life. During application and successive initial wear, the adhesive has a very long time to be able to flow and create intimate contact with the fibers of the garment, promoting bond strength. This time scale is usually in the order of 1 s to 100 s or higher for which it then follows that for the initial placement and stay in place criteria, the damping factor (tan delta—1) can be between about 0.01 Hz (=1/100 s) to about 1 Hz=(1/1 s). As noted, the tan delta—1 measurement can be important for the initial application as well as the stay in place criteria. Tan delta—1 is measured as described herein at a frequency of between 0.01 and 1 Hz at 37 degrees C. It is believed that 37 degrees C. more closely mimics body temperature as well as the conditions under which the adhesive will perform.

Without wishing to be bound by theory, it is believed that a high value of tan delta—1 (coupled with a low value of the storage modulus—1 (G' 1), as disclosed herein) is conducive to a higher value of compliance. The higher value of compliance in turn promotes a better conformability of the adhesive to the surface of the undergarment and a more intimate contact, leading to a stronger bonding of the double-sided tape to the undergarment. The compliance value is discussed in additional detail hereafter. The ability to attach to a greater number of fibers of the underwear—regardless of material, e.g. cotton, microfiber, or the like, particularly during initial application—is believed to be a critical piece in obtaining a successful initial attachment of the absorbent article to the undergarment.

The adhesives of the present disclosure can exhibit a tan delta—1 value of between 0.28 to 1.2, between 0.28 to 1.13, or between 0.28 to 0.51, when measured over a frequency range of between 0.01 Hz and 1 Hz at 37 degrees C. in accordance with the Frequency Sweep—Oscillatory Rheometry Test Method described herein, specifically reciting all values within this range and any ranges created thereby. Additionally, these adhesives can exhibit a tan delta—1 value from between 0.28 to 0.9 at 0.01 Hz at 37 degrees C., specifically reciting all values within this range and any ranges created thereby. It is worth noting that these adhesives can exhibit the above tan delta—1 value over the entire range of 0.01 Hz to 1 Hz. So, at 0.01 Hz and at 1 Hz, the tan delta—1 value can be between 0.28 to 1.2, specifically reciting all values within this range and any ranges created thereby.

As explained heretofore, during the application and successive initial wear of an absorbent article in the underwear of a user, the adhesive can have a long time to be able to flow and create intimate contact with the fibers of the underwear. However, within the frequency range specified, there is no fixed time in which the article is applied to the undergarment—quite the opposite in fact. The application of the article to the undergarment, from a time perspective, is highly variable. And as noted, initial application is critical in establishing good adhesion between the adhesive and the underwear. So, in some forms, the adhesive can exhibit the values for tan delta—1 expressed heretofore over the entire frequency range of 0.01 Hz to 1 Hz.

As mentioned previously, the absorbent article, once applied to the undergarment, can provide the adhesive with a variable amount of time to bond to the undergarment. The inventors have surprisingly found that where expediency of the bonding of the adhesive to the undergarment is desired, the relaxation time of the adhesive may be of import. Additionally, the inventors have found the temperature at which the relaxation time is measured can greatly impact this criterion. For example, the relaxation time of an adhesive measured at 25 degrees C. can be substantially longer than the relaxation time of the same adhesive measured at 37 degrees C.

During application of the absorbent article, it is believed that there is a mix of these temperatures, or temperatures therebetween occurring. For example, when the absorbent article is first applied to the undergarment, the adhesive and the absorbent article are likely to be closer to room temperature, i.e. 25 degrees C. than body temperature, i.e. 37 degrees C. However, once the undergarment is re-donned, the absorbent article and the adhesive begin to increase in temperature. Eventually, the absorbent article and adhesive reach steady state near body temperature, i.e. 37 degrees C., minus a couple/few degrees. At the elevated temperature, the relaxation time of the adhesive can be substantially less than that which is measured at 25 degrees C. Adhesives of the present disclosure can have a relaxation time, at 37 degrees C., of 100 seconds or less, 30 seconds or less, or 20 seconds or less, specifically reciting all values within these ranges and any ranges created thereby.

The relaxation times for the sample adhesives disclosed in Table 1, were calculated via the formula below.

$$\tau = \int_{0.01\ Hz}^{1\ Hz} t(\omega) d\omega = \int_{0.01\ Hz}^{1\ Hz} \left( \frac{1}{\omega \tan \delta} \sqrt[2]{\tan \delta^2 + 1} \right) d\omega$$

where tan δ is tan delta—1, ω is the frequency and τ is the relaxation time.

As noted previously, the damping factor of the adhesives or the present disclosure can be important for determining the behavior of the adhesive regarding initial attachment and staying in place. However, the inventors have also found that for removal of the absorbent article from the undergarment, the damping factor at a higher frequency can also be of import, since the consumer can remove the product in a fraction of a second. A tan delta—2 value can be measured between 50 and 100 Hz at 37 degrees C. As a competing interest to the desirable attributes of an adhesive in the description of tan delta—1, the adhesives of the present disclosure can delaminate adhesively from the panty and have high enough cohesive strength to minimize the likelihood of residue on the underwear post article removal. As noted previously, adhesive residue left over from absorbent article removal can create a negative image in the mind of the user of the absorbent article brand. Adhesives of the present disclosure can exhibit a tan delta—2 value of 1.9 or less, 1.8 or less or 1.38 or less, over a frequency range of between 50 and 100 Hz at 37 degrees C., when measured in accordance with the Frequency Sweep—Oscillatory Rheometry Test Method disclosed herein, specifically reciting all values within the range and any ranges created thereby. For example, the adhesives of the present disclosure can exhibit a tan delta—2 value of between 0.25 and 1.9, between 0.25 and 1.8, or between about 0.28 to about 1.38, at a frequency of between 50 and 100 Hz at 37 degrees C., specifically reciting all values within these ranges and any ranges created thereby. Additionally, the adhesives of the present disclosure can exhibit the above tan delta—2 values over the entire range of 50 Hz to 100 Hz. So, at 50 Hz and at 100 Hz, the tan delta—2 value can be 1.9 or less, 1.8 or less or 1.38 or less, specifically reciting all values within this range and any ranges created thereby.

Another rheological criterion is a measure of the elastic stiffness of the adhesive. This metric is called the storage modulus. In order for the adhesive to stick to a surface, the adhesives of the present disclosure can have a "soft" character so that the adhesive can adapt to any discontinuities of the surface of the fibers of the undergarment to which the absorbent article is attached. This "soft" character can influence not only initial application but also the stay in place aspect of the absorbent article and its debonding.

Similar to the damping factor, the storage modulus (G') of an adhesive at a frequency range of 0.01 Hz to 1 Hz can be indicative of the "softness" of the adhesive and its ability to adapt to the substrate and generate adhesion—termed storage modulus—1. However, the storage modulus of the adhesive at a frequency range of 50 Hz to 100 Hz can be an important contributor of both adhesion and cohesive strength of the adhesive upon removal of the article—termed storage modulus 2. This adhesion and cohesive strength can minimize the likelihood of residue left behind on the undergarment post removal of the absorbent article. And, similar to the damping factor at the two different frequency ranges, the storage modulus—1 criterion and the storage modulus—2 criterion can be competing interests. As the former is low to accommodate better adhesion during application and the latter is high to accommodate the cohesive nature of the adhesive, storage modulus—1 and storage modulus—2 can be challenging to accommodate in a single adhesive.

Adhesives of the present disclosure can exhibit a storage modulus—1 value of less than 85 kPa at a frequency of between 0.01 to 1 Hz at 37 degrees C., 74 kPa or less or 57 kPa or less, specifically reciting all values within this range and any range created thereby. For example, the adhesives of the present disclosure can exhibit a storage modulus—1 value of between 1 kPa and 84 kPa, between 3 kPa and 74 kPa, or from 12 kPa to 57 kPa, at a frequency of between 0.01 and 1 Hz at 37 degrees C., specifically reciting all values within these ranges and any ranges created thereby. In conjunction with the foregoing or independently thereof, these adhesives can exhibit a storage modulus—1 value of between 5 kPa and 84 kPa, between 5 kPa and 80 kPa, or between 5 kPa and 74 kPa, at 1 Hz at 37 degrees C., specifically reciting all values within these ranges and any ranges created thereby. In conjunction with the foregoing or independently thereof, these adhesives can also exhibit a storage modulus—1 value of between 1 kPa and 50 kPa, between 1 kPa and 40 kPa, or between 1 kPa and 30 kPa at 0.01 Hz at 37 degrees C., specifically reciting all values within these ranges and any ranges created thereby.

Regarding the storage modulus—2 value, adhesives of the present disclosure can exhibit a storage modulus—2 value of 40 kPa or greater, 73 kPa or greater, or 146 kPa or greater, between 50 and 100 Hz at 37 degrees C. in accordance with the Frequency Sweep—Oscillatory Rheometry Test Method disclosed herein, specifically reciting all values within this range and any ranges created thereby. For example, these adhesives can exhibit a storage modulus—2 value of between 40 and 300 kPa, between 73 kPa and 300 kPa, or between 146 kPa and 300 kPa, specifically reciting all values within this range and any ranges created thereby. However, the storage modulus must be considered in its entirety as a continuous, monotonic increasing function of the frequency. This means that the storage modulus—2 value can never be less than the storage modulus—1 value.

It is believed that with the appropriate selection of tan delta—1 and the storage modulus—1 values, that the adhesives of the present disclosure can reduce the negative impact caused by the consumer application habits mentioned heretofore. Recall, that consumers tend to not apply too much pressure to the article—aside from the wings (if available)—in order to avoid perceived contamination issues. Conventional pressure sensitive adhesives require much interaction from the consumer in the way of applying pressure to the article in order to form a bond to the undergarment. In contrast, it is believed that the PFA's of the present disclosure, with the appropriate selection of tan delta—1 and storage modulus—1 values as described herein, can form sufficient bonds with the current application habits of the consumer. So, with the appropriate selection of the tan delta—1 and storage modulus—1 values described herein, current user application habits can be accommodated.

The inventors have additionally discovered that the PFA's of the present disclosure, for initial attachment and stay in place functions, can exhibit a bonding compliance value—J1. The bonding compliance value characterizes the relationship between tan delta—1 and storage modulus—1. The equation for bonding compliance is shown below.

$$J1 = \frac{1}{G'_1} \cdot \frac{1}{\sqrt{1 + tan^2 \delta_1}}$$

wherein $G'_1$ is the storage modulus—1 value described herein and $tan^2 \delta_1$ is the square of the tan delta—1 value described herein.

Without wishing to be bound by theory, it is believed that bonding compliance values indicate how well an adhesive can flow and bond to the structure to which attachment is sought. In the case of cotton and/or microfiber undergarments, the bonding compliance value is indicative of how well the adhesive will flow and attach to the macrostructure (on the fiber level) of the undergarment. In the case of the PFA's of the present disclosure, these PFA's can exhibit a bonding compliance value of between 7.5 mm²/N and 950 mm²/N, from between 8.5 mm²/N to about 600 mm²/N or from about 9. mm²/N to about 321 mm²/N, specifically reciting all values within this range and any range created thereby.

Similarly, for the removal function, the inventors have found that the PFA's of the present disclosure can exhibit a debonding compliance value—J2. The debonding compliance value utilizes the relationship between tan delta 2 and storage modulus 2.

$$J2 = \frac{tan \delta_2}{G'_2} \cdot \frac{1}{\sqrt{1 + tan^2 \delta_2}}$$

wherein $G'_2$ is the storage modulus—2 value described herein and the $tan^2 \delta_2$ is the square of the tan delta—2 value described herein.

Without wishing to be bound by theory, it is believed that the debonding compliance value is indicative of the cohesive strength of the adhesive. And, it is therefore believed that the debonding compliance value can be indicative of whether an adhesive will leave residue on an undergarment upon removal of the article from the undergarment. In the case of the PFA's of the present disclosure, these PFA's can exhibit a debonding compliance value of between 0.3 mm²/N and 255.6 mm²/N, from about 1.5 mm²/N to about 150 mm²/N or from about 2.2 mm$^2$/N to about 13.2 mm$^2$/N, specifically reciting all values within this range and any ranges created thereby.

There are a couple of additional mechanical properties worth mentioning. For example, the elastic modulus or Young's modulus of the adhesive can provide insight into how an adhesive will perform when utilized in the PFA context. Recall that users often stretch the underwear prior to the application of the feminine hygiene article to the underwear. This stretching of the underwear can cause stress on the PFA of the feminine hygiene article. It is believed that PFA's that have a higher elastic modulus can better accommodate these forces. With this in mind, PFA's of the present disclosure can have an elastic modulus of 0.1 MPa to 1.5 MPa, between 0.12 MPa and 1.2 MPa, and between 0.14 MPa and 1 MPa, as measured at an elongation rate of 0.1 l/sec and an ambient temperature of 23 degrees C. plus or minus 2 degrees C.

As another example, the yield stress of the adhesives can provide useful insight as well. Without wishing to be bound by theory, it is believed that an adhesive acting as a PFA undergoes stress during removal. Recall that while in use, the PFA creates an adhesive interface between the backsheet of the absorbent article and the PFA as well as an adhesive interface between the PFA and the undergarment. It is believed that where the yield stress of the adhesive is below about 32 kPa, the adhesive interfaces survive removal and instead, the PFA fails internally. This internal failure can lead to increased residue left on the undergarment. However, where the PFA yield stress is above 32 kPa, it is believed that the adhesive has sufficient cohesive strength to cause the PFA to break the adhesive interface between the PFA and the undergarment thereby reducing the likelihood of PFA residue being left behind on the undergarment.

The adhesives of the present disclosure can exhibit a yield stress of 32 kPa or greater, 40 kPa or greater, or 50 kPa or greater, specifically reciting all values within these ranges and any ranges created thereby, when measured at 37 degrees C., in accordance with the Extensional Test Method for Yield Stress described herein. For example, in some specific configurations, the adhesives of the present disclosure can exhibit a yield stress of from between 30 kPa to about 100 kPa, from about 40 kPa to about 100 kPa, or from about 50 kPa to about 100 kPa, specifically reciting all values within these ranges and any ranges created thereby.

The above criteria can be useful insight as to whether an adhesive will successfully attach to undergarments of varying materials. However, the inventors have also surprisingly found that adhesives which meet the criteria mentioned herein can also exhibit lower surface energy values over adhesives which do not work well with microfiber and cotton materials. Additionally, the inventors have found that the adhesives that work well can exhibit a surface polarity that is a lower percentage of total surface energy than adhesives that do not work. It is believed that surface energy can impact initial attachment of the PFA to the undergarment as well as the sustained attachment of the PFA to the undergarment. It is also believed that this is especially true in the case of washing/drying aids being utilized by the consumer as mentioned before, e.g. deposition of hydrophobic actives (e.g. Alky Ester Quat & Fatty Acid) in the fabric softener on the surface of the clothing.

The adhesives of the present disclosure can exhibit a surface energy of less than 25 milliJoules per square meter as measured in accordance with the total surface energy method disclosed herein, specifically reciting all values within this range and any ranges created thereby. For example, the adhesives of the present disclosure can exhibit a surface energy of between 10 mJ/m$^2$ to 24 mJ/m$^2$, from 12.5 mJ/m$^2$ to 24 mJ/m$^2$, or from 15 mJ to 24 mJ/m$^2$, specifically reciting all values within these ranges and any ranges created thereby.

The adhesives of the present disclosure can exhibit a polar component of the surface energy of less than 10 percent. For example, the polar component can be between 1 percent to 9 percent, from 2 percent to 9 percent, or from 3 percent to 9 percent, specifically reciting all values within these ranges and any ranges created thereby.

Each of the above criteria were measured on a myriad of adhesives. Data for these measurements is provided herein.

Compositions

The adhesives of the present disclosure may comprise any suitable chemistry. The adhesives of the present disclosure are (as a reminder) pressure sensitive adhesives, which is intended to mean an adhesive that is inherently tacky, visco-elastic and cohesive in its normal dry state. In its simplest form, the adhesives of the present disclosure may comprise a polymer or polymer blend and a tackifier.

Some exemplary adhesives may comprise any number of polymer backbones. For example, adhesives of the present disclosure may comprise polymer backbones comprising at least one of: a thermoplastic polyurethane (TPU) silicone, an acrylate ester/vinyl pyrrolidone copolymers, dimethyl silicone polymers, styrene block copolymers. acrylate polymers or any suitable combination thereof.

Adhesives of the present disclosure may comprise a mixture of 60 to 90 weight percent of a pure rubbery copolymer (C-3-C12 alkyl ester) and from 10 to 40 weight percent of a polar component. Some suitable examples of the (C-3-C12 alkyl ester) include isooctyl acrylate, 2-ethylhexyl acrylate and n-butyl acrylate. Some suitable examples of the polar component include acrylic acid, methacrylic acid, ethylene-vinyl acetate, N-vinyl pyrrolidone and styrene block copolymer.

In one specific example an adhesive of the present disclosure comprises an ethylene-vinyl acetate and styrene block copolymer polymer backbone. These adhesives may utilize one or more tackifiers or blends thereof. The benefits of using tackifiers include (i) increasing the open time of the adhesive, which enables in general a better transfer to the second substrate in the lamination process, particularly when the open time of the process (defined as the distance between applicator and combining point divided by the line speed) is short, and (ii) enabling to achieve the desired polarity of the adhesive, which contributes to increase the bond strength to more polymer substrates (like e.g. polyester fibers), particularly for bonds in which an optimum entanglement of the fibers is difficult to achieve. For the adhesives of the present disclosure, the inventors have surprisingly found that minimizing the amount of tackifier has a net positive effect towards delivering better adhesion to underwear presenting a significantly higher dispersive component than polar component of the surface energy, as result of washing habits or because of a surface finish treatment in the case of most microfiber manufacturers.

The tackifier can have a Mw below 6,000 Da and a Tg below room temperature or slightly above. A Tg which is significantly above room temperature would yield an adhesive which is incompatible with the storage modulus values mentioned herein.

Suitable classes of tackifier include, for example, aromatic, aliphatic and cycloaliphatic hydrocarbon resins, mixed aromatic and aliphatic modified hydrocarbon resins, aromatic modified aliphatic hydrocarbon resins; terpenes, modified terpenes; natural rosins, modified rosins, rosin esters, and combinations thereof.

Suitable commercial tackifiers include, for example, the ESCOREZ series of trade designations from Exxon Mobil Chemical Company (Houston, Texas) including, ESCOREZ 5300, ESCOREZ 5400 and ESCOREZ 5600, the EASTOTAC series of trade designations from Eastman Chemical (Kingsport, Tenn.) including EASTOTAC H-100R and EASTOTAC H-100L.

In another specific example, an adhesive in accordance with the present disclosure comprises an acylate polymer based backbone. These adhesives may comprise from 80 to 100 weight percent of isooctyl acrylate and from 0 to 20 weight percent of acrylic acid. Furthermore, the acrylic pressure-sensitive adhesives may be self-tacky or tackified. Useful tackifiers (less than 2% weight fraction) for acrylics are rosin esters such as FORAL™ 85 or aromatics resins such as PICCOTEX™ LC-55 WKm, both available from Hercules, Inc. of Wilmington, DL, or else aliphatic resins such as ESCOREZ™ 1310LC, available from Exxon Chemical Co., Houston, TX.

Regarding the polar component, e.g. thermoplastic elastomeric materials, specifically useful for the present invention are for example styrene-isoprene block copolymers such as KRATON™ D1107P or linear styrene-(ethylene-butylene) block copolymers such as KRATON™ G1657 or else linear styrene-(ethylene-propylene) block copolymers such as KRATON™ G1657X and star styrene-butadiene block copolymer such as KRATON™ D1118X all available from Shell Chemical Co, Houston, TX.

These thermoplastic elastomeric or elastomeric materials can also be modified with tackifying resins or plasticizers to lower their melt viscosity to facilitate the formation of fine dispersions, with the smallest phase dimension preferably less than about 20 microns when blended with the acrylic pressure-sensitive adhesive. Tackifying resins or plasticizers useful with the elastomeric materials or the thermoplastic elastomeric materials are preferably miscible at the molecular level, i.e., soluble in, any or all of the polymeric segments of the elastomeric material or the thermoplastic elastomeric material. The tackifying resin, when present needs to be kept in low concentration, for reasons of reducing polar fraction of the adhesive surface energy as discuss previously, and may comprise about 5 to 600 parts by weight, more typically up to about 500 parts by weight, based on 100 parts by weight of the elastomeric material or the thermoplastic elastomeric material. Examples of tackifiers suitable for the adhesives of the present disclosure include but are not limited to liquid rubbers, hydrocarbon resins, rosin, natural resins such as dimerized or hydrogenated balsams and esterified abietic acids, polyterpenes, terpene phenolics, phenol-formaldehyde resins, and rosin esters. Plasticizers are also an important ingredient in the PFA's of the present disclosure and are usually present between 5 and 10% by weight. Examples of plasticizers include but are not limited to polybutene, paraffinic oils, petrolatum, and certain phthalates with long aliphatic side chains such as ditridecyl phthalate.

The adhesives of the present disclosure may also optionally comprise additives such as one or more antioxidant, UV stabilizer, brightener, colorant, fragrance, odor control actives, etc. The adhesive may comprise less than 5% by weight of such additives. Any antioxidant known to a person of ordinary skill in the art may be used in the adhesives of the present disclosure.

Samples

Several samples were obtained and tested against criteria disclosed herein.

Samples 1-3 were polyacrylate based adhesives and each had good adhesion to microfiber undergarments.

Sample 4 was a mixture of ethylene vinyl acetate and styrene block copolymer-based adhesives and had good adhesion to microfiber undergarments.

Samples 5-6 were polyurethane elastomer-based adhesives and each did not provide sufficient adhesion to microfiber undergarments.

Samples 7-8 were styrene block copolymer-based adhesives and each did not provide sufficient adhesion to microfiber undergarments.

Sample 9 was a styrene block copolymer based adhesive.

Samples 1-2 utilized adhesives that are commercially available as general-purpose adhesives. Sample 1 is available under the trade name "Voxmude Double Sided Clear Adhesive Gel Grip Tape." This tape is advertised as being able to be utilized on a variety of wall surfaces and floor surfaces.

Sample 2 is available under the trade name "Avalution Nano Tape" by Anothera. This tape is advertised as being able to be utilized on a variety of surfaces, e.g. glass, metal, kitchen cabinets, and tile.

Samples 3 and 4 were fabric adhesives tapes that are commercially available for securing fabric to the skin. Sample 3 is available from 3M under the trade name "Essentials Wardrobe Tape Strips." Sample 4 is available as Hollywood Fashion Secrets® Fashion Tape.

Sample 5 was an adhesive that is commercially available as a general-purpose adhesive. Sample 5 is available under the trade name "Ivy Grip Tape, Washable Adhesive Tape." This tape is listed as a being able to attach items to walls, cell phone holders, etc.

Sample 6 is commercially available and sold under the trade name "The Stikk brand gel pad." These gel pads are utilized for attaching bundles of electrical cords/wires to a wall or their respective enclosures.

Samples 7-9 are commercially available adhesive which have been utilized as PFA's.

It is worth noting that while Samples 1-4 are currently in the market, none are currently being utilized as PFA. And contrary to the indicated uses of, for example, Samples 1 and 2, PFA's are transient. In other words, PFA's are applied and removed typically after a matter of hours. In contrast, the indicated uses of Samples 1 and 2, demonstrate that these tapes are meant to provide much longer attachment between items, e.g. from months to years.

The indications of use for Samples 3 and 4 are more transient than those of Samples 1 and 2, as their indications are for attachment of fabric to skin. However, these tapes are primarily used for blouse gaps, securing necklines and generally reducing the likelihood of wardrobe malfunctions. However, the stresses and strains experienced by an adhesive placed on one's neckline versus those experienced by a PFA are quite disparate. The stresses and strains that a PFA experiences are much greater as the region in which the PFA is disposed during use can be subject to a much larger range of motion than a neckline.

Table 1 shows the total surface energy, the polar component of the surface energy, surface polarity, yield stress and relaxation time, of the adhesives that were measured.

TABLE 1

| Sample No. | Surface Energy (mJ/m^2) | Polar Component of Surface Energy (mJ/m²) | Surface Polarity (%) | Yield Stress (kPa) | Relaxation Time (s) |
|---|---|---|---|---|---|
| 1 | 23.1 | 0.858 | 3.72 | — | 11.49 |
| 2 | 22.4 | 0.795 | 3.55 | — | 11.05 |
| 3 | 22.0 | 1.339 | 6.10 | — | 10.80 |
| 4 | 20.4 | 0.736 | 3.60 | 53.32 | 10.17 |
| 5 | 22.4 | 3.09 | 13.79 | — | 30.91 |
| 6 | 27.1 | 4.94 | 18.23 | — | 41.99 |
| 7 | 31.2 | 5.63 | 18.05 | 16.49 | 24.30 |
| 8 | 30.6 | 4.97 | 16.25 | 15.74 | 31.78 |
| 9 | 28.4 | 3.01 | 10.61 | 16.69 | 29.15 |

Additionally, peel tests and residue tests were performed on a number of these samples. The data is provided below in Table 2. The peel test data was acquired via the Peel Force test as described herein and the residue test was performed via the Adhesive Residue test described herein.

TABLE 2

Figure 13:
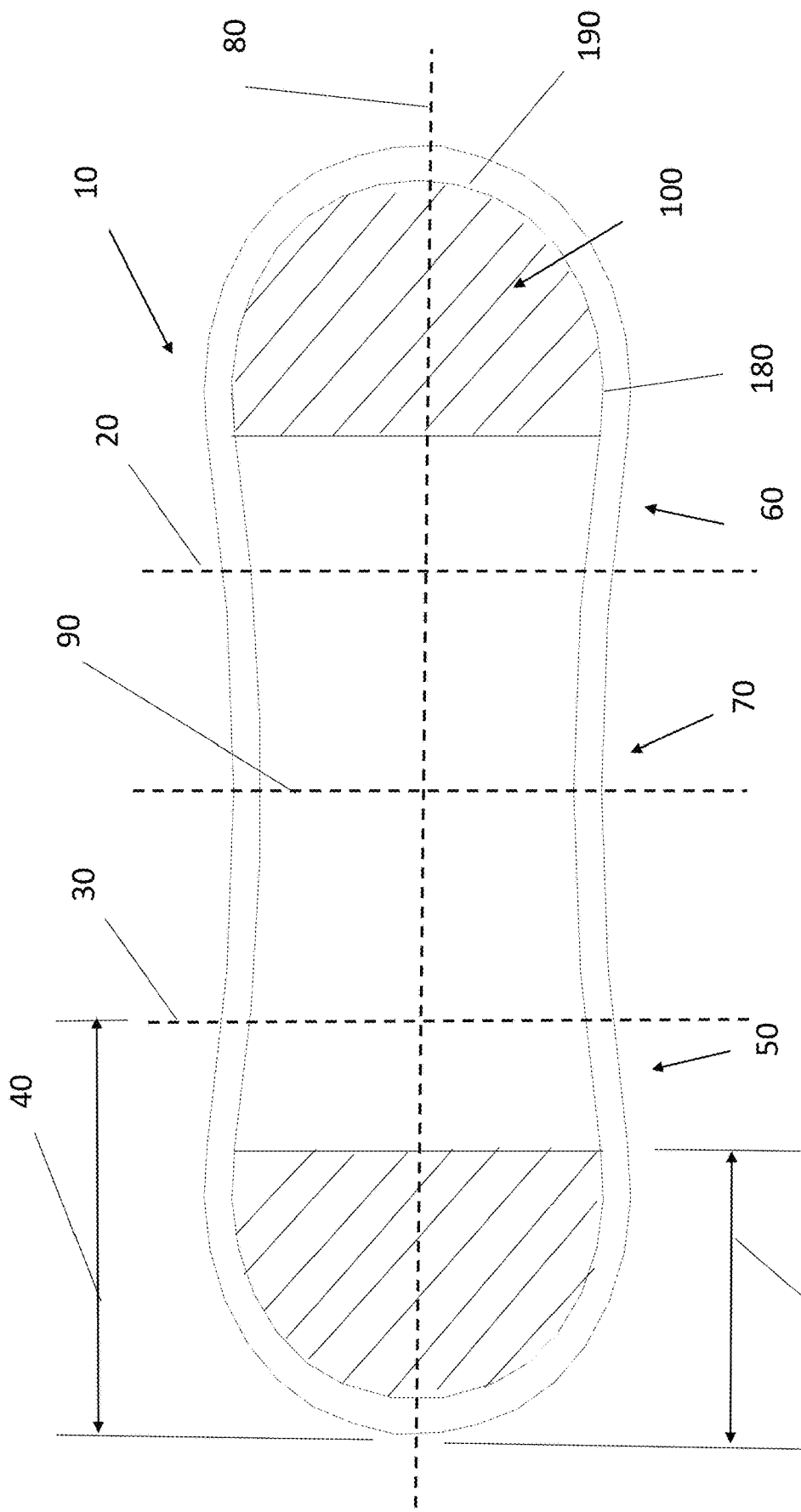
FIG. 13 is a schematic representation of an absorbent article constructed in accordance with the present disclosure.
Figure 14A:
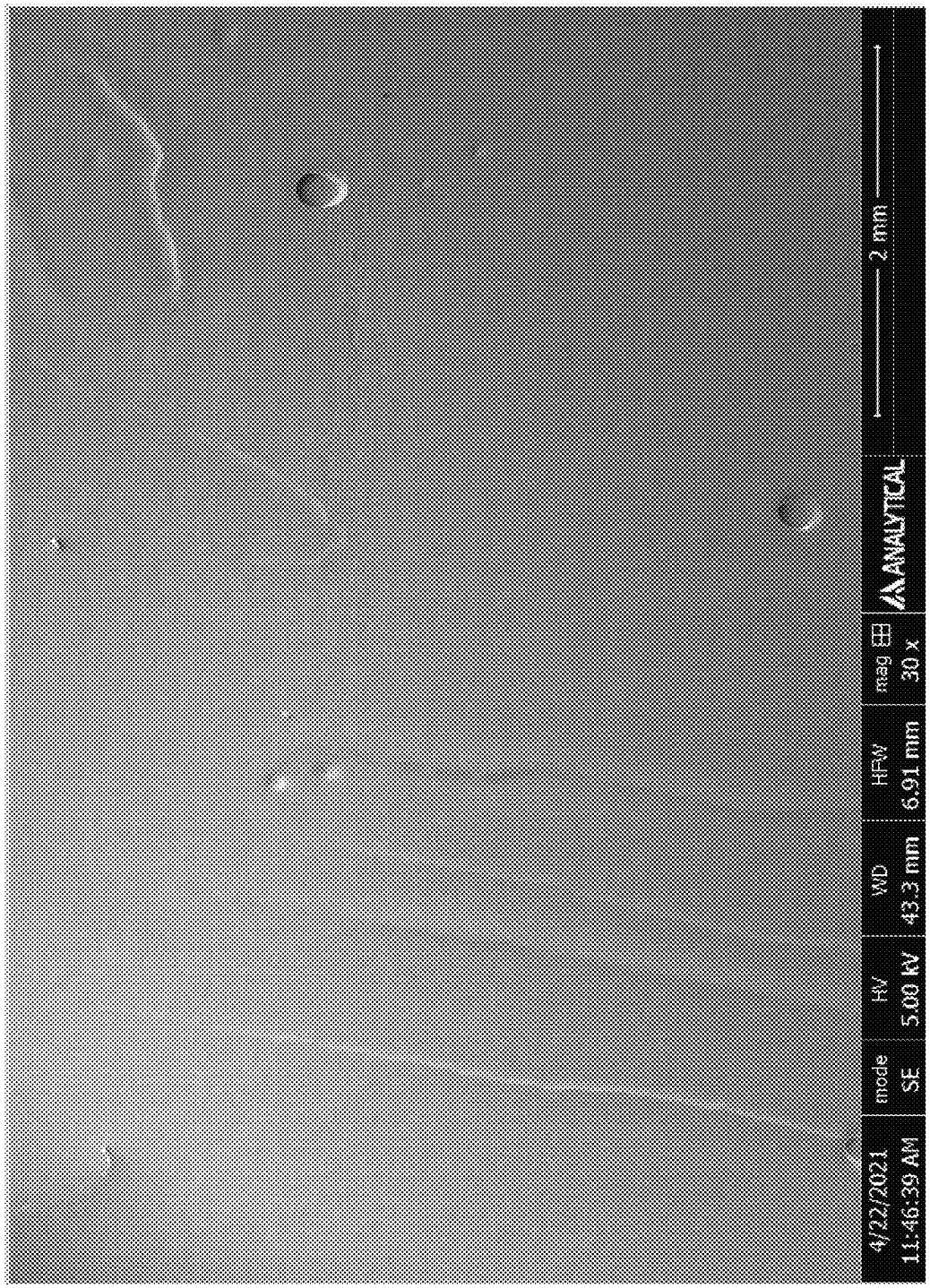
FIGS. 14A-14D are SEM images showing conventional adhesive on an absorbent article.
Figure 14B:
Figure 14C:
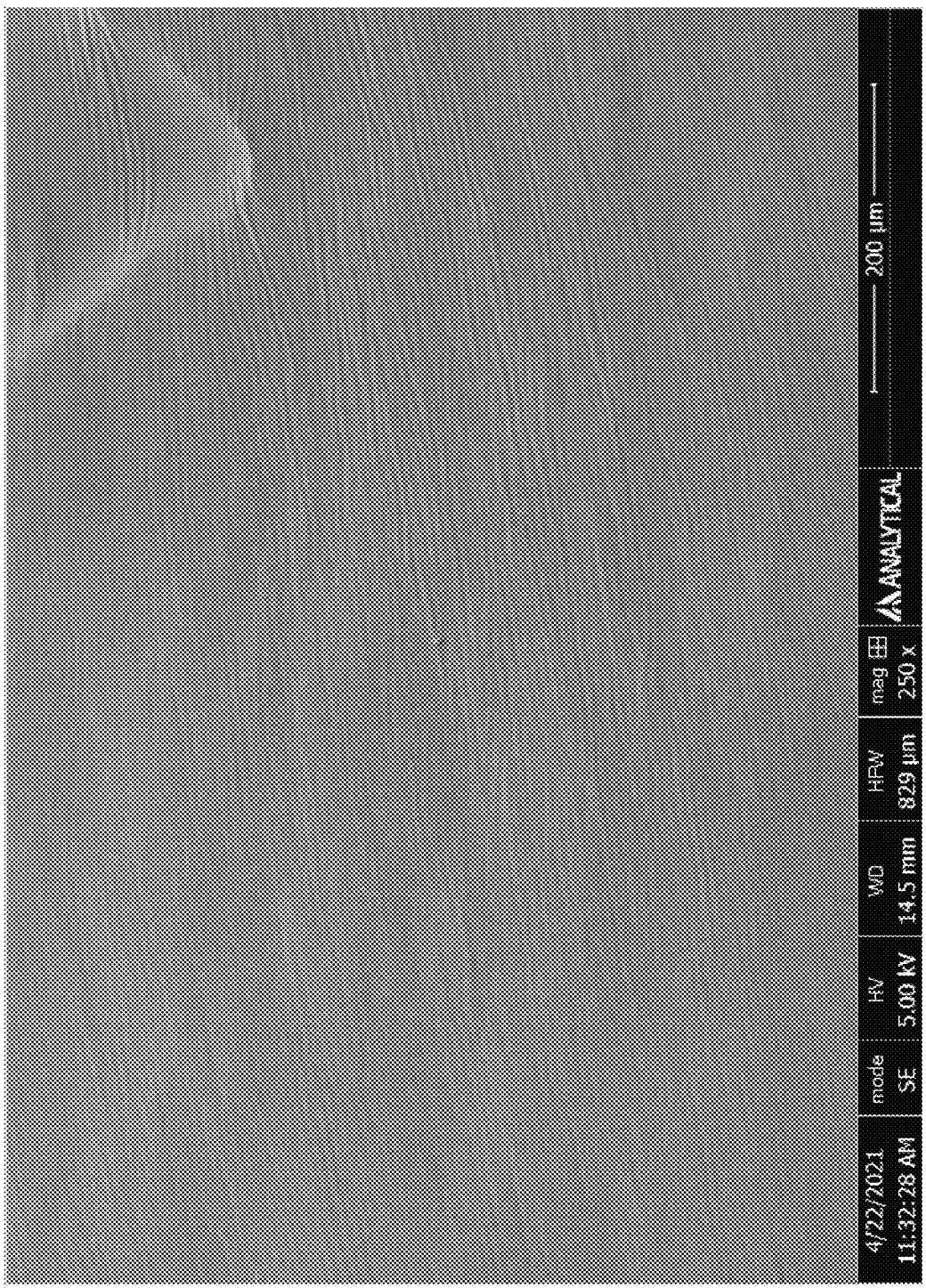
Figure 14D:
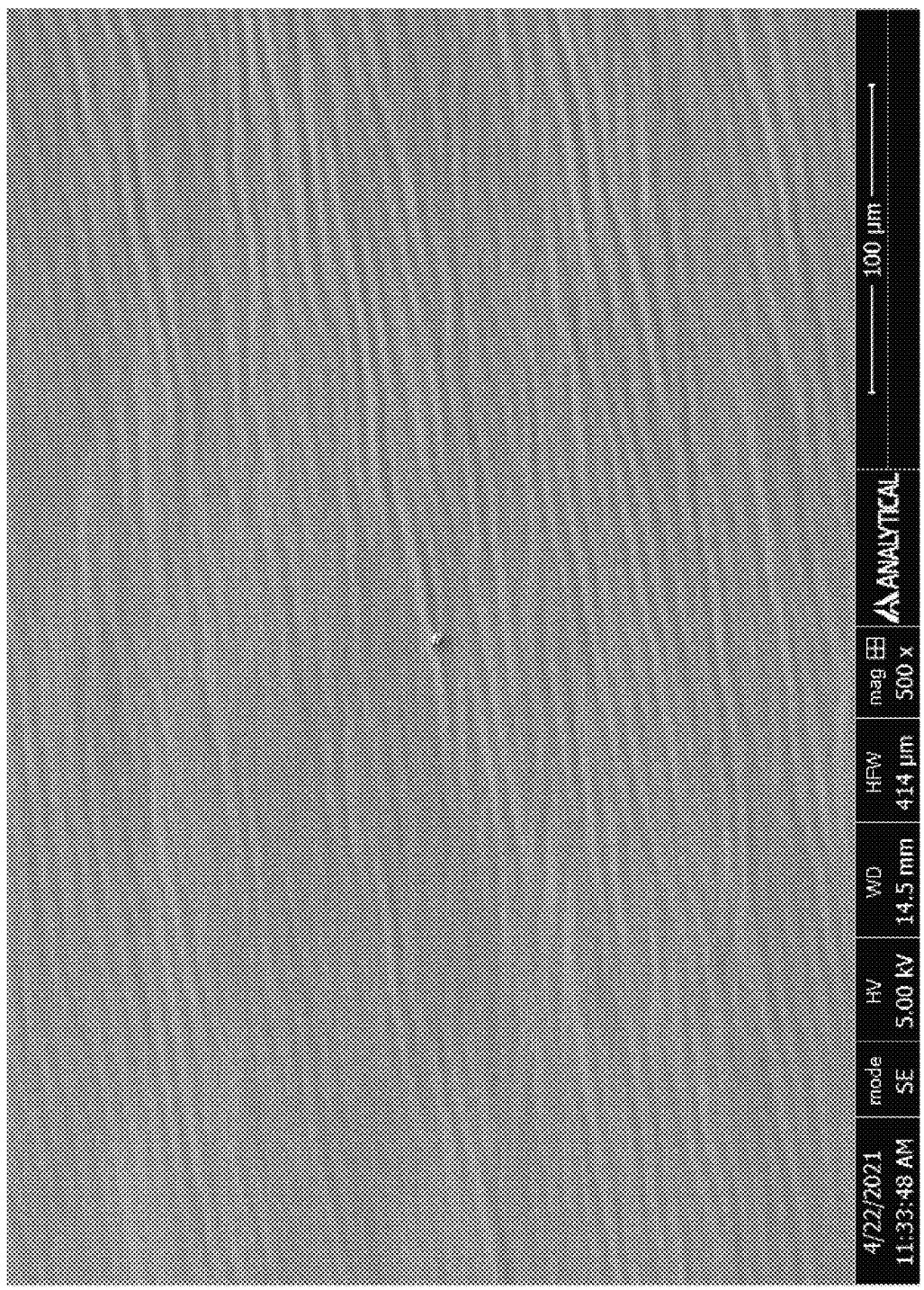
Figure 15A:
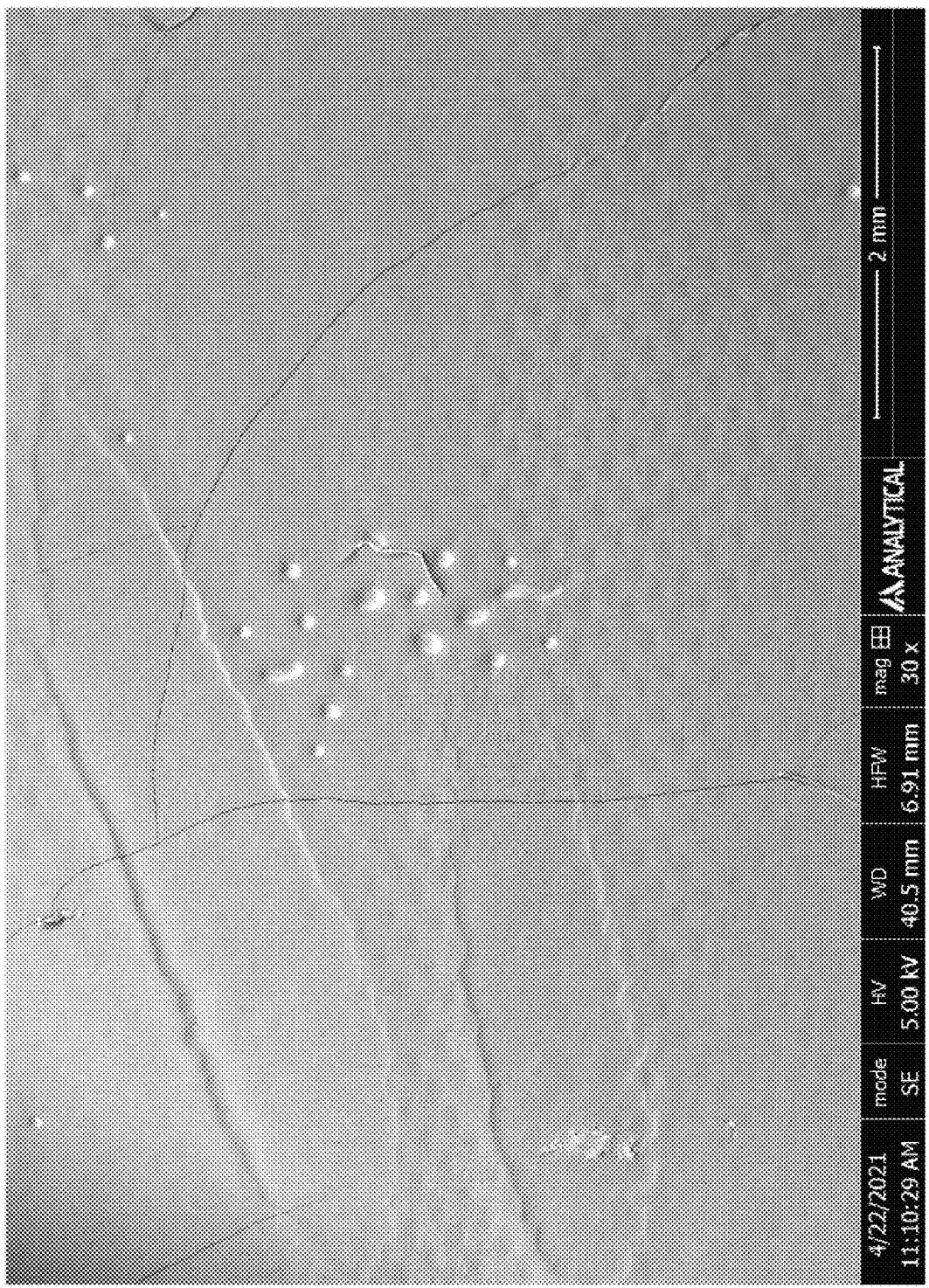
FIGS. 15A-15D are SEM images showing a pre-formed adhesive on an absorbent article.
Figure 15B:
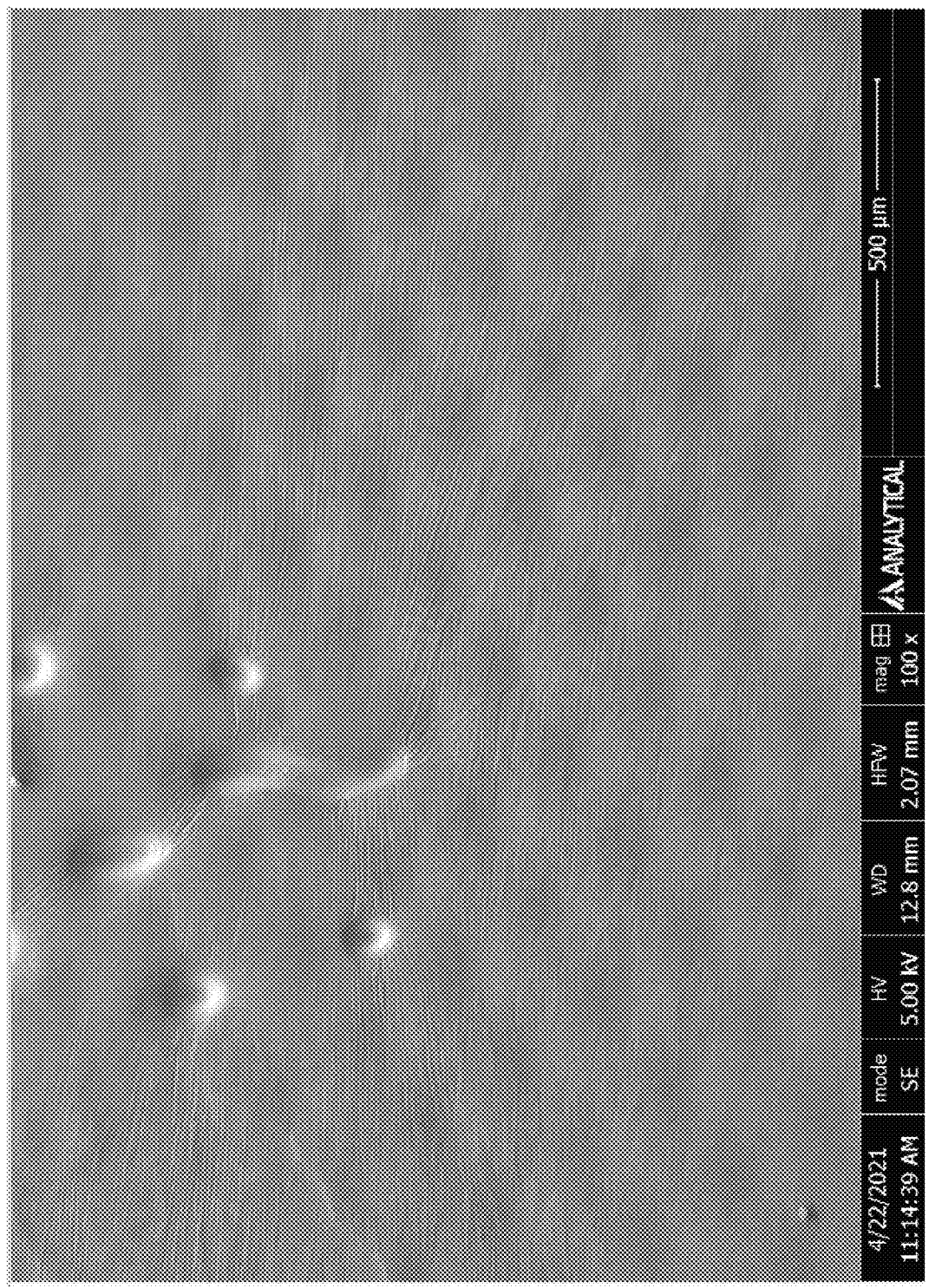
Figure 15C:
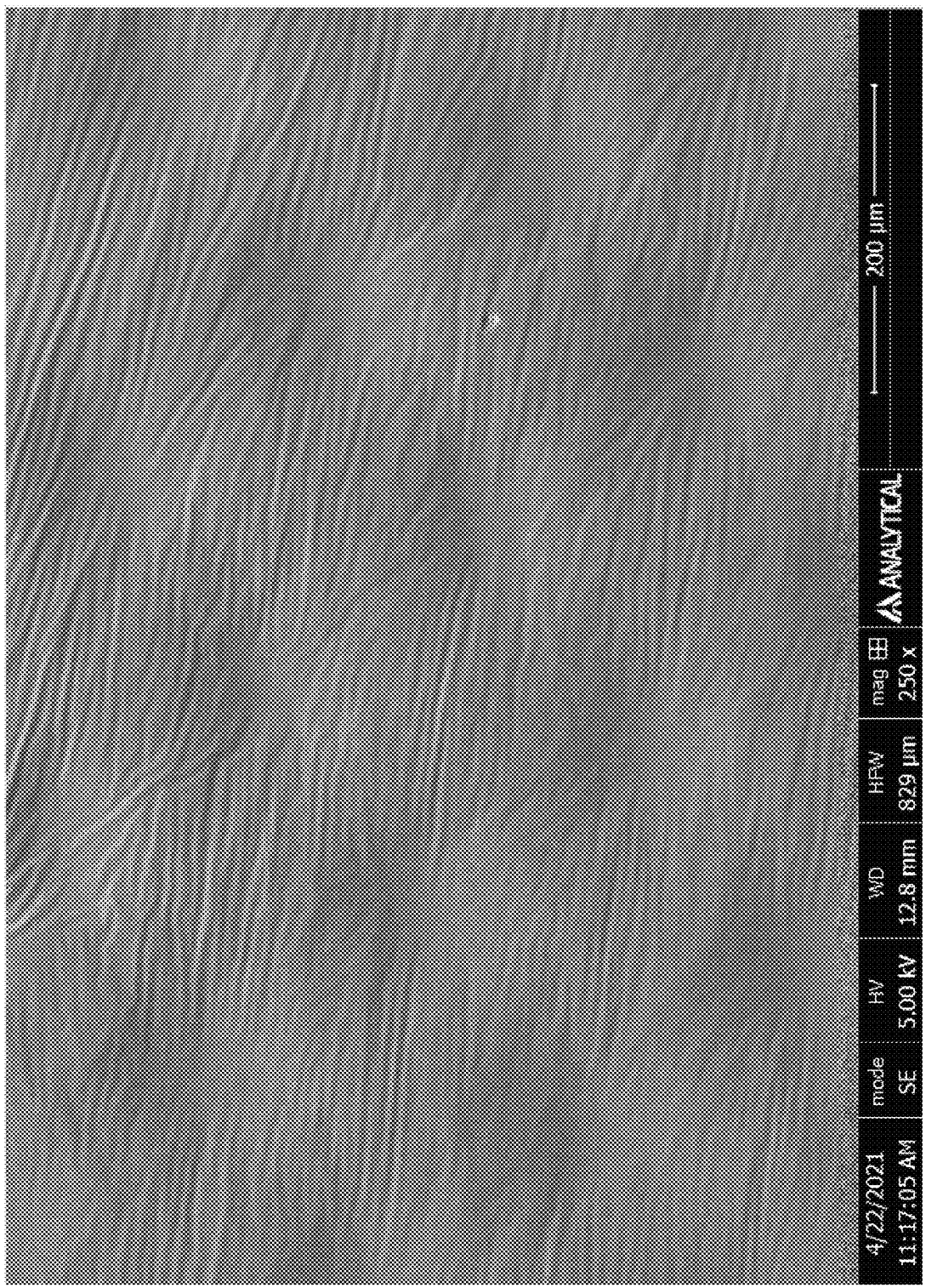
Figure 15D:
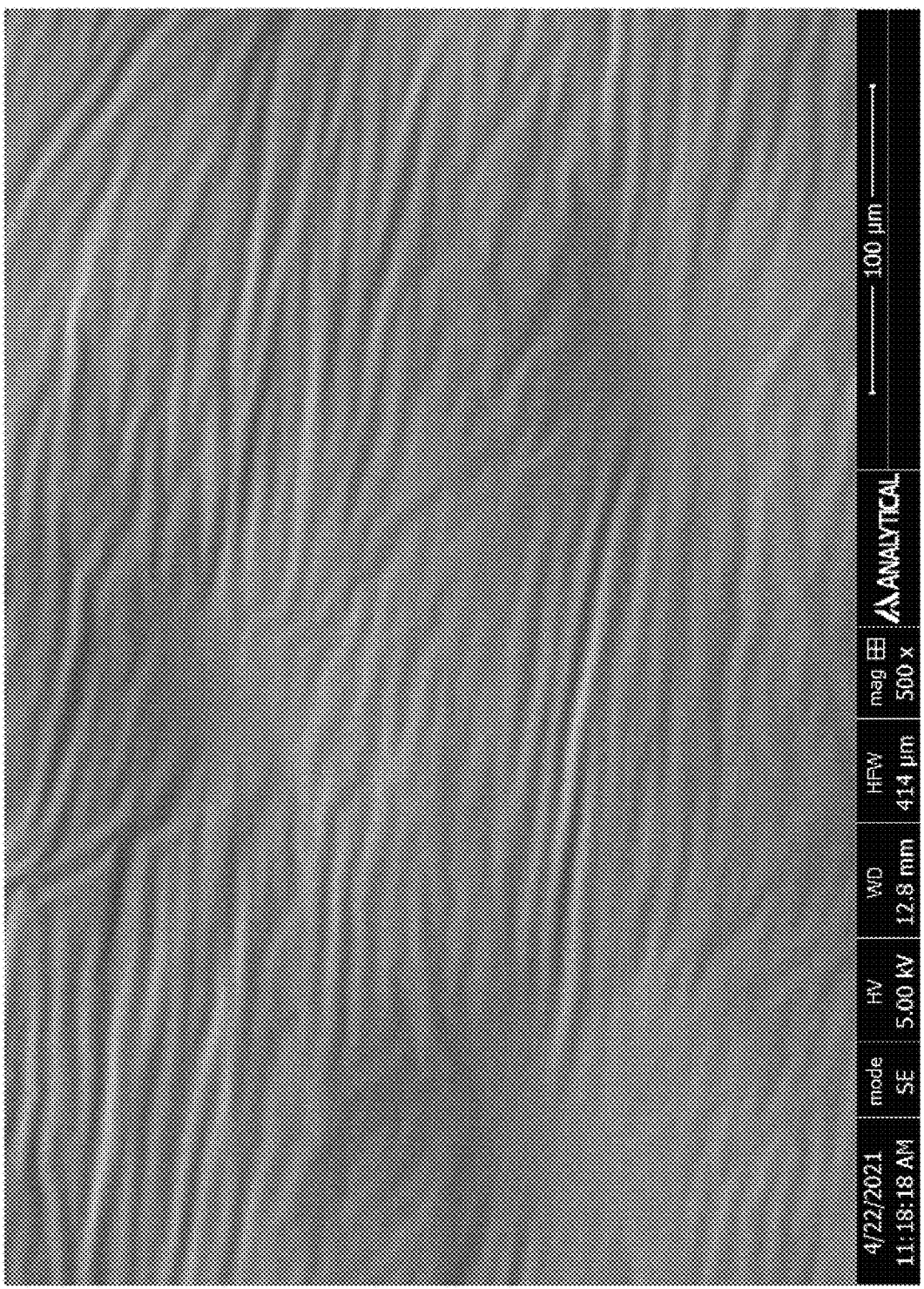

| Sample No. | Adhesive Coverage | Peel Force (N) | Residue |
|---|---|---|---|
| 1 | Full Coverage | 1.97 | No |
| 2 | Full Coverage | 2.06 | No |
| 3 | Full Coverage | 2.34 | No |
| 4 | Full Coverage | 2.44 | No |
| 4' | 75 mm x 50 mm blocks at ends of pad | 1.18 | No |
| 6 | Full Coverage | 0.18 | No |
| 7 | Pattern of FIG. 13 | 0.84 | No |

It is believed that in order to provide good initial attachment and stay in place characteristics, the PFA's of the present disclosure can exhibit a peel force of at least 1.0 N, about 1.1 N or about 1.2 N, in accordance with the Peel Force Test, specifically reciting all values within these ranges and any ranges created thereby. Also, it is believed that in order to reduce the likelihood of leaving residue behind and/or yielding the backsheet of the absorbent article, the peel force can be less than about 5 N, less than about 4 N, or about 3N or less, specifically reciting all values within these ranges and any ranges created thereby. So, the PFA's of the present disclosure can exhibit a peel force of at least 1N to about 5.0 N, from about 1.0 N to about 4.0 N or from about 1.0 N to about 3.0 N, specifically reciting all values within these ranges and any ranges created thereby.

Sample 4' is an acrylate based adhesive version of Sample 4. Sample 4' is sold under the same trade name as Sample 4. It is also worth noting that in accordance with the Adhesive Residue test method, Samples 1-4 and Sample 4' left no residue on the undergarment upon removal of the article.

For the peel test and residue test data in Table 2, absorbent articles were constructed from the following materials: (i) 18 gsm spunbond bico nonwoven topsheet; (ii) 55 gsm spunlaced secondary topsheet; (iii) a pair of pulp airlaid cores each of 135 gsm; (iv) a pair of superabsorbent polymer layers being substantially air-felt free; and (v) a 12 gsm film backsheet.

For those samples where "full coverage" adhesive was utilized, the adhesive was applied to cover an area of 300 mm by 59 mm of the pad. For Sample 7, the basis weight of the adhesive was 15 gsm. The remainder of the adhesives were applied to the garment-facing surface of the articles in the basis weights in which they were purchased.

Figure 1B:
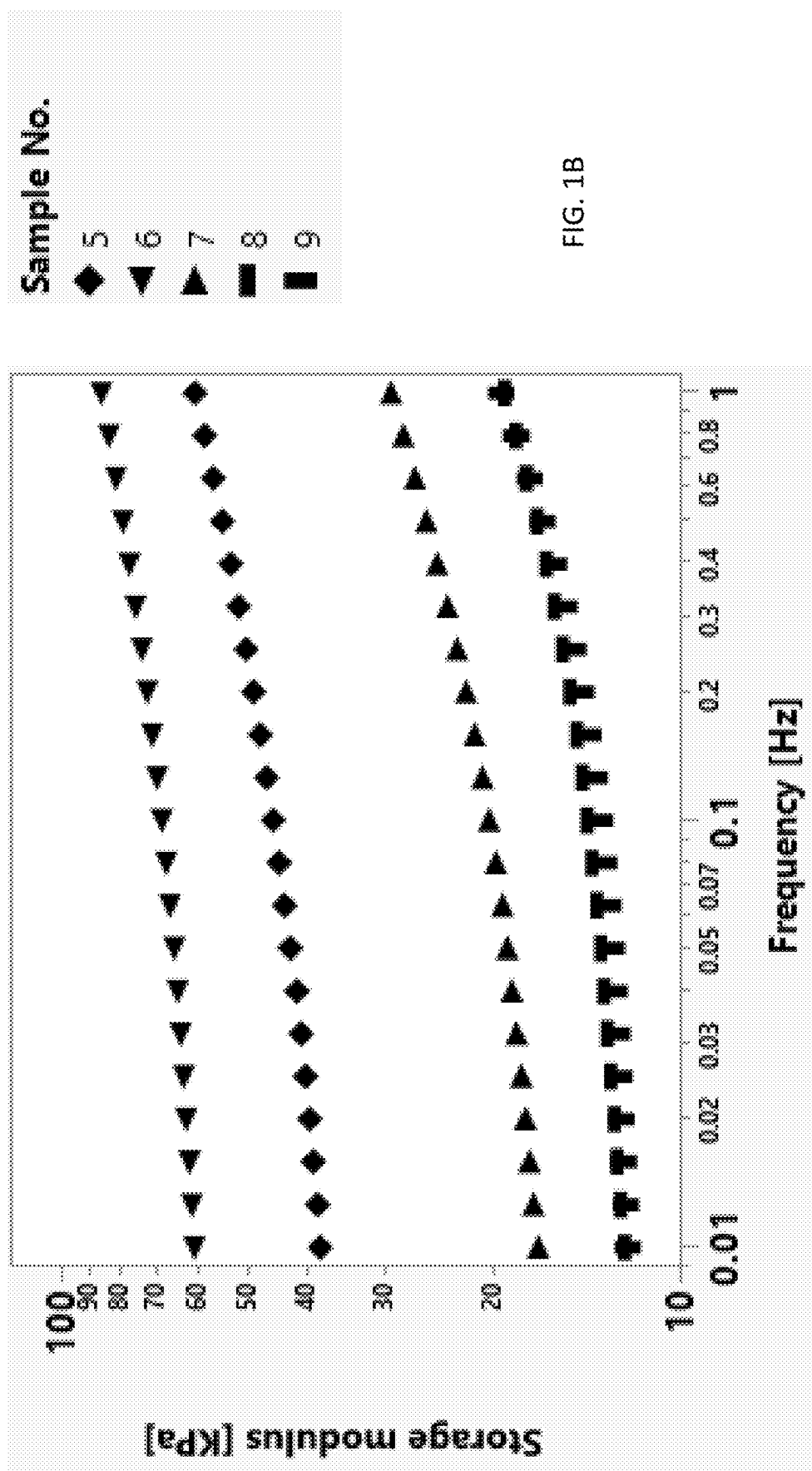
FIG. 1B is a graph showing the storage modulus—1 values for adhesive Samples 5-9 which do not meet the criteria described in the present disclosure.

FIGS. 1A, 1B, 2A and 2B demonstrate that samples 1-4 fall within the scope of the claimed ranges for adhesives which work well for both cotton and microfiber undergarments. FIGS. 1A, 1B, 2A and 2B, are graphs which show the storage modulus—1 and tan delta—1 values for Samples 1-9, respectively, in the frequency range of 0.01 Hz to 1 Hz. Recall that this frequency range can be indicative of initial bonding and stay in place functionality for the adhesive and the absorbent article. Specifically, FIGS. 1A and 1B show graphs of the storage modulus—1 value for the Samples 1-4 and 5-9, respectively.

Figure 2A:
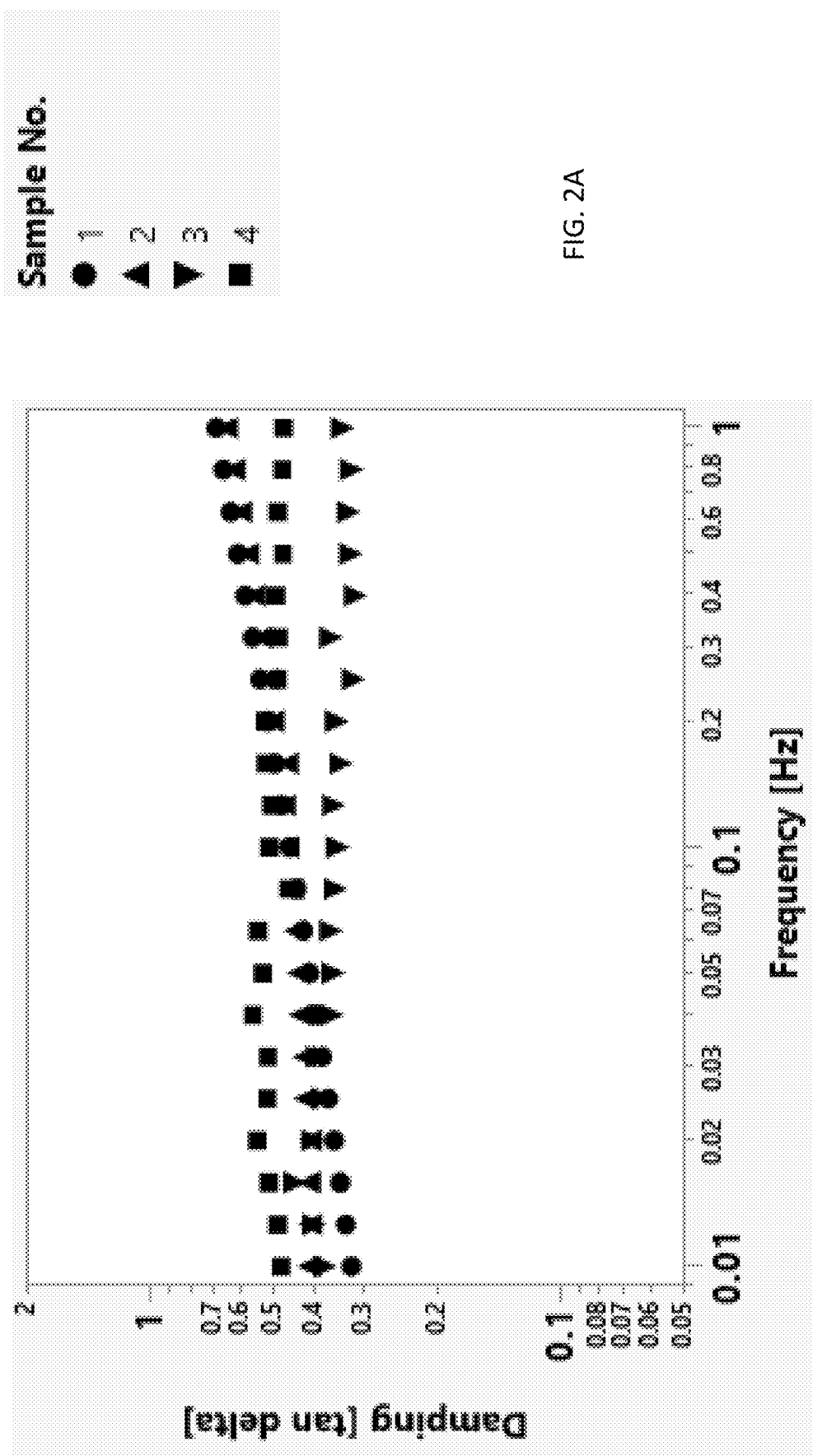
FIG. 2A is a graph showing the tan delta—1 values for adhesive Samples 1-4 which are in accordance with the present disclosure.
Figure 2B:
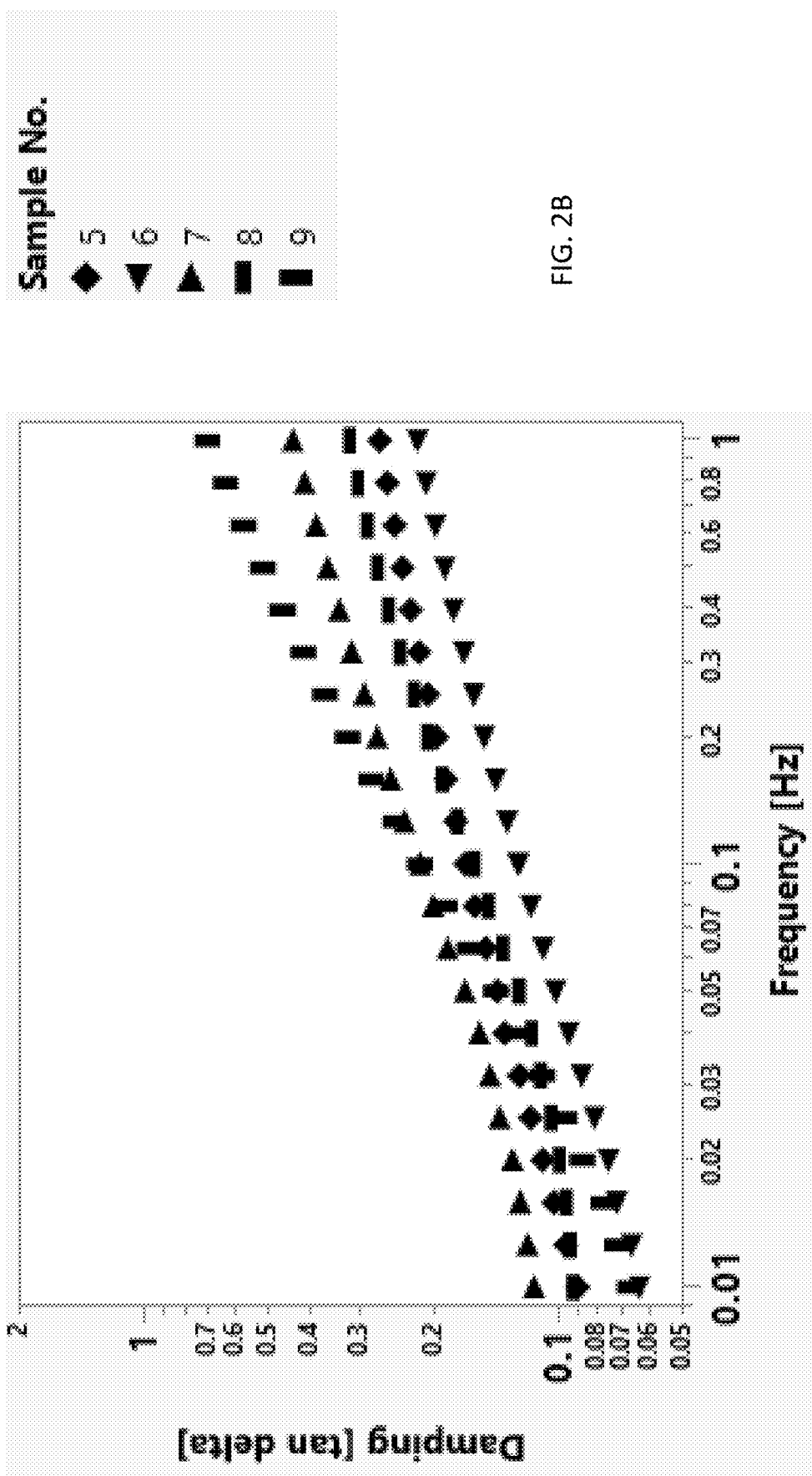
FIG. 2B is a graph showing the tan delta—1 values for adhesive Samples 5-9 which do not meet the criteria described in the present disclosure.

FIGS. 2A and 2B show graphs of the tan delta—1 for Samples 1-4 and 5-9, respectively. As noted previously, Samples 1-4 can provide improved performance over conventional PFAs particularly in the context of microfiber undergarments. In contrast, Samples 5-9 do not provide good adhesion to microfiber undergarments.

Figure 3A:
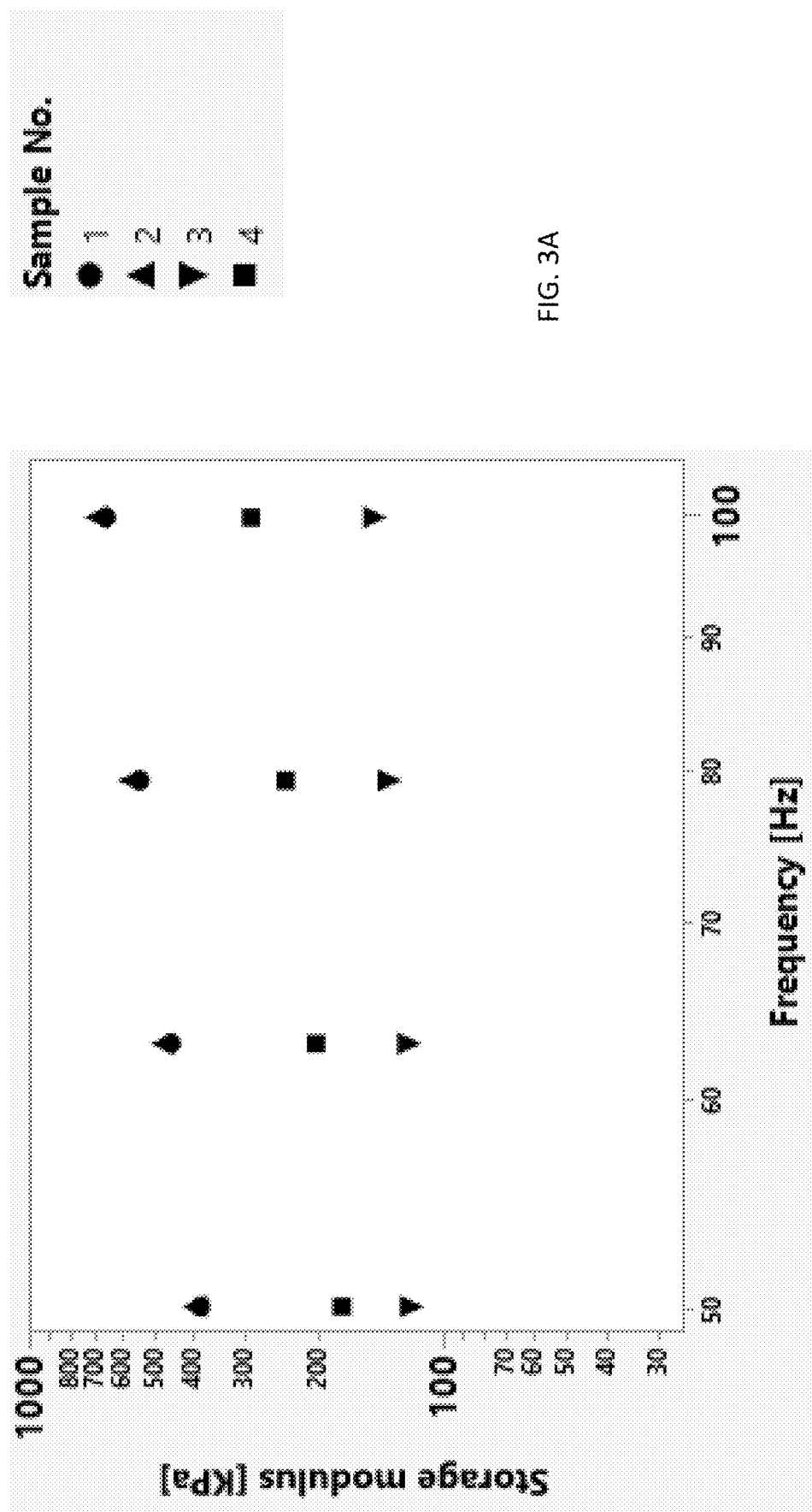
FIG. 3A is a graph showing the storage modulus—2 values for adhesive Samples 1-4 which are in accordance with the present disclosure.
Figure 3B:
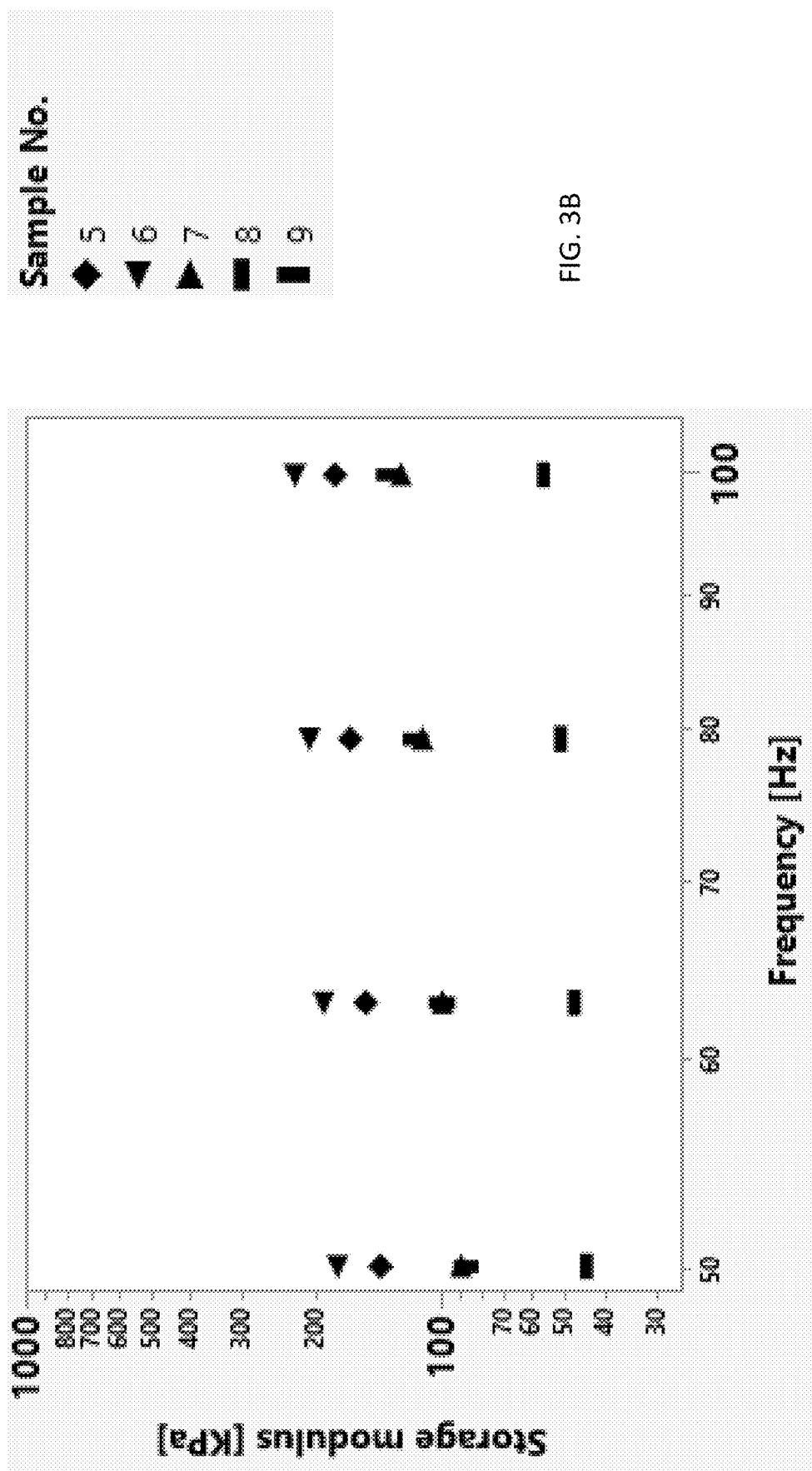
FIG. 3B is a graph showing the storage modulus—2 values for adhesive Samples 5-9 which do not meet the criteria described in the present disclosure.

FIGS. 3A, 3B, 4A and 4B, are graphs which show the storage modulus—2 and tan delta—2 values for Samples 1-9, respectively, in the frequency range of 50 Hz to 100 Hz. Recall that this frequency range can be indicative of the cohesiveness of the adhesive and be an indicator of how the adhesive will perform during removal from the underwear. Specifically, FIGS. 3A and 3B, show graphs of the storage modulus—2 values for Samples 1-4 and Samples 5-9, respectively.

Figure 4A:
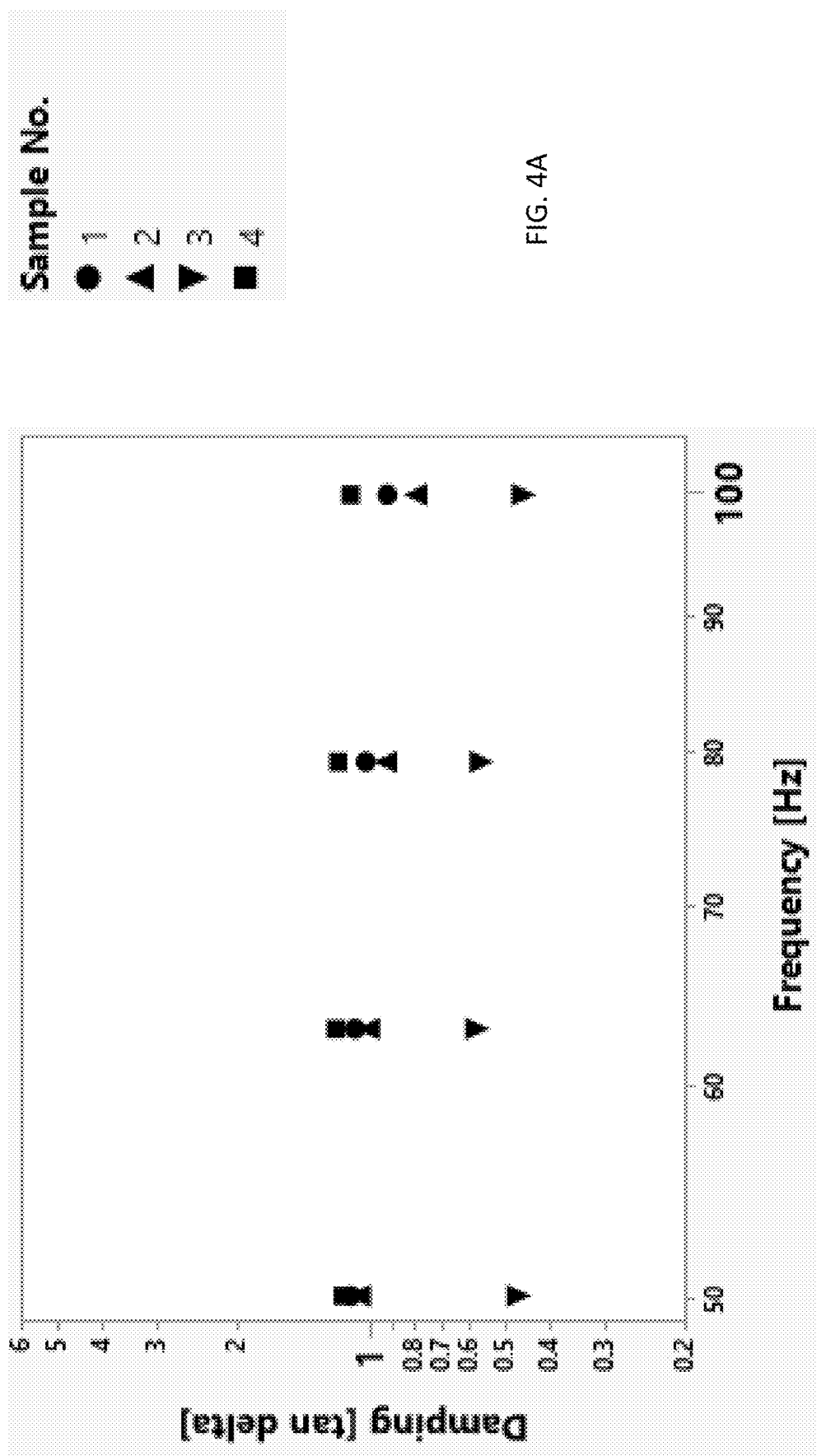
FIG. 4A is a graph showing the tan delta—2 values for adhesive Samples 1-4 which are in accordance with the present disclosure.
Figure 4B:
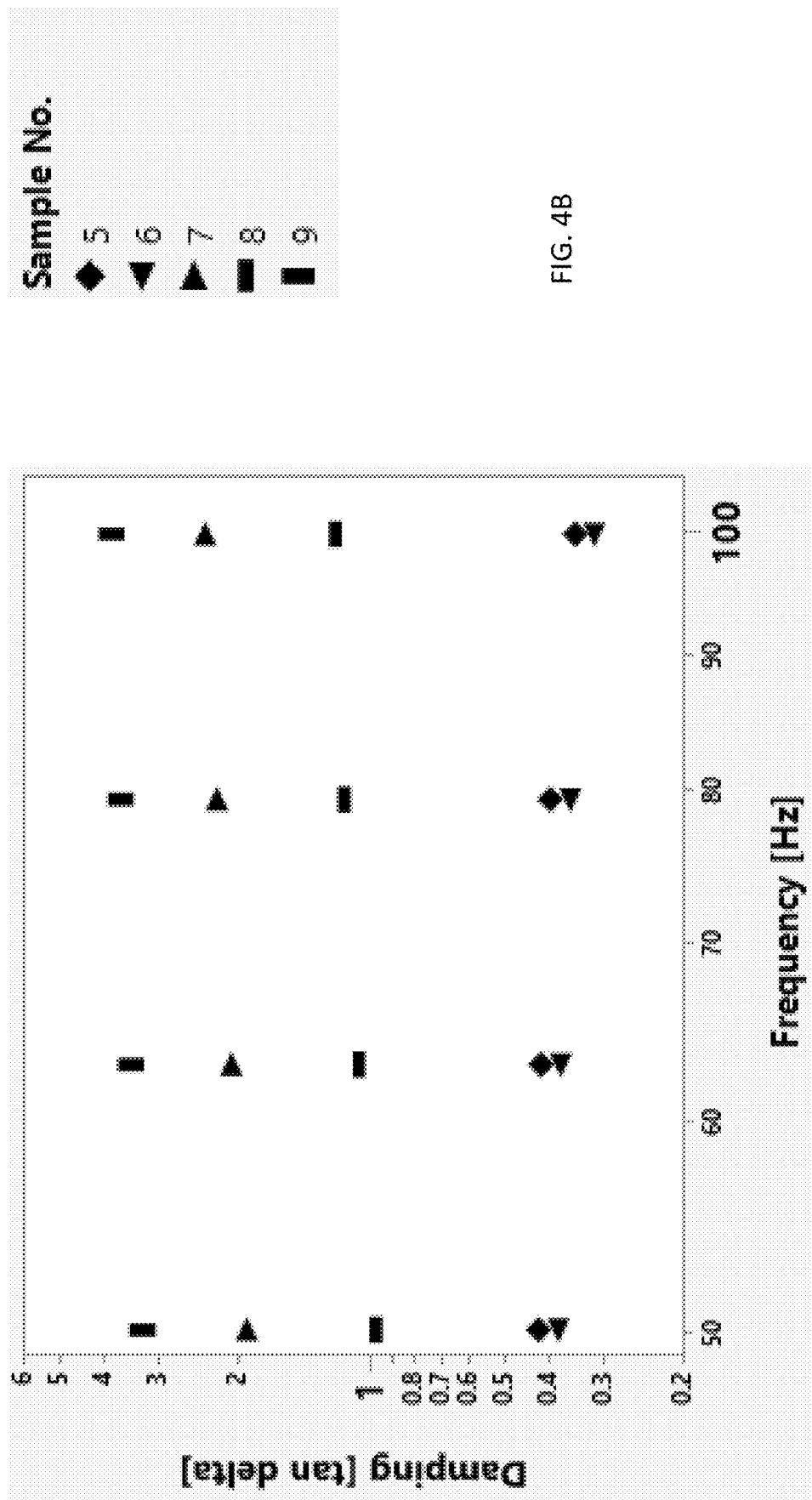
FIG. 4B is a graph showing the tan delta—2 values for adhesive Samples 5-9 which do not meet the criteria described in the present disclosure.
Figure 6A:
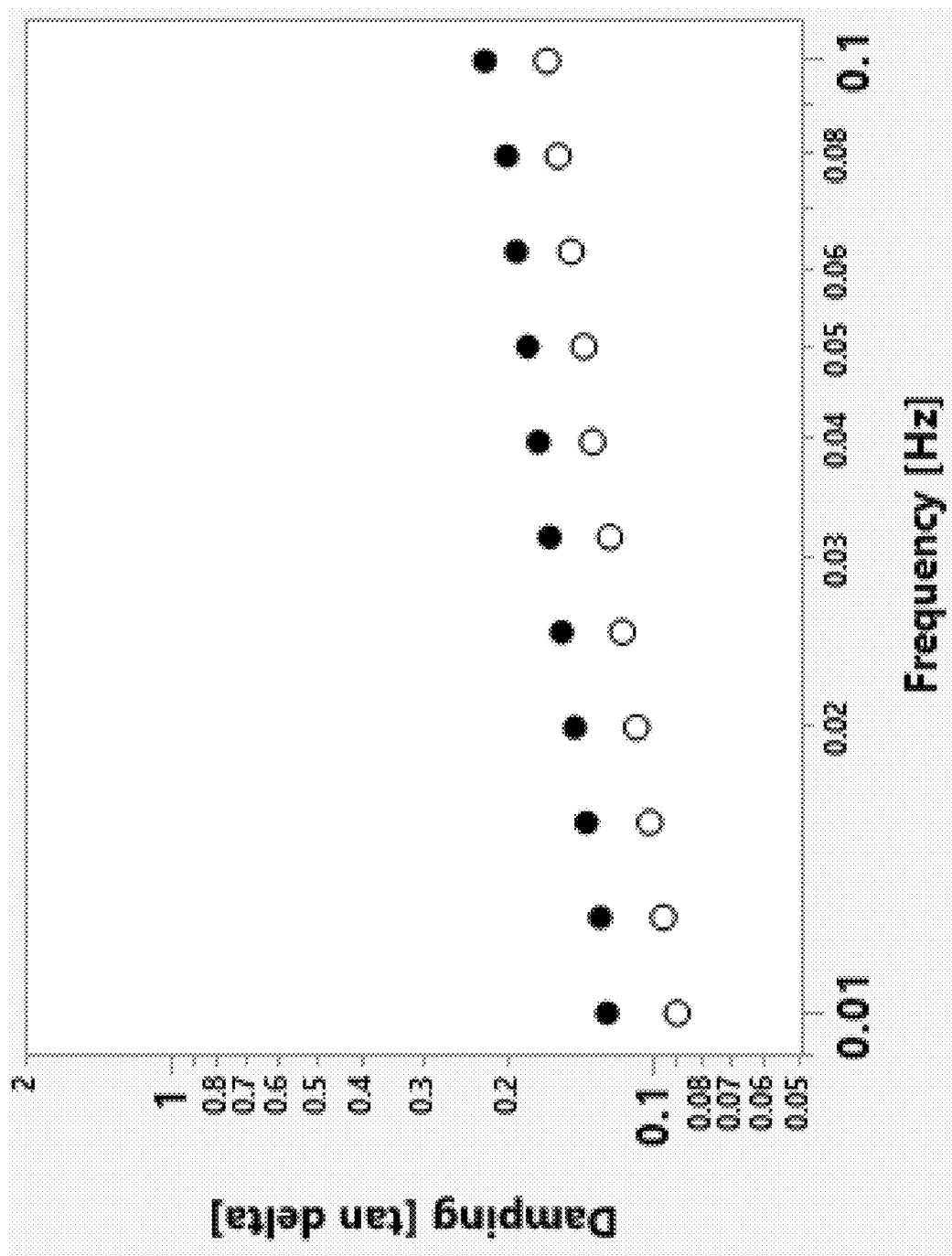
Figure 8B:
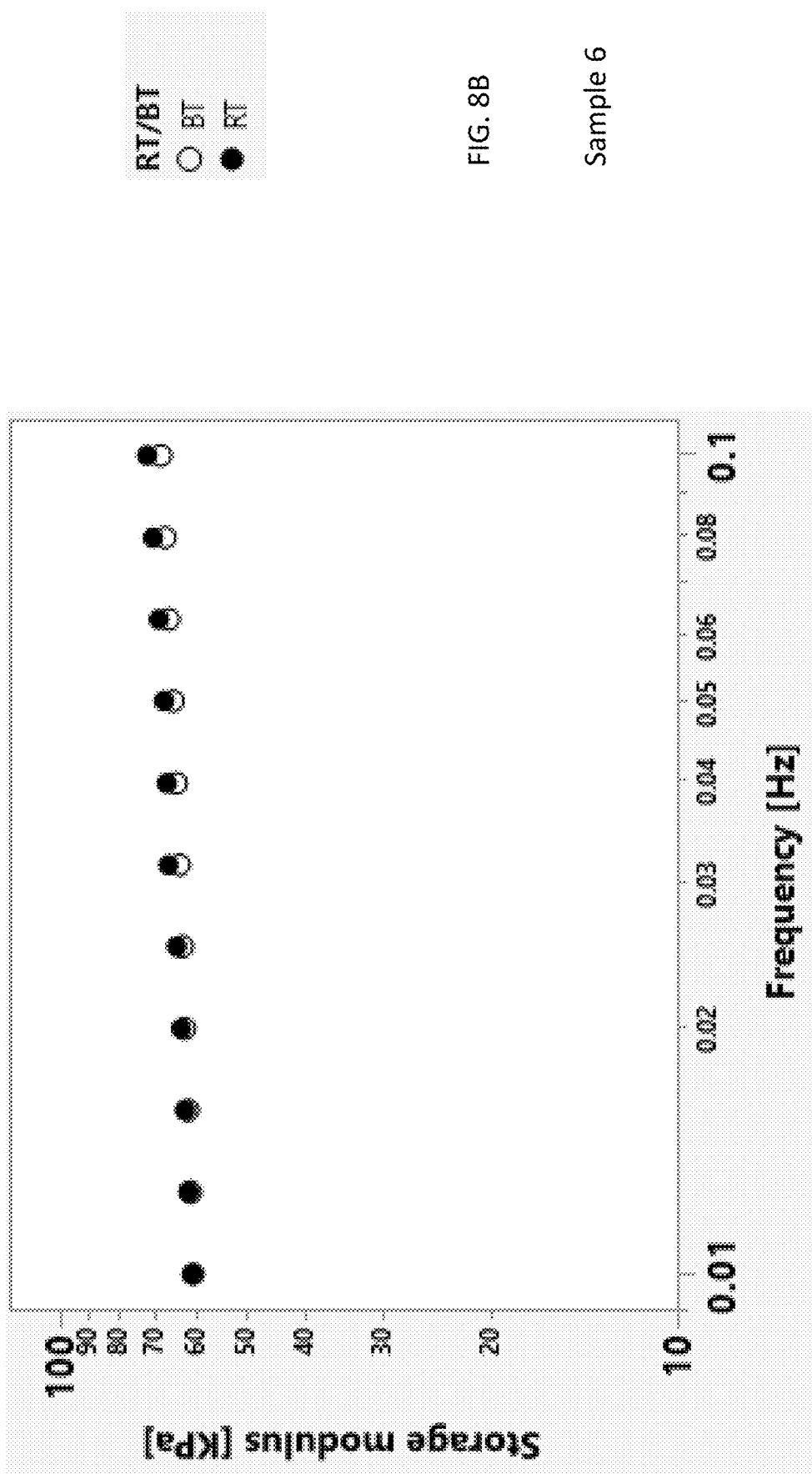
Figure 8C:
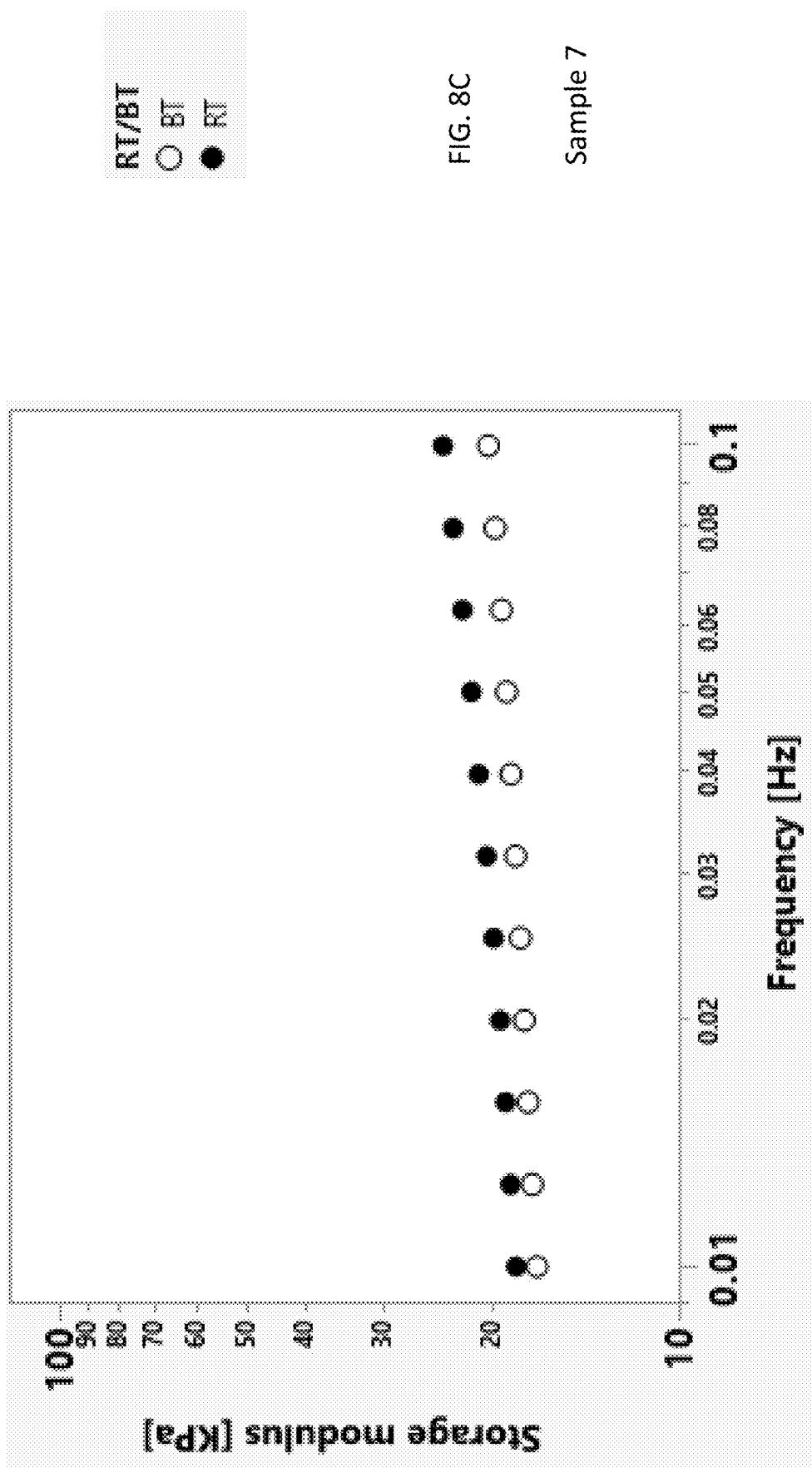

FIGS. 4A and 4B show graphs of the tan delta—2 values for Samples 1-4 and Samples 5-9, respectively. As shown, Samples 1-4 are within the ranges of tan delta—2 values described heretofore.

FIGS. 5A-5E and 6A-6E, are graphs showing tan delta—1 value behavior at 25 degrees C. versus 37 degrees C. for Samples 1-4 and Samples 5-9, respectively. FIGS. 7A-7E and 8A-8E, are graphs showing the storage modulus—1 value behavior at 25 degrees C. versus 37 degrees C. for Samples 1-4 and Samples 5-9, respectively.

The behavior of the adhesives of the present disclosure at both of these temperature points can be important. Without wishing to be bound by theory, it is believed that during use, a user's undergarments are close to body temperature (37 degrees C.) or at least approaches body temperature minus a couple/few degrees. However, during application of an absorbent article, the undergarment is pulled down and the absorbent article is applied. While the undergarment is down, it is believed that the undergarment is close to or at least approaches room temperature (25 degrees C.). And as noted previously, it is at this temperature at which initial application occurs. Subsequent to the application of the article to the undergarment, the undergarment—along with the absorbent article—is pulled up into wearing position. In this position, it is believed that both the absorbent article and the undergarment increase in temperature. And over a brief period of time, it is believed that both the absorbent article and undergarment are close to body temperature or at least asymptotically approach body temperature. With this in mind, it is further believed that adhesives which have a similar tan delta—1 range 0.28-1.2 at room temperature (25 degrees C.) as at body temperature (37 degree C.) and a Storage Modulus-1 value of <85 KPa in the frequency range of 0.01 Hz to 0.1 Hz, form better attachment to the undergarment whether they are of cotton or microfiber material.

FIGS. 9A and 9B show graphs of the bonding compliance values and debonding compliance values, respectively.

Figure 10B:
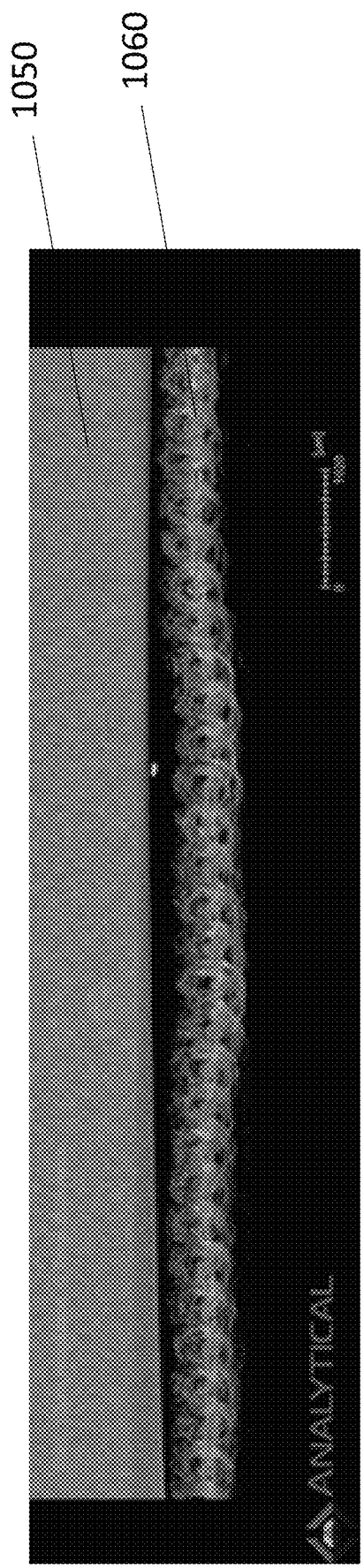
FIG. 10B is a microCT image showing the adhesive of Sample 6 bonded to a portion of a microfiber undergarment.
Figure 11A:
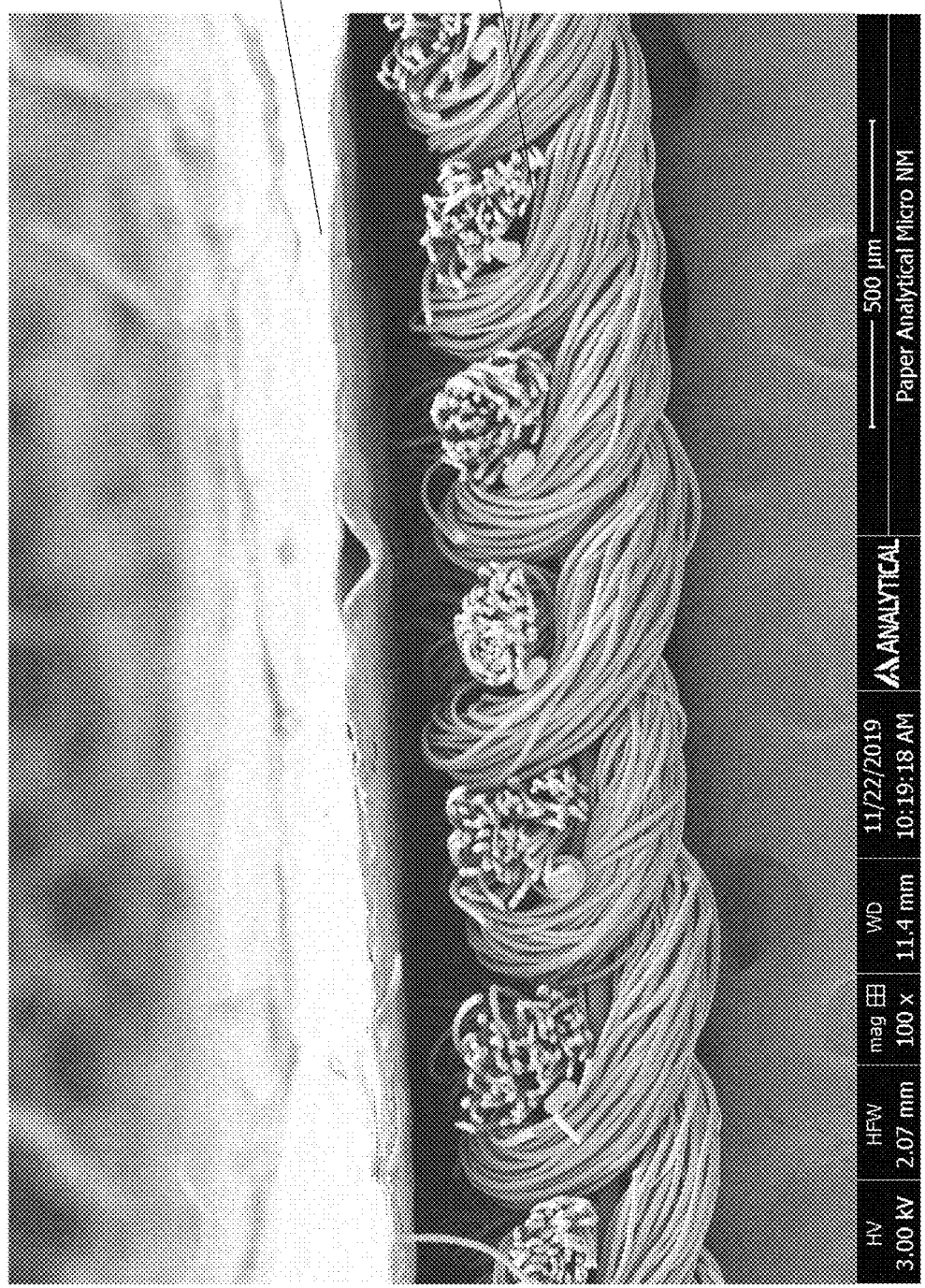
Figure 11B:
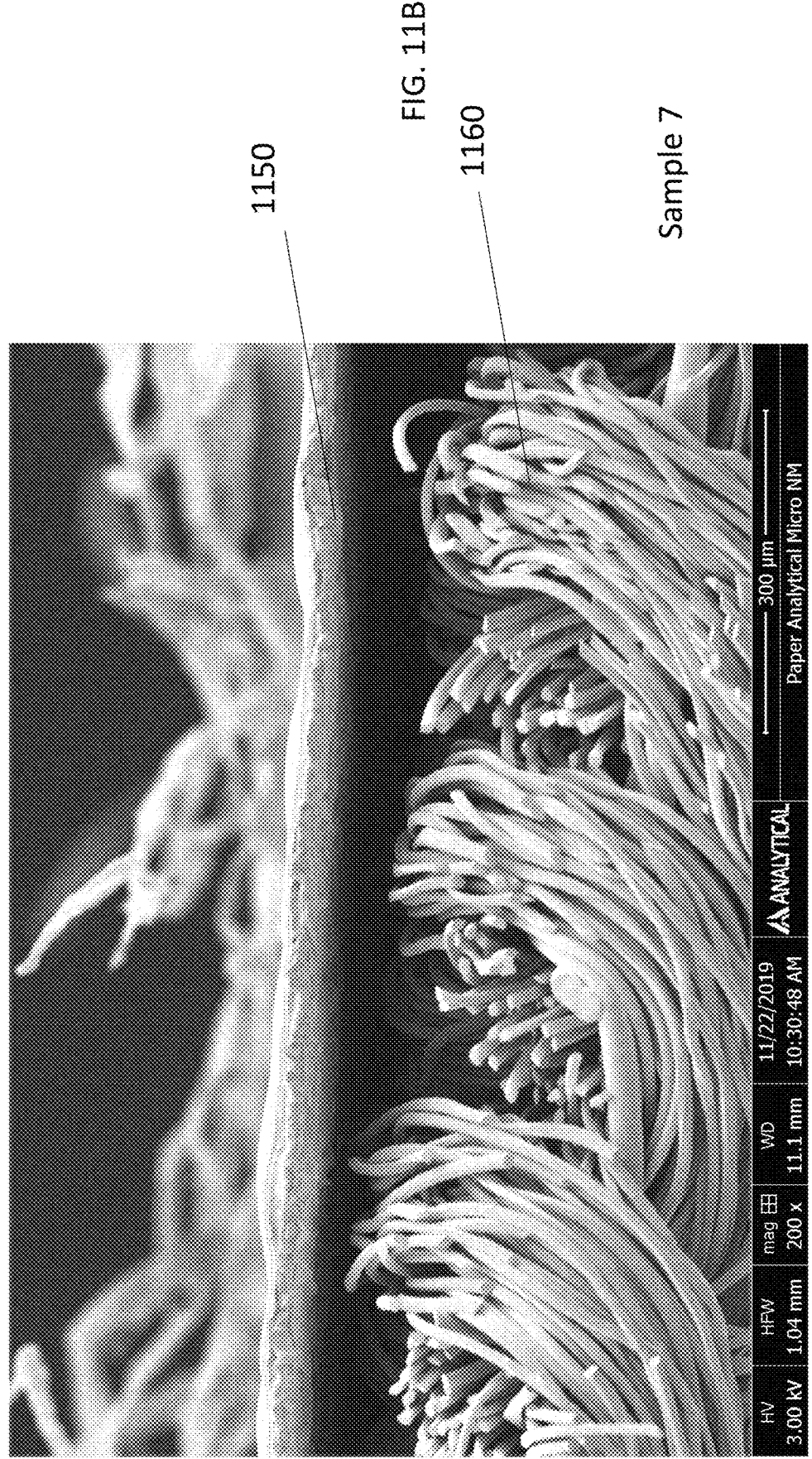
Figure 11D:
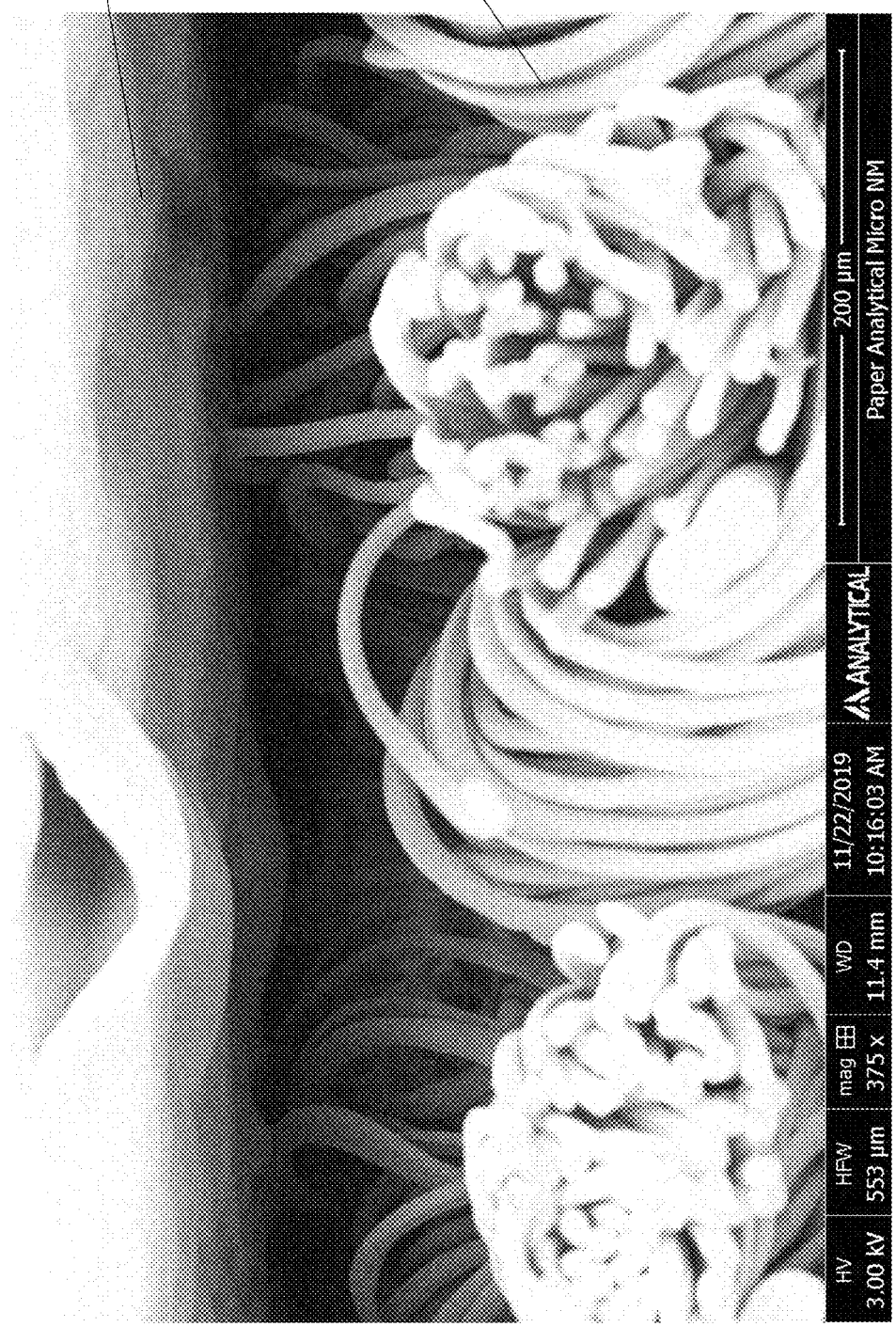
Figure 12B:
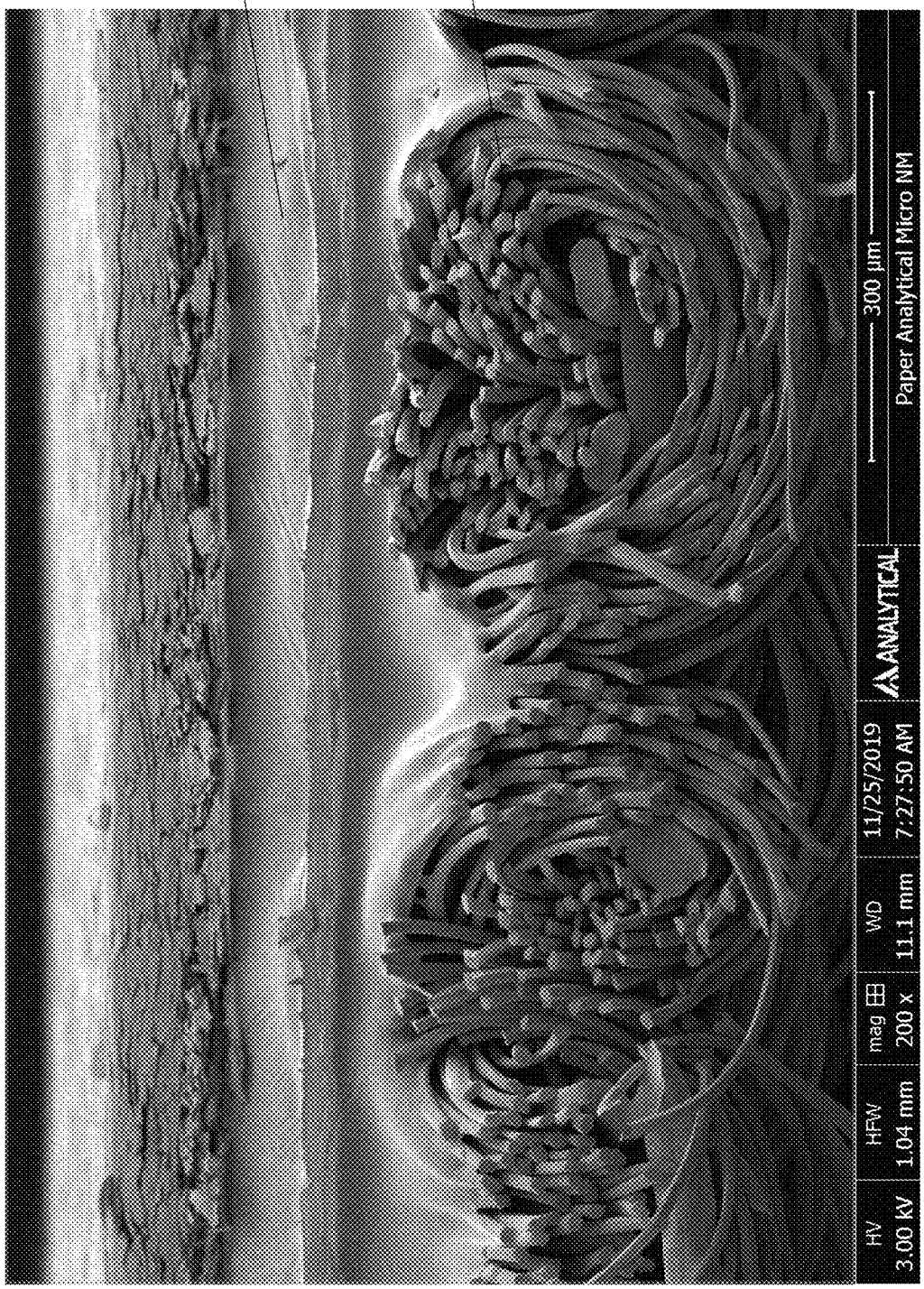
Figure 12C:
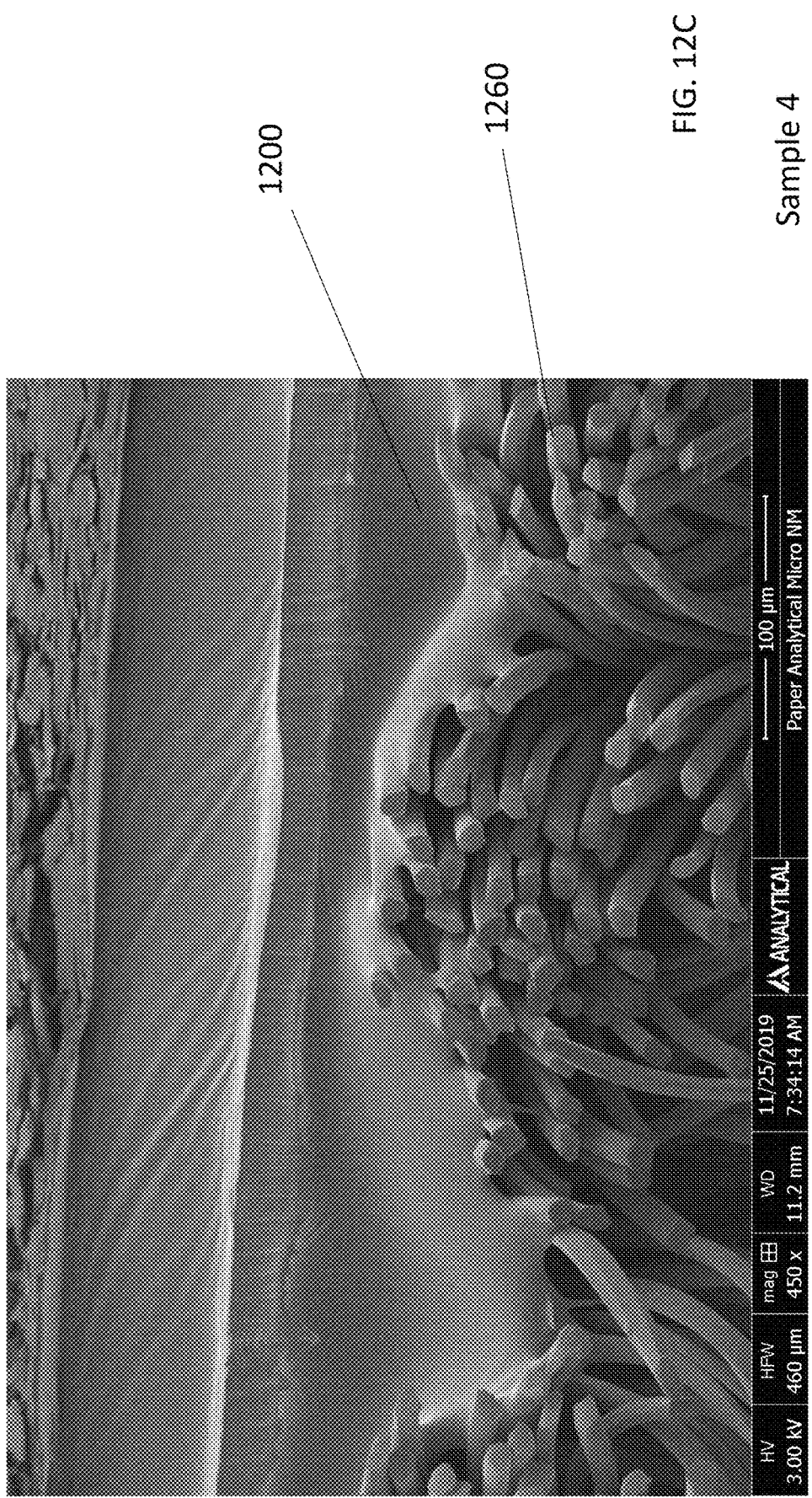
Figure 12D:
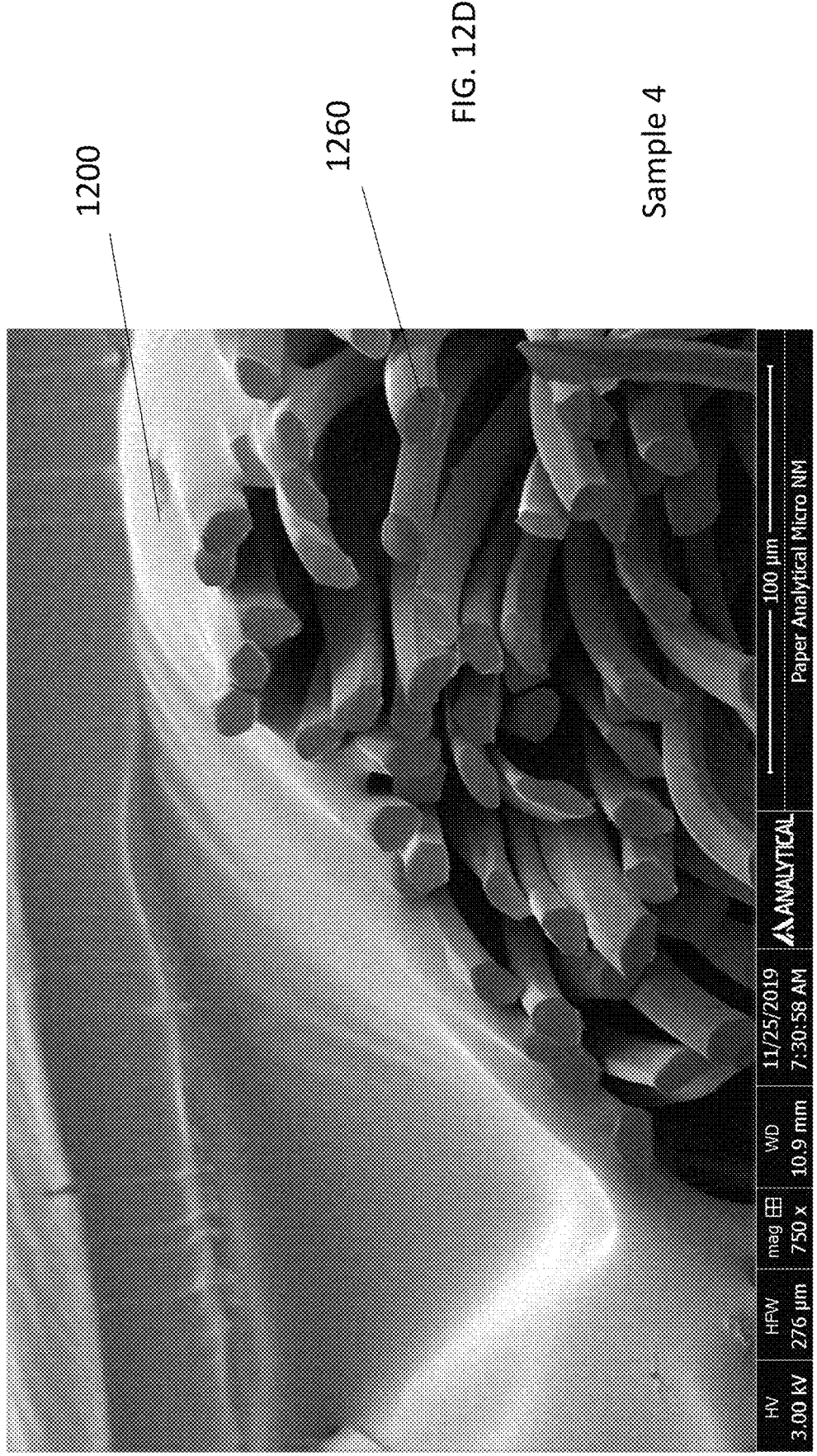

FIGS. 10A and 10B show microCT images of Samples 1 and 6, respectively, and their attachment to a microfiber underwear substrate. As shown, in FIG. 10A, there is no visual gap between adhesive 1000 and a microfiber underwear substrate 1010. In contrast, in FIG. 10B, there is a substantial gap between adhesive 1050 and a microfiber underwear substrate 1060. And, the gap exists the full length in the analyzed microCT image.

FIGS. 11A-11D show SEM images of Sample 7 and its attempt at bonding to a portion of a microfiber undergarment. A cross section of adhesive 1150 and microfiber undergarment 1160 was taken to show how the adhesive 1150 only bonds to a portion of the fibers in the undergarment 1160. Specifically in FIGS. 11C and 11D, the adhesive 1150 contacts portions of fiber bundles at high points in the undergarment 1160. For the sake of facilitation, the undergarment comprises bundles of fibers which are woven with other bundles of fibers. So, each fiber bundle has a high point where it crosses over a fiber bundle running in a direction perpendicular to itself and low points where it crosses under the next adjacent fiber running perpendicular to itself. The adhesive 1150 is shown attached, to some extent to the high points of the fiber bundles.

FIGS. 12A-12D show SEM image of Sample 4 and how it bonds to a portion of a microfiber undergarment 1250. In contrast to the adhesive 1150 (shown in FIGS. 11A-11D), adhesive 1200 is attached not only to the high points of the fibers but also exhibits more attached surface area to the various fiber bundles. In the images provided by FIGS. 12A-12D, the adhesive 1200 flows to such an extent that, in cross-section under SEM, there is no gap between the adhesive 1200 and fibers which are oriented perpendicular to the plane of the image—in contrast to the images of FIGS. 11A-11D. So, the adhesive 1200 is disposed on these fibers such that a portion of their circumference at the plane of the image is coated with adhesive. And the adhesive 1200, as shown, can bond to the circumference of the fibers such that the adhesive flows between adjacent fibers which are perpendicular to the plane of the image.

Absorbent Articles

The adhesives of the present disclosure can be utilized in a myriad of absorbent articles to attach the article to the undergarment of a user or to an outer shell of material as in the case with disposable inserts. Exemplary articles where the adhesives of the present disclosure may be utilized are menstrual pads, catamenial pads, incontinence pads, male incontinence guards, liners, absorbent inserts for durable panties, absorbent inserts for disposable diapers, and the like. The adhesives of the present disclosure may be a removable, repositionable adhesive, similar to one of the samples available, inter alia, through the 3M corporation of St. Paul, Minn.

Generally, absorbent article manufacturer's purchase adhesives from adhesive suppliers rather than formulate/blend the adhesives themselves. In such instances, an adhesive supplier may create an adhesive within the scope of the present disclosure and subsequently apply the adhesive to a material web, e.g. film. The adhesive manufacturer may then supply the film with the adhesive applied thereto to the absorbent article manufacturer. The absorbent article manufacturer, after obtaining the film with the adhesive applied thereto, may manufacture at least one of feminine hygiene articles, adult incontinence pads, male incontinence guards, absorbent liners or absorbent inserts for durable panties and/or disposable diapers or combinations thereof.

Similarly, absorbent article manufacturers producing at least one of feminine hygiene articles, adult incontinence pads, male incontinence guards, absorbent liners or absorbent inserts for durable panties and/or disposable diapers or combinations thereof, may obtain adhesives of the present disclosure from adhesive suppliers. Subsequently, the absorbent article manufacturer may apply the adhesive to a backsheet and/or a portion of a garment-facing surface of the absorbent article.

Absorbent articles of the present disclosure comprise a topsheet, a backsheet, and an absorbent system disposed between the topsheet and the backsheet. The topsheet and the backsheet are peripherally joined either directly or indirectly generally outboard of the absorbent system. Adhesives of the present disclosure are disposed on a garment-facing side of the absorbent article which, at least in part, comprises at least a portion of the backsheet.

Any suitable pattern of the adhesives of the present disclosure may be utilized. Exemplary arrangements for adhesives of the present disclosure on the backsheet of an absorbent article are shown in FIG. 13. FIG. 13 represents an exemplary absorbent article 10 according to the present disclosure as seen from a garment-facing side. The absorbent article 10 has a longitudinal axis 80 a transversal axis 90, a front end region 50 a back end region 60 and a central region 70. The lines 20 and 30 illustrate the approximate boundaries between the front end region 50 and the central region 70 and the back end region 60 and the central region 70, respectively.

Adhesives 100 as described herein (cross-hatched portions in the front end region 50 and the back end region 60), may be disposed on the garment-facing surface in the front end region 50 and the back end region 60. Additionally, the adhesives 100 may be disposed in the central region 70. As shown, the adhesive 100 can have an adhesive length 40 in the front end region 50, and the front end region 50 can have a front end region length 45. A ratio of the adhesive length 40 to the front end region length 45 was disclosed previously herein. Additionally, the adhesive 100 in the back end region 60 can have a similar ratio of adhesive length to back end region length as the front end region 50. Alternatively, the back end region adhesive length can be different than the front end region adhesive length 40.

Additionally, the adhesive 100 may extend from end edges 190 of an absorbent core longitudinally toward the transversal axis 90. And, the adhesive 100 may extend from longitudinal side edges 180 toward the longitudinal axis 80.

It is worth noting that while side panels or "wings," as they are called in the feminine hygiene pad context, are not shown in FIG. 13, absorbent articles of the present disclosure may comprise wings. The intent of the wings is to protect the sides of the undergarments and typically wings fold along the crotch area of the underwear and are attached below it. Wings can be provided as separate pieces and be attached to the article, typically a pantyliner or a sanitary napkin, or they can be integral with the materials of the absorbent articles, e.g., by being an integral extension of the topsheet, the backsheet, or of both.

Additionally, it is worth noting that for the purpose of the present invention, wings are not considered part of the backsheet (even when they are formed by an integral extension of it). Wings typically include adhesive on the backsheet side in order to affix them below the crotch of the underwear, and any typical adhesive distribution pattern can be used in conjunction with the absorbent articles of the present disclosure. Some examples include a continuous application or a patterned application. A patterned application of adhesive on the wings may provide the same benefits as the patterned adhesive application on the backsheet of the article when the article is removed thus reducing the risk of tearing the wing material.

As noted previously, the adhesives of the present disclosure may comprise pre-formed adhesives. FIGS. 14A-14D show conventional coated adhesive (applied in liquid/molten form) onto a backsheet versus pre-formed adhesives shown in FIGS. 15A-15D.

Regarding FIGS. 14A-14D, the scanning electron microscope (SEM) images were taken at 30×, 100×, 250× and 500× magnification, respectively. As shown, the conventional adhesive does not comprise any discernable pattern in any of the images. Instead shown are some random air bubbles and what appear to be areas of increased caliper. In the 250× and 500× images, striations in the adhesive appear; however, while these striations generally have a uniform direction from left to right in the image, the striations are random in length and direction to some extent.

Regarding FIGS. 15A-15D, the SEM images were taken at 30×, 100×, 250× and 500× magnification, respectively. As shown, the pre-formed adhesive, specifically tape in this instance, there appears to be air bubbles and other asperities. However, in contrast to the images of FIGS. 14A-14D, a pattern in the adhesive is clear even at 30× magnification. The arrangement of dots/nodes in a repeating pattern is prevalent in the image. At the higher resolutions, these nodes appear to be depressions and form what appears to be a quilted pattern.

Figure 16:
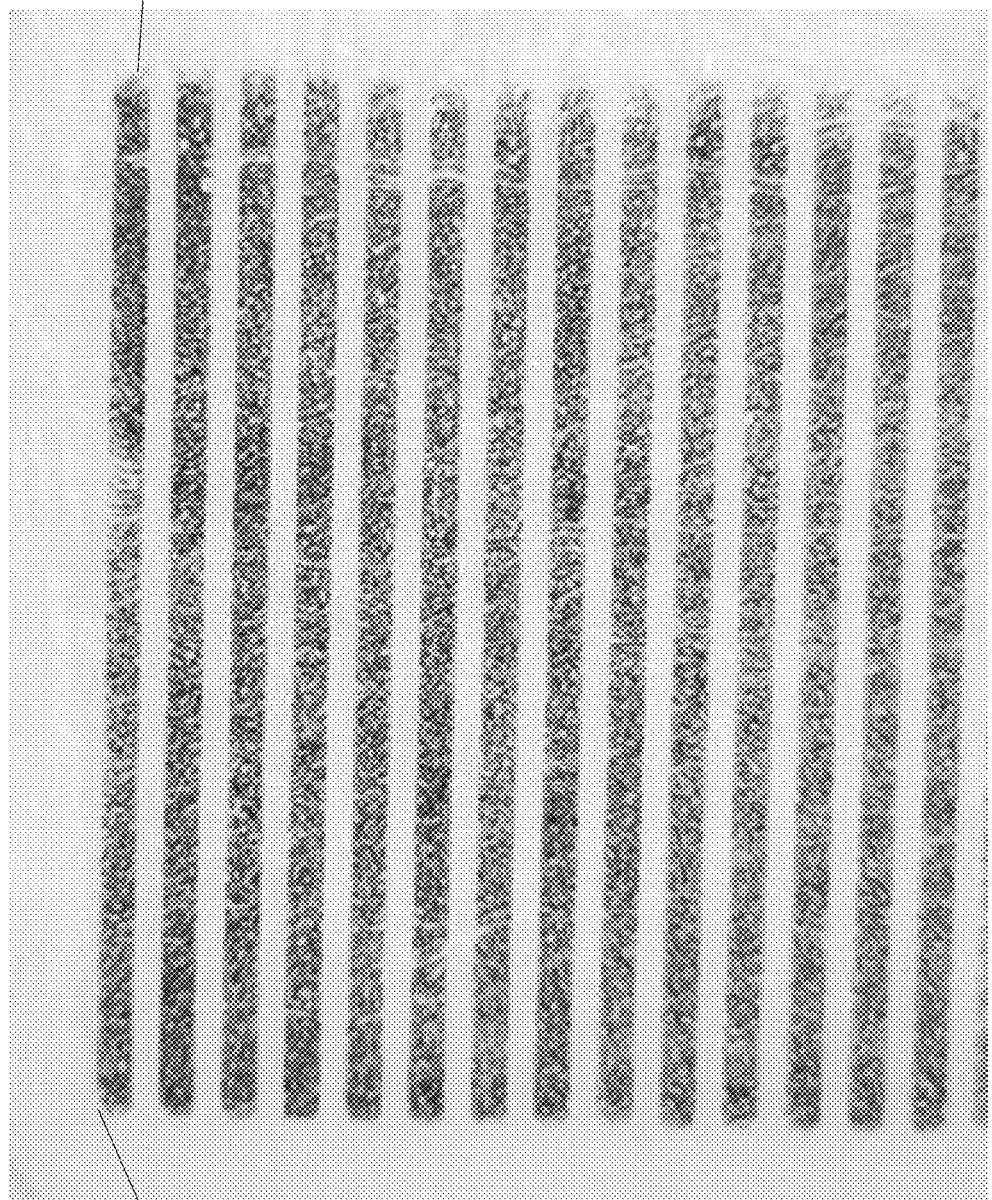
FIG. 16 is a picture of a backsheet of an absorbent article with the adhesive highlighted in black, wherein the adhesive is applied via conventional application.

FIG. 16 shows an adhesive on the backsheet of an absorbent article highlighted in black. As shown, the adhesive comprises a plurality of stripes shown from left to right in the image. Each of the stripes comprises a leading portion 2610 and a trailing portion 2620 and a central portion disposed between the leading portion 2610 and the trailing portion 2620. The leading portion 2610 and the trailing portion 2620 each comprise about one third of the overall length of the adhesive stripe. The trailing portion 2620 generally has a lower basis weight than does the leading portion 2610 and the central portion. For example, the basis weight in the central portion can have a basis weight which varies on average by no more than about 20 than about 15%, or no more than about 10%, such as by no more than about 5% over the length of the central portion. The trailing portion 2620, on the other hand, can gradually decrease from the average basis weight of the central portion to zero. And similarly, the leading portion 2610 can have a higher basis weight than the central portion.

Figure 17:
FIG. 17 is a picture of a backsheet of an absorbent article with the adhesive highlighted in black, wherein the adhesive is applied as a plurality of pre-formed portions.

In contrast to the adhesive of FIG. 16, in FIG. 17, pre-formed adhesive is shown on the backsheet of an absorbent article. Similar to the adhesive of FIG. 16, the pre-formed adhesive of FIG. 17 may comprise a leading portion 2710 and a trailing portion 2720 along with a central portion disposed therebetween. And similarly, the leading portion 2710 and the trailing portion 2720 may each comprise about a third of the overall length of the pre-formed adhesive. However, unlike the adhesive of FIG. 16, the pre-formed adhesive of FIG. 17 has a relatively uniform basis weight throughout the leading portion 2710, central portion and trailing portion 2720. Specifically, the trailing portion 2720 does not gradually decrease to zero as in the trailing portion 2620 of FIG. 16.

It is also worth noting that in FIGS. 16 and 17, the leading portions and trailing portions are shown extending generally in a transverse direction on the backsheet of the absorbent article. However, the above distinction applies to adhesive which is applied generally in a longitudinal direction. In such constructions, the leading portion and the trailing portion would be oriented generally parallel to the longitudinal axis. And similar to the foregoing, adhesive which are applied in molten/liquid form will have a trailing portion which gradually decreases basis weight to zero while the pre-formed adhesives will comprise a trailing portion which has a generally uniform basis weight as noted regarding the central portion and a trailing portion which does not gradually decrease in basis weight to zero.

The use of pre-formed adhesive can be determined via visual inspection of the leading portions and trailing portions of the adhesive on the backsheets of the absorbent articles. Where the pre-formed adhesive is a tape, regular microscopy or close visual inspection may be utilized to determine whether a substrate is disposed between two layers of adhesive.

The topsheet may comprise any suitable substrate. Some examples include films, nonwovens, laminates of films and nonwovens, laminates of films and films, laminates of nonwovens and nonwovens, composites of films and nonwovens, composites of films and films, and composites of nonwovens and nonwovens. A laminate of two different materials regards the combination of the materials after each has been made. For example, a film web may be combined with a nonwoven web via mechanical processing, adhesives, ultrasonic or fusion bonding, etc.

A composite of two different materials regards the combination of the materials when one of the materials is made. For example, a semi-molten film web may be extruded onto a nonwoven. This composite material will not need additional bonding as the semi-molten material is able to flow—to some extent—into the interstices of the nonwoven fibers.

Regardless of the form of the topsheet, the topsheet is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

Topsheets of the present disclosure may be provided with texture, such as protrusions or depressions. The protrusions and/or depressions may be treated hydrophobically or hydrophilically as desired. Some suitable examples of protrusions and depressions and their respective treatments and methods of doing so are described in U.S. Patent Publication Nos. US2017/0258955; US2018/0071151; US2017/0027774; US2017/0029994; US2018/0216269; US2019/0374405; US2019/0380887; and US2019/0298587.

As noted previously, the absorbent articles of the present disclosure comprise an absorbent system disposed between the topsheet and the backsheet. The absorbent system may comprise several layers. For example, a layer of material which is most proximal to the topsheet—often termed acquisition layer or secondary topsheet—may be utilized to quickly acquire liquid insults from the topsheet.

The secondary topsheet or acquisition layer may comprise any suitable material. Some examples include films and nonwovens or laminates or composites thereof. Film based secondary topsheets, if utilized correctly, can provide a good barrier against rewet; however, care must be taken to ensure that the film secondary topsheet comprises adequate fluid transport openings to allow acquired liquid insults from the topsheet to pass to one or more storage layers.

Nonwoven based secondary topsheets may also be utilized. For example, secondary topsheets of the present disclosure may comprise a tissue layer or a nonwoven, such as carded resin-bonded nonwovens, embossed carded resin-bonded nonwovens, high-loft carded resin-bonded nonwovens, carded through-air-bonded nonwovens, carded thermo-bonded nonwovens, spunbonded nonwovens, and the like. A variety of fibers can be used in the secondary topsheet or acquisition layer, including natural fibers, e.g. wood pulp, cotton, wool, and the like, as well as biodegradable fibers, such as polylactic acid fibers, and synthetic fibers such as polyolefins (e.g., polyethylene and polypropylene), polyesters, polyamides, synthetic cellulosics (e.g., RAYON®, Lyocell), cellulose acetate, bicomponent fibers, and blends thereof. The basis weight of the secondary topsheet or acquisition layer can vary depending upon the desired application. Some suitable secondary topsheets are described in U.S. Patent Application Publication Nos. 2020/0306099, entitled "FLUID MANAGEMENT LAYER FOR AN ABSORBENT ARTICLE"; 2020/0315870, entitled "Fluid Management Layer For An Absorbent Article"; and 2020/0315861, entitled "Absorbent Layer For An Absorbent Article." Additional exemplary secondary topsheets are described in U.S. Pat. No. 10,532,123; U.S. Patent Application Publication Nos. US2019/0247244 and US2018/0098893.

The absorbent system may comprise, in addition to or independently thereof, an absorbent core. The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers. Other suitable absorbent core materials include absorbent foams such as polyurethane foams or high internal phase emulsion ("HIPE") foams. Suitable HIPE foams are disclosed in U.S. Pat. Nos. 5,550,167, 5,387,207, 5,352,711, and 5,331,015. The absorbent core can comprise superabsorbent materials such as absorbent gelling materials (AGM), including AGM fibers, as is known in the art. The absorbent core can therefore constitute a layer comprising superabsorbent material.

The absorbent core may comprise a blend of components as well and/or a myriad of layers. For example, a layer may comprise a mixture of cellulose (pulp) and AGM. Another layer may comprise a foam layer, e.g. a HIPE foam or a polyurethane foam layer. Additional HIPE foam layer configurations are possible. For example, a HIPE foam or portions thereof, may be deposited on a nonwoven web. Such structures are defined in additional details in U.S. Patent Application Nos. US2015/0313770; US2015/0335498; US2015/0349391; US 2017/0071795; US2017/0119587; and US2017/0119597. Additional structures are described in U.S. Pat. Nos. 10,045,890; 9,956,586; and 10,016,779. As yet another example, an absorbent core layer may comprise a nonwoven web upon which AGM is deposited and secured thereto by adhesive. Such processes and structures are described in additional detail in U.S. Pat. Nos. 8,187,240; 7,838,722; 8,735,645; 8,784,594; and 9,492,334.

A myriad of combinations of the above layers are possible. For example, a nonwoven/AGM layer may be joined to a cellulose layer and/or a HIPE foam layer. As another example, a cellulose layer may be joined with a HIPE foam layer and/or a polyurethane foam layer. As yet another example, a layer comprising a mixture of cellulose and AGM may be joined with a HIPE foam layer and/or a polyurethane foam layer. Where larger absorbent cores may be required, for example in the adult incontinence context, any of the foregoing combinations may be utilized in conjunction with one another and/or duplicated. For example, a nonwoven/AGM layer may be joined to a cellulose layer which is joined to another cellulose layer, which is joined to a nonwoven/AGM layer.

Additional examples of absorbent cores include those having multiple layers. In one example an absorbent core may comprise a distribution layer which is substantially free of AGM, a superabsorbent layer which is substantially free of pulp, a second distribution layer substantially free of AGM and a second superabsorbent layer substantially free of pulp. These layer may be arranged in any suitable manner. For example, the first distribution layer may be disposed proximal to a secondary topsheet which the first superabsorbent layer is disposed between the first distribution layer and the second distribution layer. The second superabsorbent layer may be disposed between the second distribution layer and the backsheet. Alternatively, the second superabsorbent layer may be disposed between the first superabsorbent layer and the second distribution layer. Or still in other examples, the first distribution layer may be disposed between the first superabsorbent layer and the second superabsorbent layer. Examples of such absorbent core constructions are provided in additional detail in U.S. Patent Application Publication Nos. 2020/0375810 A1; 2019/0314212 A1; 2018/0098893 A1 and 2018/0098896 A1.

For some absorbent articles, the absorbent core can be relatively thin, less than about 5 mm in thickness, or less than about 3 mm, or less than about 1 mm in thickness. Thickness can be determined by measuring the thickness at the midpoint along the longitudinal centerline of the pad by any means known in the art for doing while under a uniform pressure of 1.72 kPa. The overall thickness of the absorbent article can similarly be relatively thin. In some instances, pantiliners can range from 1.5 mm to about 3.0 mm Menstrual pads can have a thickness ranging from 2.0 mm to about 3.5 mm Adult incontinence pads can have a thickness of from about 2.6 mm to about 6.5 mm.

Regarding AGMs, polyacrylate based materials, typically partially neutralized polymers, are commonly incorporated in absorbent articles and are known as superabsorbent polymers or superabsorbents and are crosslinked. The polyacrylate material has neutralized, typically with sodium, carboxylate groups hanging off the main polymer chain. In contact with water, the sodium detaches and goes in solution, leaving only carboxyl ions. Being negatively charged, these ions repel one another so that the polymer unwinds and absorbs more and more water, which is instead attracted by the carboxyl ions, as further carboxyl ions become available. The hydrogen in water is trapped by the polyacrylate due to the atomic bonds associated with the polarity forces between the atoms. The cross-links, which bridge different polymer chains, lead to a three-dimensional structure, which upon liquid absorption constitutes the swollen gel.

The absorbent gelling material which can be comprised in the absorbent core can be selected among the polyacrylate based polymers described in the European Patent Application EP 05023061.4, filed on 21 Oct. 2005, in the name of The Procter and Gamble Company. As explained in the referenced application, polyacrylate based materials being very slightly crosslinked, or substantially not crosslinked at all, incorporated in absorbent articles for the absorption of proteinaceous or serous body fluids such as for example menses, blood, plasma, vaginal secretions, and also mucus or milk, but particularly menses or blood, provide an improved absorption and retention capacity for such body fluids, and an improved absorption rate as well, compared to traditional crosslinked superabsorbents.

The absorbent gelling materials can be typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

Absorbent cores may include a core wrap i.e. a thin layer of fluid pervious material (usually a tissue paper or a think nonwoven layer) which wraps the core in order to preserve its integrity during manufacturing of the article and during its use.

The absorbent article can comprise further components such as side cuffs, typically found in incontinence pads, or side wings or side flaps, typically found in sanitary napkins. These side wings or side flaps may comprise one or more adhesive portions described herein.

The absorbent articles herein are preferably disposable after a single use and are usually commercialized in packages comprising multiple units which in some cases can be individually wrapped.

The backsheet of the absorbent articles of the present disclosure is the outer layer of the article on a garment facing side. In case the outer layer of the absorbent article on its garment-facing side is a composite material (such as a laminate of a film and a nonwoven material) for the purpose of the present disclosure, the term "backsheet" indicates exclusively the outermost layer of the layers forming said composite material. For example, in the case of a NW/PE film laminate, with the PE film being the outer layer on which garment facing surface the fastening adhesive is applied, for the purpose of the present disclosure the term "backsheet" indicates exclusively said outer PE film layer.

The backsheet of the absorbent articles of the present invention is a plastic film and is preferably flexible and soft. As used herein, the term "flexible and soft" refers to materials which are compliant and will readily conform to the general shape and contours of the human body and will give the users a pleasant tactile feel on the skin. The backsheet prevents the exudates absorbed and contained in the absorbent core from wetting articles which contact the absorbent article such as bedsheets, pants, pajamas and undergarments. The backsheet can also be vapor permeable ("breathable"), while remaining fluid impermeable. In this case typically microporous plastic films are used which are water vapor permeable while remaining essentially impermeable to liquids.

The backsheet can be a plastic film having a basis weight of less than 40 gsm or less than 30 gsm or less than 24 gsm or less than 18 gsm or less than 15 gsm or less than 13 gsm. Any type of plastic film can be used as backsheets according to the present invention. Suitable films can be formed by a thermoplastic polymeric material and can be obtained by known film making processes. Plastic films can be selected from single layer or multilayer films which are obtainable for example through a single layer extrusion or a multilayer co-extrusion process. For example, US2014/0248484 discloses a method for producing thin plastic films usable as backsheets in the present invention wherein an initial film web made of a thermoplastic polymer material containing a polyethylene matrix, and 1 to 70 parts by weight of polypropylene per 100 parts by weight of polyethylene matrix, is, after being heated, guided through a cooled roll gap whereby the initial film web is heated only until the polyethylene matrix material melts but below the melting temperature of the polypropylene.

The plastic films usable herein as backsheets can comprise a single polymer or a blend of different polymers. In addition to polymers, the plastic films of the present disclosure can comprise additives such as for example pigments, dyes, chemical additives such as light protectors, antioxidants, and inert materials such as titanium oxide, calcium carbonate, or also kaolin, diatomaceous earth, or mixtures thereof. The presence of an inert component, typically calcium carbonate, can increase the physical properties of the polymeric film, particularly heat resistance, which can be beneficial in the context of the present invention, where backsheet films are typically heat sealed along the perimeter to the topsheet of the absorbent article. Also, inert materials are sometime included in plastic films which are mechanically stretched when cold so that the inert particles form a network of channels which allows the passage of water vapor while maintaining a good permeability. Such films are normally identified as "microporous films" are suitable as backsheets in the present invention and they can provide improved breathability in the absorbent articles (as known in the art).

The plastic films usable herein as backsheets of the present invention are preferably thermoplastic polyolefin-based film. The plastic film for of the present invention can be for example a polyethylene (PE) based film, a polypropylene based (PP) or a PE/PP blend-based film.

When it is mentioned that a film is "based" on a polymer (e.g. PE) or on a mixture of polymers (e.g. PE/PP blend), it is intended that the majority of the mass of the film is constituted by the polymer(s) of which is based on, preferably more than 80% wt. even more preferably more than 90% wt. The remaining mass of the film can be formed by other polymers and customary film additives as known in the art.

As mentioned above, the backsheet forms the garment-facing surface of the absorbent article on which the fastening adhesive is placed. Prior to use of the absorbent article, the areas being coated with PFA are typically protected from contamination and from adhering to another surface where this is not desired, by a protective cover means such as a silicone coated release paper, a silicone coated plastic film or any other easily removable cover. The protective cover means can be provided as a single piece or in a multitude of pieces, e.g. to cover individual adhesive areas (e.g. on the backsheet and on the wings). The protective cover means can also perform other functions such as provide individualized packaging for the article or provide a disposal function as known in the art. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

The adhesives of the present disclosure which are disposed on the garment-facing surface of the absorbent article which can include a portion of the backsheet and/or a portion of wings/side flaps. Adhesives may be evaluated against the characteristics of the present disclosure prior to their application on the backsheets of their respective absorbent articles.

Table 3 is provided for the convenience of the reader. Table 3 includes a non-exhaustive list of properties as well as a non-exhaustive list of corresponding values for each of the properties discussed herein for the PFA's of the present disclosure. There is no requirement that the PFA's of the present disclosure exhibit all of these properties.

TABLE 3

| Property | Value |
| --- | --- |
| Tan delta -1 | 0.28 to 1.2 |
| Tan delta -2 | 0.25 to 1.9 |
| Storage modulus -1 | 1 kPa to 84 kPa |
| Storage modulus -2 | 40 to 300 kPa |
| Yield stress | 32 kPa to about 100 kPa |
| Relaxation time | 100 seconds or less |
| Surface Energy | 10 mJ/m² to 24 mJ/m² |
| Polar component | 1 percent to 9 percent |

ADDITIONAL EXAMPLES

Example A: A method of making a disposable absorbent article having a wearer-facing surface and a garment-facing surface, a front end region, a back end region, and a central region disposed between the front end region and the back end region, the method comprising the steps of: obtaining a topsheet; obtaining a backsheet; obtaining an absorbent system; combining the topsheet, backsheet, and absorbent system such that the absorbent system is disposed between the topsheet and the backsheet, and joining the topsheet and the backsheet together outboard of the absorbent system; obtaining pre-formed adhesive portions; and attaching one side of the pre-formed adhesive portions to the backsheet.

Test Methods

Surface Energy/Contact Angle Method

Contact angles on substrates are determined using a goniometer and appropriate image analysis software (a suitable instrument is the DSA100 Drop Shape Analyzer, Kruss GmbH, Hamburg, Germany, or equivalent) fitted with a gas tight syringe and steel needle capable of dispensing 1.0 uL drops. Two test fluids are used: Type II reagent water (distilled) in accordance with ASTM Specification D1193-99 and 99+% purity diiodomethane (both available from Sigma Aldrich, St. Louis, MO). Contact angles from these two test fluids can further be used to calculate surface energy based on the Fowkes Theory. All testing is to be performed at about 23° C.±2° C. and a relative humidity of about 50%±2%.

Contact angle measurements are made on test specimens taken from the raw material or obtained from a material layer removed from an absorbent article. When excising the material layer from an absorbent article, use care to not impart any contamination or distortion to the layer during the process. When the test location is on an adhesive, do not remove any protective cover that may be present until the measurement is to be made in order to decrease the likelihood of contaminating the adhesive layer. The test specimen must be of an appropriate size such that it fits onto the stage of the goniometer and can accommodate any potential spreading of the applied test fluid. Prepare enough test specimens for a total of twenty test locations (ten locations for each test fluid).

Set up the goniometer on a vibration-isolation table and level the stage according to the manufacturer's instructions. The video capture device must have an acquisition speed capable of capturing at least 10-20 images from the time the drop of test fluid hits the surface of the specimen to the time it cannot be resolved from the specimen's surface. A capture rate of 900 images/sec is typical. Depending on the hydrophobicity/hydrophilicity of the specimen, the drop may or may not rapidly wet the surface of the test specimen. If the test specimen is capable of absorbing the test fluid at a slow rate, the images should be acquired until no more than 2% of the volume of the drop is absorbed into the specimen. If the test specimen is capable of absorbing the test fluid quickly, the first resolved image should be used if the second image shows more than 2% volume loss.

Place the specimen on the goniometer's stage and adjust the hypodermic needle to the distance from the surface recommended by the instrument's manufacturer (typically 3 mm). If necessary, adjust the position of the specimen to place the test location under the needle tip. Focus the video device such that a sharp image of the drop on the surface of the specimen can be captured. Start the image acquisition. Deposit a 1.0 μL±0.05 μL drop of diiodomethane onto the specimen. If there is visible distortion of the drop shape due to movement, repeat at a different, but equivalent, test location. Make two angle measurements on the drop (one on each drop edge) from the image at which there is no more than a 2% loss in drop volume. If the contact angles on two edges are different by more than 4°, the values should be excluded and the test repeated at an equivalent location on the specimen. Identify nine additional equivalent sites on the specimen and repeat for a total of 10 measurements (20 angles). Calculate the arithmetic mean for all replicates and report as Contact Angle with Diiodomethane to the nearest 0.01°. In like fashion, measure the contact angle with water as the test fluid, and report as Contact Angle with Water to the nearest 0.01°.

To calculate surface energy, the contact angle for both diiodomethane and water must be tested as described above. The value of contact angle for each test fluid is then used, along with additional information about each test fluid, to make calculations using the Young-Dupre equation and the Fowkes Theory as follows:

$$W_{sl}=\gamma_l(\cos\theta+1) \quad\quad \text{The Young-Dupre equation (Eq 1)}$$

$$W_{sl}=2[(\gamma_l^D*\gamma_s^D)^{0.5}+(\gamma_l^P*\gamma_s^P)^{0.5}] \quad\quad \text{The Fowkes Theory (Eq. 2)}$$

Combining Eq 1 and Eq 2 to get Eq 3

$$\frac{\gamma_l(\cos\theta+1)}{2}=(\gamma_l^D*\gamma_s^D)^{0.5}+(\gamma_l^P*\gamma_s^P)^{0.5}$$

where:
$W_{sl}$=work of adhesion
$\theta$=the average contact angle for the respective test fluid on the test specimen
$\gamma_l$ and $\gamma_s$=the surface tension of the test liquid and test specimen, respectively, in mJ/m²
$\gamma^D$ and $\gamma^P$=the dispersive and polar components of the surface tension, respectively, in mJ/m² and the properties of the test fluids are as follows:

| Solvent | Surface Tension ($\gamma_l$) (mJ/m²) | | |
| --- | --- | --- | --- |
| | Dispersive ($\gamma_l^D$) | Polar ($\gamma_l^P$) | Total ($\gamma_l$) |
| Diiodomethane | 50.8 | 0.0 | 50.8 |
| Water | 26.4 | 46.4 | 72.8 |

Eq 3 can be further simplified when a purely dispersive solvent such s diiodomethane is used since the polar component is zero and $\gamma_l^D = \gamma_l$, as follows:

Eq 4 (Eq 3 simplified for a purely dispersive solvent)

$$\gamma_s^D = \frac{\gamma_l(\cos\theta + 1)^2}{4}$$

Using the surface tension values from the table and θ (measured) for diiodomethane, Eq 4 can be solved for the dispersive component of surface energy ($\gamma_s^D$) and reported to the nearest 0.01 mJ/m². Now using the values from the table and θ (measured) for water, along with the previously calculated value for $\gamma_s^D$, Eq 3 can be solved for the polar component of surface energy ($\gamma_s^P$) and reported to the nearest 0.01 mJ/m². Total surface energy of the test specimen ($\gamma_s$) is calculated as the sum of $\gamma_s^D + \gamma_s^P$ and reported to the nearest 0.01 mJ/m². Now calculate surface polarity by dividing the polar component of surface energy ($\gamma_s^P$) by the total surface energy ($\gamma_s$), then multiplying by 100 and reporting to the nearest 0.01%.

Frequency Sweep—Oscillatory Rheometry Test Method

The Oscillatory Rheometry Test Method is used to measure the Storage Modulus and the Loss Factor (also known as tan delta) of adhesive tapes or hot melt adhesive compositions. A rotational rheometer (such as DHR3 or ARES G2, TA Instruments, New Castle, DE, USA, or equivalent) capable of sample temperature control with a precision equal to or exceeding 0.5 degrees C. over at least the range of 0 degrees C. to 150 degrees C. The rheometer needs to have a normal force control system to enable the axial force control on the specimen with an accuracy of 0.1 N. The rheometer is operated in a parallel plate configuration with 25 mm stainless steel parallel-plate tooling for hot melt adhesives and 20 mm for adhesive tapes or 8 mm when the adhesive tape width is smaller than 20 mm Adhesive Tapes Specimen Preparation For adhesive tapes individual specimens for measurement are punched with a circular sample cutter of 20 mm diameter or 8 mm if the adhesive tape width is smaller than 20 mm. The release films are removed, and the measurement specimen is placed centered on the lower plate of the rheometer at 23+/−0.5 degrees C. The upper rheometer plate is lowered until it gets in contact with the adhesive tape. The upper plate is pressed with approximately 5-10 N axial force at 23+/−0.5 degrees C. for about 30-90 sec onto the adhesive tape to ensure full contact. After that the axial force control is set to 1.0 N and be maintained within ±0.1 N of force during the experiment.

Hot Melt Specimen Preparation:

The rheometer is heated to 150 degrees C., the adhesive or polymer composition is introduced in the rheometer, the gap is set to 1050 μm, excess protruding sample is trimmed, and the gap is then set to 1000 μm. (The axial force control of the rheometer is set to 0 N and be maintained within ±0.1 N of axial force during the experiment, thereby thermal expansion/contraction of the sample itself is compensated by adjusting the gap in order to avoid overfilling or underfilling in addition to the abovementioned compensation of the tooling.) The rheometer is then allowed to cool to 37 degrees C. or 25+/−0.5° C. if obtaining data for 25 degrees C.

Measurement:

The sample is equilibrated at 37 degrees C.+/−0.5 degrees C. (or 25+/−0.5 degrees C., if obtaining data for 25 degrees C.) for 300 s. An oscillatory frequency sweep with 0.1% strain is performed from 0.01-100 Hz [1/s] at 37 degrees C.+/−0.5 degrees C. (or 25+/−0.5 degrees C., if obtaining data for 25 degrees C.). In a logarithmic matter 10 points per decade are acquired (see frequency table).

Analysis:

From the frequency sweep, the storage modulus G' and the loss factor (tan delta) is calculated and recorded from 0.01 to 100 Hz for 10 frequencies per decade in a logarithmic matter. The storage modulus values are reported in kilopascal (KPa) to the nearest 0.01 KPa. The loss factor (also known as tan delta) are recorded to the nearest hundredth.

Extensional Test Method for Yield Stress

The Extensional Test Method is used to determine the Yield Stress for a specimen of an adhesive composition. A thin film specimen formed of adhesive composition is analyzed with a rotational rheometer fitted with a specialized fixture with counter rotating rollers, and the stress associated with extensional strain imparted is measured and recorded.

Instrumental Setup

A rotational rheometer (ARES G2, TA Instruments, New Castle, DE, USA, or equivalent) is fitted with a fixture that has counter rotating cylindrical metal rollers specifically designed for the interrogation of extension deformation of films. An example of a suitable fixture is the Extensional Viscosity Fixture, or EVF (EVF, TA Instruments, or equivalent). The rheometer is further fitted with a forced-convection oven FCO (FCO, TA Instruments, or equivalent) and cooling system (ACS 2, TA Instruments, or equivalent) capable of controlling temperate from at least −50 to 250° C. to a within a tolerance of 0.5° C.

Specimen Preparation

If the adhesive is mounted on a substrate, it must be separated before preparing it as a test specimen. This can be done by extracting the adhesive from the substrate with an organic solvent such as Tetrahydrofuran (THF) and evaporating the entire solvent afterwards gently at room temperature (20° C.-30° C.) to obtain the adhesive for test specimen preparation.

To prepare the test specimen approximately 2 g to 10 g of the adhesive composition is placed in a circular polytetrafluoroethane (PTFE) bowl with a flat bottom (diameter of 60 mm or 25 mm±2 mm) and introduced into a vacuum oven held at 170° C. After 15 minutes at ambient pressure, the pressure is lowered to 10 mbar, and the adhesive composition is subsequently held at 170° C. and at 10 mbar for 45 minutes to remove air bubbles from the adhesive composition. If 170° C. is insufficient to melt the adhesive composition s a temperature 30±10° C. above the melting temperature of the polymer material composition is used. The adhesive composition is removed from the vacuum oven and allowed to cool to ambient lab conditions (23±2° C.) for 90±30 minutes, at which point the adhesive composition is removed from the PTFE bowl and placed between 2 sheets of siliconised paper (such as product number 114918, Mondi Group, Hilm, Austria, or equivalent). A metal shim 500±30 μm in thickness is used in the heated press as a spacer to obtain a film thickness of 500 μm when pressed with a heated press at 90° C. for 60 seconds at a pressure sufficient to form a polymeric film. If 90° C. is insufficient to press a uniform flat film, a temperature approximately 10±5° C. below the melting point of the sample material composition such that the sample material composition is in a semi-solid state is used. The film is stored at least 120 hours in the laboratory at 23±2° C. prior to testing. From the film individual specimens for measurement are punched with a sample cutter to the final specimen dimensions of 20.0 mm by 10.0 mm by 500 µm.

Measurement

To secure the specimen film to the EVF, the specimen is briefly pressed onto the cylinders of the EVF to secure it to the cylinder surfaces. The specimen is placed with its length perpendicular to the axis of rotation of the cylinders.

The specimen mounted on the EVF is then placed in the forced convection oven of the rheometer for thermal conditioning and is kept isothermal at 37±0.5° C. for 300±10 s. After this time has elapsed, the specimen is mechanically conditioned. To mechanically condition the specimen, the torque transducer is zeroed, and the sample is put under a pre-stretch rate of 0.001 $s^{-1}$ for 0.30 s and then allowed to relax for 60 s (in this method, all strain is expressed in terms of Hencky strain, also known as "true strain" or "logarithmic strain.").

The measurement is performed in the FCO oven at 37° C.±0.5° C. The strain rate extension for the measurement is 1 $s^{-1}$, and the strain at maximum extension is 4.0. After measurement, the specimen is checked for rupturing. If it has ruptured, the location of the break is noted. If the rupture is approximately in the middle between the two cylinders of the EVF, the data collected are deemed acceptable. Otherwise, if the polymeric film break is at or close to the rotating cylinders, the results are discarded, and the measurement performed again on a replicate specimen.

Analysis

For the extensional stress calculation, a constant volume is assumed. From the raw torque versus angular displacement data recorded by the rheometer, extensional stress (in kilopascals, or KPa) versus Hencky strain data are calculated. The data are plotted in semilogarithmic fashion with Hencky strain on the abscissa (linear scale) and extensional stress on the ordinate (logarithmic scale). A linear range is sought in this plot between a Hencky strain of 0.7 and 1.3. The value of the fitted line at a Hencky strain of zero (that is, the y-intercept), is defined as the Yield Stress, which is reported in KPa to the nearest kilopascal.

Peel Force Test Method (PFA to Microfiber Undergarment)

This peel force test method is used to determine the force required to peel a strip of microfiber material from the panty fastening adhesive (PFA) on the garment-facing side of an absorbent article. This method is intended to simulate the removal of an absorbent article adhered to a user's undergarment during use. Peel force is measured on a constant rate of extension tensile tester interfaced to a computer (a suitable instrument is the MTS Alliance using Testsuite software, as available from MTS Systems Corp., Eden Prairie, MN, or equivalent) using a load cell for which the forces measured are within 1%-99% of the limit of the cell. All testing is performed in a room controlled at 23° C.±3° C. and 50%±2% relative humidity and test samples are conditioned in this environment for at least 2 hours prior to testing.

To support the test sample during the peel test, a rigid backing plate (stainless steel with a thickness of about 1.5 mm) is used. The dimensions of the backing plate are governed by the size of the sample being tested as follows. The length of the plate is about 25 mm longer than the overall longitudinal length of the test sample, and the width of the plate is about 10 mm wider than the lateral width of the test sample measured at its widest location (excluding wings).

A strip of microfiber material is used to simulate the wearer's undergarment. The microfiber material used for this peel test is 92% polyester/8% spandex, 130 gsm (or equivalent). This specific material can be obtained from Fruit of the Loom, Inc microfiber briefs (largest size; available from any convenient source). Prior to testing, the material (or intact briefs) are washed 1 time to remove any finishes as follows. The material (or intact briefs) are placed into a high efficiency, front-loading washing machine (any convenient source) along with 48 g of Tide Free and Gentle (or equivalent, without additional additives like odor defense, oxi boost or fabric softener). The washer is set to "normal" cycle using warm wash and rinse water. After the wash cycle, the material (or intact briefs) are placed into a clothes dryer (tumbling with drying sensor; any convenient source). The clothes dryer temperature is set to "regular" and run until dry as indicated by the drying sensor. After drying, the material (or intact briefs) are equilibrated in a room controlled at 23° C.±3° C. and 50%±2% relative humidity for at least 2 hours. Prepare a strip of microfiber material that has a width equal to the widest portion of the PFA pattern with a length that is about 30 mm longer than twice the longitudinal length of the PFA pattern on the sample. The microfiber material strip must be sufficiently wide enough to cover the entire width of the PFA pattern and long enough to cover the entire length of the PFA pattern, overlap itself entirely and still have enough excess leftover to insert into the upper grip of the tensile tester. If the microfiber material is obtained from the briefs, the length of the strip is cut in a direction that is perpendicular to the waistband and should not include any seams, waistband material or gusset. Note which side of the material is intended to face the body (i.e. the inside of the briefs). The length of the microfiber material strip must be long enough to cover the entire longitudinal length of the PFA pattern on the test sample. However, if the strip of microfiber material obtained from the briefs is not sufficiently long enough to overlap itself as previously described, a strip of non-elastic standard cotton material (100% bleached cotton weave, about 100 g/m² available from Testfabrics, Inc., West Pittston, PA, or equivalent) is used to supplement the length of the trailing end of the microfiber strip. The standard cotton is cut to the same width as the microfiber strip and attached to the microfiber strip as follows. One of the longitudinal ends of the strip of standard cotton is placed over the trailing end of the microfiber strip, overlapping the trailing end of the microfiber by 25 mm Ensure the lateral edges of the microfiber and cotton strips are aligned and then secure the standard cotton strip to the microfiber material strip using a piece of masking tape (1" wide; any convenient source) as follows. The masking tape is placed perpendicular to the longitudinal length of the material strips such that its width covers equal portions of the microfiber and cotton strips. The masking tape is sufficiently long enough such that it can cover both sides of the overlapping strips. The masking tape is pressed firmly onto both sides of the material strip to ensure it is properly secured. A fresh microfiber material strip is used for each test sample.

A padded weight assembly is used to ensure adequate and even attachment of the microfiber material strip to the PFA. The weight assembly must impart a pressure of 26-27 g/cm² with a base that has about the same length and width as that of the test sample (width determined at widest location on test sample excluding wings). The weight assembly is constructed as follows. Lay a single layer of polyethylene film (0.02-0.04 mm thick; any convenient source) flat on a bench surface. A piece of flexible insulation foam (Buna-N/PVC, 1 inch thick, density of 4.5 pounds/cubic foot; available from McMaster-Carr, Princeton, NJ, or equivalent) that is cut to the predetermined base size is laid centered on top of the film. A metal weight (same length and width as the predetermined base size) with a handle is then attached to the insulation foam using double sided tape. Next the polyethylene film is wrapped around the insulation foam and secured to the sides of the metal weight using transparent tape.

To prepare the test sample, first remove it from any wrapper present, but leave the PFA protective cover (e.g. release paper) intact. If the wrapper is the protective cover (e.g. PFA is attached directly to the wrapper), then leave the wrapper intact. If the sample is folded, gently unfold it, smooth out any wrinkles and determine which end of the sample is intended to be the front end. If wings are present, unfold the wings. Without disturbing the PFA protective cover, determine the overall length of the PFA pattern using a steel ruler (NIST certified), and record as $PFA_L$ to the nearest mm.

Attach the sample to the backing plate as follows. Lay the backing plate on a horizontally flat rigid surface. With the body facing side of the sample facing down, laterally center the sample over the backing plate and align the front longitudinal edge of the sample within 1 cm from the upper longitudinal edge of the backing plate. The sample is secured to the backing plate using one-sided tape (about 1 inch wide) as follows. The tape is placed no closer than about 1 cm from any portion of the PFA pattern, and no tape is attached to any portion of the PFA protective cover (e.g release paper, wrapper). Secure the front end of the sample to the backing plate by overlapping the end of the sample with a strip of tape positioned approximately parallel to the lateral axis of the sample. Now pull the sample taut to remove any wrinkles and secure the back end of the sample to the backing plate by overlapping the end of the sample with a strip of tape positioned approximately parallel to the lateral axis of the sample. If the sample does not contain wings, secure the entire length of the lateral edge on both sides of the sample to the backing plate using strips of tape. If the sample contains wings, fold each wing around the lateral edges of the backing plate and secure to the backside of the plate with tape. Then in like fashion, secure the remaining length of the lateral edge on both sides of the sample to the top side of the backing plate. The sample is secured in such a way that it is held taut without stretching to keep it flat against the backing plate during the peeling process. In instances where the PFA covers the entire backsheet, tape is used only at the front and back edges of the sample such that the tape overlaps each end by no more than about 1 cm.

After the sample has been secured to the backing plate and still lying on a flat rigid surface with the PFA side of the sample facing up, attach the prepared strip of microfiber material as follows. Remove the PFA protective cover from the sample and determine whether the PFA pattern is continuous in the longitudinal direction (e.g. one or more stripes with no lateral spaces along its longitudinal length). Measure the overall longitudinal length of the PFA pattern and record as $PFA_L$ to the nearest 0.1 mm Now laterally center the microfiber material strip over the sample (inside of briefs facing the sample). Position the leading edge of the microfiber material strip at a distance no more than 1 cm above the front edge of the PFA pattern. Ensure the longitudinal axis of the microfiber material strip is aligned with the longitudinal axis of the sample and secure it to the front edge of the PFA pattern. Continue to apply the microfiber material strip over the remaining portion of the PFA pattern without creating any wrinkles in the microfiber or sample. By design, there will be an excess length of microfiber material (or standard cotton if used to supplement the length of the microfiber) trailing off the back longitudinal end of the sample, referred to as the trailing end of the microfiber material strip. Center and then place the prepared weight assembly over the sample on top of the attached microfiber material strip. After 30±2 seconds have elapsed, remove the weight assembly and set it aside. The sample is now prepped for testing and must be analyzed within 1 minute after the weight assembly has been removed.

Program the tensile tester for a constant rate of extension uniaxial elongation with a set path length as follows. The gauge length is governed by the length of the backing plate and is set to a distance that is about 10 mm greater than the length of the backing plate that will not be within the lower grip. The gauge length is set using a calibrated ruler traceable to NIST, or equivalent. Zero the crosshead and load cell. The path length is governed by the length of the PFA pattern, $PFA_L$, and is set to a distance that is about 5 mm greater than $PFA_L$. Without disturbing the attached strip of microfiber material, insert about 10 mm of the bottom longitudinal edge of the backing plate (where the back end of the test sample is secured) into the grip of the bottom fixture of the tensile tester ensuring that no part of the sample is within the grip. The backing plate must be centered and parallel to the central pull axis of the tensile tester. Now insert the trailing end of the microfiber material strip (or standard cotton if used to supplement the length of the microfiber material) into the grip of the upper fixture of the tensile tester. Ensure the material strip is centered and parallel to the central pull axis of the tensile tester. Adjust the amount of the material strip in the upper grip in order to minimize the slack of microfiber material (and cotton if it was used) at the back end of the PFA pattern, and ensure there is ≤0.1 N of tension to prevent pre-mature peeling. Raise the crosshead at a rate of 1016 mm/min for the entire path length, collecting force (N) and extension (mm) data at 50 Hz throughout the test. Return the crosshead to its original location. Construct a graph of force (N) versus extension (mm).

For test samples that have a PFA pattern that is continuous in the longitudinal direction, calculate the Average Force $(F_a)$ along the path length, excluding all datapoints within the initial and final 1 cm of path length, and record to the nearest 0.01 N. In like fashion, repeat the test for a total of five replicate test samples. Calculate the arithmetic mean for Average Force $(F_a)$ and report as Microfiber Undergarment Average Force to the nearest 0.01 N.

For test samples that have a PFA pattern that is not continuous in the longitudinal direction (e.g. one or more spaces present along its longitudinal length), the resultant graph will consist of a series of peaks (adhesive region) and valleys (non-adhesive region). For this type of sample, the maximum force at each peak along the path length, excluding all datapoints within the initial and final 1 cm of path length, is recorded to the nearest 0.01 N. Now calculate the Average of Peak Forces $(F_p)$ for all of the peaks and record to the nearest 0.01 N. In like fashion, repeat the test for a total of five replicate test samples. Calculate the arithmetic mean for Average of Peak Forces $(F_p)$ and report as Microfiber Undergarment Average of Peak Forces to the nearest 0.01 N.

Adhesive Residue Test Method

This test method is intended to simulate in-use removal of an absorbent article adhered to the user's undergarment via PFA (Panty Fastening Adhesive). Post removal, the presence of residual adhesive on the undergarment is determined by visual inspection after enhancing the appearance of the residue with carbon black paper. All testing is performed in a room controlled at 23° C.±3° C. and 50%±2% relative humidity and test samples are conditioned in this environment for at least 2 hours prior to testing.

To support the undergarment during the removal of the test sample in a realistic manner, a pair of cylinders are used to simulate a user's lower legs. Each cylinder is 6 inches in diameter, about 18 inches tall and composed of high-density polypropylene foam (e.g. Amazon Basics High Density Round Foam Roller, available from Amazon.com, or equivalent). The cylinders are mounted about 6 inches apart on a rigid base large enough to prevent tipping, and they are secured in such a way as to prevent rotation during use.

Women's size 8, white, 100% cotton briefs made by Fruit of the Loom, Inc (available from any convenient source), or equivalent, are used as the undergarments for this test. Prior to use, the cotton briefs are washed 30 times to remove any finishes as follows. The cotton briefs are placed into a high efficiency, front-loading washing machine (any convenient source) along with 48 g of Tide Free and Gentle (or equivalent, without additional additives like odor defense, oxi boost or fabric softener). The washer is set to "normal" cycle using warm wash and rinse water. After the wash cycle, the briefs are placed into a clothes dryer (tumbling with drying sensor; any convenient source). The clothes dryer temperature is set to "regular" and run until dry as indicated by the drying sensor. This entire wash/dry cycle is repeated 30 times. After the thirtieth drying cycle, the cotton briefs are equilibrated in a room controlled at 23° C.±3° C. and 50%±2% relative humidity for at least 2 hours.

A foam pad, a rigid weight and a surface warmer are used to ensure adequate and even attachment of the test sample to the cotton briefs. The foam pad is a piece of flexible insulation foam (Buna-N/PVC, 1 inch thick, density of 4.5 pounds/cubic foot; available from McMaster-Carr, Princeton, NJ, or equivalent) cut to a size of 69 mm by 305 mm. To prevent shedding when in contact with the white, cotton briefs, the foam pad is lightly wrapped with a paper towel secured with masking tape. The rigid, flat contact surface weight is 69 mm by 305 mm and has a handle attached. The rigid weight can be made of any material (e.g. stainless steel) to give a total mass (including handle) of 10.65 kg (0.72 psi imparted by the surface area of the weight). The surface warmer must be able to accommodate a set temperature of 37° C. and have a contact surface area large enough to house the test sample, pad and rigid weight. A suitable surface warmer is the Premiere Slide Warmer, model XH-2001 (available from Amazon.com), or equivalent.

To enhance the appearance of any adhesive residue left behind on the white cotton briefs, carbon black paper is used. A suitable paper is the Pelikan carbon 1015G paper in size A4 (21×31 cm) available from any convenient source, or equivalent paper and size.

The test sample is attached to the cotton briefs as follows. Place the foam pad lengthwise on the outside of the gusset/crotch region of a pair of the pre-washed/dried cotton briefs. Now turn the briefs inside out, conforming the gusset/crotch region over the foam pad in order to ensure a flat, unwrinkled inner surface of the briefs. Place the foam pad and briefs assembly on a flat, rigid surface with the inside of the gusset/crotch region of the briefs facing up, and note which end is the front of the briefs. Remove the test sample from any outer packaging, unfold it and determine which end is intended to be the front end of the pad. If wings are present, cut them from the test sample using a scissor with care so as not to disturb the absorbent body or PFA of the test sample. Remove the protective cover from the PFA on the test sample. Align the front fold line of the test sample with the front edge of the gusset on the briefs, centering it laterally over the crotch region, then attach it to the briefs with just enough hand pressure to secure it. If the test sample is not tri-folded, align the front third of the test sample with the front edge of the gusset on the briefs and proceed in like fashion. Now turn the briefs right side out and place the foam pad on the inside of the gusset/crotch region of the briefs, centered on top of the attached test sample. Set the surface warmer to 37° C. and allow it to reach the temperature set point. Place the briefs, test sample and foam pad assembly onto the surface warmer with the outer side of gusset/crotch region of the briefs in contact with the warmer. Now place the rigid 0.72 psi weight centered on top the foam pad and start a 5-minute timer. After 5 minutes has elapsed, remove the weight and foam pad from the briefs and take the briefs off of the surface warmer.

The test sample is removed from the briefs as follows. The briefs with the attached test sample are placed onto the foam cylinders that represent the user's legs. With the briefs upside down, place one leg hole over one of the cylinders and then the other leg hole over the other cylinder. Firmly grasp the front side of the briefs close to where the front end of the test sample is attached. Now firmly grasp the front end of the test sample. Pull the front end of the test sample in a front-to-back direction to remove it from the briefs in a swift motion (about 200 mm/sec). The motion to remove the test sample from the briefs is meant to realistically mimic the removal of a pad from an undergarment.

The presence of adhesive residue is determined as follows. Remove the cotton briefs from the cylinders, using care not to disturb the inner side of the gusset where the test sample was removed. Place the briefs on a flat, rigid surface with the inside of the gusset/crotch region of the briefs facing up. Place 1 sheet of the carbon black paper centered over the inside gusset of the briefs where the test sample was removed. Now place the rigid 0.72 psi weight lengthwise over the paper, centered over the gusset, ensuring that the placement of the weight does not cause any movement of the carbon black paper on the briefs. Alternatively, in lieu of the rigid weight, apply pressure by hand to the carbon paper along the area where the test sample was removed. After 15 seconds have elapsed, remove the weight and the carbon black paper. Visually observe the entire inside area of the briefs where the test sample was removed to determine the presence of any adhesive residue (now black from the carbon paper). Even a tiny dot of black is indicative of residue and should be reported as such.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a longitudinal centerline, a transverse centerline generally perpendicular to the longitudinal centerline, a wearer-facing surface and an opposing garment-facing surface, a front end region, an opposing back end region, and a central region disposed between the front end region and the back end region, the absorbent article further comprising:
   a topsheet;
   a backsheet;
   an absorbent system disposed between the topsheet and the backsheet; and
   a plurality of pre-formed adhesive portions disposed on the garment-facing surface, wherein the absorbent article exhibits a peel force of at least 1.0 N, in accordance with the Peel Force test, and leaves no residue in accordance with the Adhesive Residue test method;
   wherein each of the pre-formed adhesive portions comprise a leading portion and a trailing portion, wherein the pre-formed adhesive portions have a substantially uniform basis weight from the leading portion to the trailing portion;
   wherein the pre-formed adhesive portions are applied to the absorbent article in solid form; and
   wherein the adhesive portions are polyacrylate based or comprise a mixture of ethylene-vinyl acetate and styrene block copolymer.

2. The absorbent article of claim 1, wherein the absorbent article exhibits a peel force of from between 1.0 N and about 5.0 N.

3. The absorbent article of claim 1, wherein the plurality of adhesive portions is disposed in the front end region and the back end region.

4. The absorbent article of claim 3, wherein the front end region comprises one or more adhesive portions and wherein a length of the one or more pre-formed portions is at least about 15 percent of a length of the front end region.

5. The absorbent article of claim 3, wherein the front end region comprises one or more adhesive portions and where a length of the one or more pre-formed portions is at least about 30 percent of the length of the front end region.

6. The absorbent article of claim 1, wherein the pre-formed adhesive portions comprise a double-sided tape.

7. The absorbent article of claim 6, wherein the double-sided tape comprises a substrate sandwiched between two layers of adhesive.

8. The absorbent article of claim 1, wherein the central region does not comprise adhesive portions.

9. The absorbent article of claim 1, wherein the adhesive portions exhibit each of the following: a tan delta—1 value of between 0.28 to 1.2, over a frequency range of between 0.01 Hz and 1 Hz at 37 degrees C. in accordance with the Frequency Sweep—Oscillatory Rheometry Test Method; a storage modulus—1 value of less than 85 kPa, between 0.01 and 1 Hz at 37 degrees C. in accordance with the Frequency Sweep Oscillatory Rheometry Test Method; a tan delta—2 value of 1.9 or less, over a frequency range of between 50 and 100 Hz at 37 degrees C. in accordance with the Frequency Sweep—Oscillatory Rheometry Test Method; a storage modulus—2 value of greater than 40 kPa, between 50 Hz and 100 Hz at 37 degrees C. in accordance with the Frequency Sweep—Oscillatory Rheometry Test Method, wherein the storage modulus—2 value is greater than storage modulus—1 value.

10. The absorbent article of claim 1, wherein the adhesive portions exhibit a tan delta—2 value of between 0.25 and 1.9 at a frequency range of between 50 Hz and 100 Hz at 37 degrees C.

11. The absorbent article of claim 1, wherein the adhesive portions exhibit a tan delta—2 value of between 0.25 and 1.38, at a frequency range of between 50 Hz and 100 Hz at 37 degrees C.

12. The absorbent article of claim 1, wherein the adhesive portions exhibit a surface energy of between about 10 mJ/m2 to about 25 mJ/m2 in accordance with the Surface Energy method.

13. The absorbent article of claim 1, wherein the adhesive portions exhibit a surface energy of between about 15 mJ/m2 to about 25 mJ/m2 in accordance with the Surface Energy method.

14. The absorbent article of claim 12, wherein the adhesive portions exhibit a polar component of surface energy of between 1 percent to 10 percent.

15. The absorbent article of claim 1, wherein the adhesive portions have a storage modulus—1 value of between 1 kPa and 84 kPa, at a frequency of between 0.01 and 1 Hz at 37 degrees C.

16. The absorbent article of claim 1, wherein the adhesive portions exhibit a relaxation time of 100 seconds or less, at a temperature of 37 degrees C.

17. The absorbent article of claim 1, wherein the adhesive portions exhibit a yield stress of 32 kPa or greater.

18. The absorbent article of claim 1, wherein the adhesive portions exhibit a yield stress of from between about 32 kPa to about 100 kPa.

19. The absorbent article of claim 1, wherein at least one of the front end region and the back end region comprise adhesive portions having a length of from about 25 mm to about 100 mm.

20. An absorbent article comprising a longitudinal centerline, a transverse centerline generally perpendicular to the longitudinal centerline, a wearer-facing surface and an opposing garment-facing surface, a front end region, an opposing back end region, and a central region disposed between the front end region and the back end region, the absorbent article further comprising:
   a topsheet;
   a backsheet;
   an absorbent system disposed between the topsheet and the backsheet; and
a plurality of pre-formed adhesive portions disposed on the garment-facing surface;
   wherein the pre-formed adhesive portions comprise a double-sided tape comprising a mixture of ethylene-vinyl acetate and styrene block copolymer;
   wherein the adhesive portions exhibit each of the following: a tan delta—1 value of between 0.28 to 1.2, over a frequency range of between 0.01 Hz and 1 Hz at 37 degrees C. in accordance with the Frequency Sweep—Oscillatory Rheometry Test Method; a storage modulus—1 value of less than 85 kPa, between 0.01 and 1 Hz at 37 degrees C. in accordance with the Frequency Sweep—Oscillatory Rheometry Test Method; a tan delta—2 value of 1.9 or less, over a frequency range of between 50 and 100 Hz at 37 degrees C. in accordance with the Frequency Sweep—Oscillatory Rheometry Test Method; a storage modulus—2 value of greater than 40 kPa, between 50 Hz and 100 Hz at 37 degrees C. in accordance with the Frequency Sweep—Oscillatory Rheometry Test Method, wherein the storage modulus—2 value is greater than storage modulus—1 value.

* * * * *